United States Patent
Glanville

(10) Patent No.: US 10,836,797 B2
(45) Date of Patent: Nov. 17, 2020

(54) EPITOPE FOCUSING BY VARIABLE EFFECTIVE ANTIGEN SURFACE CONCENTRATION

(71) Applicant: Distributed Bio, Inc., South San Francisco, CA (US)

(72) Inventor: Jacob E. Glanville, South San Francisco, CA (US)

(73) Assignee: Distributed Bio, Inc., South San Francisco, CA (US)

(*) Notice: Subject to any disclaimer, the term of this patent is extended or adjusted under 35 U.S.C. 154(b) by 0 days.

(21) Appl. No.: 16/231,294

(22) Filed: Dec. 21, 2018

(65) Prior Publication Data

US 2019/0375798 A1    Dec. 12, 2019

Related U.S. Application Data

(63) Continuation of application No. 15/833,365, filed on Dec. 6, 2017, now Pat. No. 10,196,427, which is a continuation of application No. 14/398,084, filed as application No. PCT/US2013/042098 on May 21, 2013, now Pat. No. 9,884,893.

(60) Provisional application No. 61/801,135, filed on Mar. 15, 2013, provisional application No. 61/649,392, filed on May 21, 2012.

(51) Int. Cl.

| | | |
|---|---|---|
| C07K 16/28 | (2006.01) |
| A61K 39/395 | (2006.01) |
| C07H 21/04 | (2006.01) |
| C12Q 1/68 | (2018.01) |
| A61K 38/46 | (2006.01) |
| C07K 14/005 | (2006.01) |
| G16B 30/00 | (2019.01) |
| G16B 35/00 | (2019.01) |
| G16C 20/60 | (2019.01) |
| A61K 39/00 | (2006.01) |
| A61K 39/12 | (2006.01) |
| A61K 39/21 | (2006.01) |
| C12N 7/00 | (2006.01) |
| G16B 20/00 | (2019.01) |

(52) U.S. Cl.
CPC ........... *C07K 14/005* (2013.01); *A61K 38/46* (2013.01); *A61K 39/0011* (2013.01); *A61K 39/12* (2013.01); *A61K 39/21* (2013.01); *C12N 7/00* (2013.01); *G16B 30/00* (2019.02); *G16B 35/00* (2019.02); *G16C 20/60* (2019.02); *A61K 2039/515* (2013.01); *A61K 2039/5154* (2013.01); *A61K 2039/53* (2013.01); *A61K 2039/575* (2013.01); *A61K 2039/70* (2013.01); *C12N 2740/16034* (2013.01); *C12N 2740/16071* (2013.01); *C12N 2740/16122* (2013.01); *C12N 2740/16134* (2013.01); *C12N 2760/16122* (2013.01); *C12N 2760/16134* (2013.01); *C12Y 306/05002* (2013.01); *G16B 20/00* (2019.02)

(58) Field of Classification Search
CPC .. G16B 20/00; G16B 30/00; C07K 2317/622; A61K 2039/505; A61K 2039/507
See application file for complete search history.

(56) References Cited

U.S. PATENT DOCUMENTS

| | | |
|---|---|---|
| 4,215,051 A | 7/1980 | Palmer et al. |
| 4,766,072 A | 8/1988 | Jendrisak et al. |
| 4,946,778 A | 8/1990 | Ladner et al. |
| 5,500,161 A | 3/1996 | Andrianov et al. |
| 6,210,891 B1 | 4/2001 | Nyren et al. |
| 6,309,824 B1 | 10/2001 | Drmanac |
| 6,401,267 B1 | 6/2002 | Drmanac |
| 6,828,100 B1 | 12/2004 | Ronaghi |
| 6,833,246 B2 | 12/2004 | Balasubramanian |
| 6,864,052 B1 | 3/2005 | Drmanac et al. |
| 6,911,345 B2 | 6/2005 | Quake et al. |
| 7,232,656 B2 | 6/2007 | Balasubramanian et al. |
| 7,419,669 B2 | 9/2008 | Kosmatopoulos et al. |
| 7,459,311 B2 | 12/2008 | Nyren et al. |
| 7,648,824 B2 | 1/2010 | Nyren et al. |
| 9,884,893 B2 | 2/2018 | Glanville |
| 10,196,427 B2 | 2/2019 | Glanville et al. |

(Continued)

FOREIGN PATENT DOCUMENTS

| | | |
|---|---|---|
| WO | WO-0211748 A1 | 2/2002 |
| WO | WO-2013177214 A2 | 11/2013 |

OTHER PUBLICATIONS

Alexandrov, et al. Fast Protein Fold Recognition via Sequence to Structure Alignment and Contact Capacity Potentials. Protein Science Bulletin, 1996.

(Continued)

*Primary Examiner* — Barry A Chestnut
(74) *Attorney, Agent, or Firm* — Wilson Sonsini Goorich & Rosati

(57) ABSTRACT

The present disclosure provides compositions and methods for the generation of an antibody or immunogenic composition, such as a vaccine, through epitope focusing by variable effective antigen surface concentration. Generally, the composition and methods of the disclosure comprise three steps: a "design process" comprising one or more in silico bioinformatics steps to select and generate a library of potential antigens for use in the immunogenic composition; a "formulation process", comprising in vitro testing of potential antigens, using various biochemical assays, and further combining two or more antigens to generate one or more immunogenic compositions; and an "administering" step, whereby the immunogenic composition is administered to a host animal, immune cell, subject or patient. Further steps may also be included, such as the isolation and production of antibodies raised by host immune response to the immunogenic composition.

17 Claims, 5 Drawing Sheets

(56) References Cited

U.S. PATENT DOCUMENTS

| | | | |
|---|---|---|---|
| 2003/0022285 A1* | 1/2003 | Chirino | C07K 1/00 506/8 |
| 2004/0210037 A1 | 10/2004 | Zauderer et al. | |
| 2005/0191656 A1 | 9/2005 | Drmanac et al. | |
| 2007/0207482 A1 | 9/2007 | Church et al. | |
| 2009/0018024 A1 | 1/2009 | Church et al. | |
| 2009/0028891 A1 | 1/2009 | Timms et al. | |
| 2010/0105052 A1 | 4/2010 | Drmanac et al. | |
| 2011/0129497 A1 | 6/2011 | Bonnin et al. | |
| 2012/0034254 A1* | 2/2012 | Kwong | A61K 39/21 424/188.1 |

OTHER PUBLICATIONS

Ampol, et al. Comprehensive investigation of common antibody-dependent cell-mediated cytotoxicity antibody epitopes of HIV-1 CRF01_AE gp120. AIDS Res Hum Retroviruses. Oct. 2012;28(10):1250-8. Epub May 3, 2012.
Ausubel, et al. Current Protocols in Molecular Biology. John Wiley & Sons, New York, N.Y., 1995.
Baba, et al. Human neutralizing monoclonal antibodies of the IgG1 subtype protect against mucosal simian-human immunodeficiency virus infection. Nat Med. Feb. 2000;6(2):200-6.
Banchereau, et al. Dendritic cells and the control of immunity. Nature. Mar. 19, 1998;392(6673):245-52.
Batzer, et al. Enhanced evolutionary PCR using oligonucleotides with inosine at the 3'terminus. Nucleic Acids Res. Sep. 25, 1991;19(18):5081.
Beachey, et al. Protective immunogenicity and T lymphocyte specificity of a trivalent hybrid peptide containing NH2-terminal sequences of types 5, 6, and 24 M proteins synthesized in tandem. The Journal of experimental medicine 166.3 (1987): 647-656.
Berg, et al. Biochemistry. 5th Edition, W.H. Freeman, N.Y., 2002.
Bowie, et al. A method to identify protein sequences that fold into a known three-dimensional structure. Science. Jul. 12, 1991;253(5016):164-70.
Bowtell, et al. DNA Microarrarys: A Molecular Cloning Manual. Cold Spring Harbor Laboratory Press, 2003.
Broglie, et al. Light-regulated expression of a pea ribulose-1,5-bisphosphate carboxylase small subunit gene in transformed plant cells. Science. May 25, 1984;224(4651):838-43.
Bryant, et al. An empirical energy function for threading protein sequence through the folding motif. Proteins. May 1993;16(1):92-112.
Cole, et al. The EBV-hybridoma technique and its application to human lung cancer. Monoclonal Antibodies and Cancer Therapy 27 (1985): 77-96.
Coligan. Current Protocols in Immunology. John Wiley & Sons, Hoboken, N.Y., 2007.
Coruzzi et al. Tissue-specific and light-regulated expression of a pea nuclear gene encoding the small subunit of ribulose-1,5-bisphosphate carboxylase. EMBO J. 3 (1984): 1671-1680.
Dahiyat, et al. De novo protein design: fully automated sequence selection. Science. Oct. 3, 1997;278(5335):82-7.
Dahiyat, et al. Protein design automation. Protein Sci. May 1996;5(5):895-903.
Dale, et al. Recombinant tetravalent group a streptococcal M protein vaccine. The Journal of Immunology 151.4 (1993): 2188-2194.
Dao, et al. Peptide vaccines for myeloid leukaemias. Best Pract Res Clin Haematol. Sep. 2008;21(3):391-404.
Desjarlais, et al. De novo design of the hydrophobic cores of proteins. Protein Sci. Oct. 1995;4(10):2006-18.
Dieffenbach. PCR Primer: A Laboratory Manual. Cold Spring Harbor Laboratory Press, 2003.
Eddy. Profile hidden Markov models. Bioinformatics. 1998;14(9):755-63.
Eswar, et al. Comparative Protein Structure Modeling Using Modeller. Current Protocols in Bioinformatics, John Wiley & Sons, Inc., Supplement 15, 5.6.1-5.6.30, 200.

European search report and search opinion dated Dec. 2, 2015 for EP Application No. 12793347.9.
"European search report and search opinion dated Apr. 5, 2016 for EP Application No. 12793347.9.".
Gait. Oligonucleotide Synthesis: A Practical Approach. IRL Press, London, 1984.
Gurley et al. Upstream sequences required for efficient expression of a soybean heat shock gene. Mol. Cell. Biol. 6 (1986): 559-565.
Harbury, et al. Repacking protein cores with backbone freedom: structure prediction for coiled coils. Proc Natl Acad Sci U S A. Aug. 29, 1995;92(18):8408-12.
Harlow, et al. Antibodies: A Laboratory Manual. Cold Spring Harbor Laboratory Press, 1988.
Havel, et al. The combinatorial distance geometry method for the calculation of molecular conformation. I. A new approach to an old problem. J Theor Biol. Oct. 7, 1983;104(3):359-81.
Havel, et al. The combinatorial distance geometry method for the calculation of molecular conformation. II. Sample problems and computational statistics. J Theor Biol. Oct. 7, 1983;104(3):383-400.
Hellinga, et al. Optimal sequence selection in proteins of known structure by simulated evolution. Proc Natl Acad Sci U S A. Jun. 21, 1994;91(13):5803-7.
Hellinga. The construction of metal centers in proteins by rational design. Fold Des. 1998;3(1):R1-8.
Hendlich, et al. Identification of native protein folds amongst a large number of incorrect models. The calculation of low energy conformations from potentials of mean force. J Mol Biol. Nov. 5, 1990;216(1):167-80.
International search report and written opinion dated Dec. 16, 2013 for PCT Application No. US2013/042098.
Jones. De novo protein design using pairwise potentials and a genetic algorithm. Protein Sci. Apr. 1994;3(4):567-74.
Kohler, et al. Continuous cultures of fused cells secreting antibody of predefined specificity. Nature. Aug. 7, 1975;256(5517):495-7.
Kono, et al. Energy minimization method using automata network for sequence and side-chain conformation prediction from given backbone geometry. Proteins. Jul. 1994;19(3):244-55.
Kotloff, et al. Safety and Immunogenicity of A Recombinant Multivalent Group A Streptococcal Vaccine in Healthy Adults Phase 1 Trial. JAMA, Aug. 11, 2004, vol. 292, No. 6; pp. 709-715.
Kozbor, et al. The production of monoclonal antibodies from human lymphocytes. Immunol Today. Mar. 1983;4(3):72-9. doi: 10.1016/0167-5699(83)90123-8.
Kuge, et al. Use of a fusion protein to obtain crystals suitable for X-ray analysis: crystallization of a GST-fused protein containing the DNA-binding domain of DNA replication-related element-binding factor, DREF. Protein Sci. Aug. 1997;6(8):1783-6.
Li, et al. A photocleavable fluorescent nucleotide for DNA sequencing and analysis. Proc Natl Acad Sci U S A. Jan. 21, 2003;100(2):414-9. Epub Jan. 6, 2003.
Lin, et al. Th1-Th17 Cells Mediate Protective Adaptive Immunity Against *Staphylococcus aureus* and Candida Albicans Infection in Mice. Plos Pathogens. Dec. 2009, vol. 5, No. 12; pp. 1-10.
McCafferty, et al. Phage antibodies: filamentous phage displaying antibody variable domains. Nature. Dec. 6, 1990;348(6301):552-4.
Mitchell. Cancer vaccines, a critical review—Part II. Curr Opin Investig Drugs. Jan. 2002;3(1):150-8.
Miyazawa, et al. Estimation of effective interresidue contact energies from protein crystal structures: quasi-chemical approximation. Macromolecules, 1985, 18 (3), pp. 534-552.
Mizukami, et al. Receptor activator of NF-kappaB ligand (RANKL) activates TAK1 mitogen-activated protein kinase kinase kinase through a signaling complex containing RANK, TAB2, and TRAF6. Mol Cell Biol. Feb. 2002;22(4):992-1000.
Mount. Bioinformatics: Sequence and Genome Analysis. Cold Spring Harbor Laboratory Press, 2004.
Needleman, et al. A general method applicable to the search for similarities in the amino acid sequence of two proteins. J Mol Biol. Mar. 1970;48(3):443-53.
Nelson, et al. Principles of Biochemistry. 3rd Edition, W.H. Freeman, N.Y., 2000.

(56) References Cited

OTHER PUBLICATIONS

Ohtsuka, et al. An alternative approach to deoxyoligonucleotides as hybridization probes by insertion of deoxyinosine at ambiguous codon positions. J Biol Chem. Mar. 10, 1985;260(5):2605-8.
Parmiani, et al. Unique human tumor antigens: immunobiology and use in clinical trials. J Immunol. Feb. 15, 2007;178(4):1975-9.
Pearson, et al. Improved Tools for Biological Sequence Comparison. Proc. Nat'l Acad. Sci. USA. 85 (1988): 2444-48.
Rossolini, et al. Use of deoxyinosine-containing primers vs degenerate primers for polymerase chain reaction based on ambiguous sequence information. Mol Cell Probes. Apr. 1994;8(2):91-8.
Sambrook, et al. Molecular Cloning: A Laboratory Manual. Cold Spring Harbor Laboratory Press, 2001.
Schlom, et al. Cancer vaccines: moving beyond current paradigms. Clin Cancer Res. Jul. 1, 2007;13(13):3776-82.
Scott, et al. Searching for peptide ligands with an epitope library. Science. Jul. 27, 1990;249(4967):386-90.
Smith, et al. Comparison of Biosequences. Advances in Applied Mathematics. 1981;2: 482-489.
Smith, et al. Molecular Engineering of the Autographa californica Nuclear Polyhedrosis Virus Genome: Deletion Mutations Within the Polyhedrin Gene. J Virol. May 1983;46(2):584-93.
Stryer. Biochemistry. 4th Edition, W.H. Freeman, N.Y., 1995.
Takamatsu et al. Expression of bacterial chloramphenicol acetyltransferase gene in tobacco plants mediated by TMV-RNA. EMBO J. 1987;6:307-311.
Villen, et al. Towards A Multi-Site Synthetic Vaccine to Foot-and-Mouth Disease: Addition of Discontinuous Site Peptide Mimic Increases The Neutralization Response in Immunized Animals. Vaccine 2004, vol. 22; pp. 3523-3529.
Notice of allowance dated Oct. 23, 2017 for U.S. Appl. No. 14/398,084.
Office Action dated Mar. 28, 2017 for U.S. Appl. No. 14/398,084.
Office action dated Sep. 7, 2016 for U.S. Appl. No. 14/398,084.
U.S. Appl. No. 15/833,365 Notice of Allowance dated Oct. 16, 2018.
U.S. Appl. No. 15/833,365 Office Action dated Aug. 3, 2018.
U.S. Appl. No. 14/398,084 Notice of Allowance dated Dec. 5, 2017.
Glanville et al. Naive antibody gene-segment frequencies are heritable and unaltered by chronic lymphocyte ablation. PNAS 108(50):20066-20071 (Dec. 13, 2011). DOI: https://doi.org/10.1073/pnas.1107498108.
Glanville et al. Deep sequencing in library selection projects: what insight does it bring? Current Opinion in Structural Biology 33:146-160 (Aug. 2015). DOI: https://doi.org/10.1016/j.sbi.2015.09.001.
Glanville et al. Identifying specificity groups in the T cell receptor repertoire. Nature 547:94-98 (Jul. 6, 2017).
Glanville et al. Precise determination of the diversity of a combinatorial antibody library gives insight into the human immunoglobulin repertoire. PNAS 106(48):20216-20221 (Dec. 1, 2009). URL: https://doi.org/10.1073/pnas.0909775106.
Zhai et al. Synthetic antibodies designed on natural sequence landscapes. J Mol Biol 412(1):55-71 (Sep. 9, 2011). Epub Jul. 23, 2011. doi: 10.1016/j.jmb.2011.07.018.

\* cited by examiner

Design Process:
In silico generation of the immunogenic composition comprising antigen variants

⬇

101

Formulation Process:
In vitro biochemical formulation of the immunogenic composition

⬇

102

Administering Process:
In vivo administration of immunogenic composition to immune cell or subject

Fig. 2

- 200 Antigen Structural Analysis
- 201 Antigen Homolog Alignment
- 202 Epitope Identification
- 203 Surface Heterogeneity Optimization
- 204 Variable Surface Concentration Ensemble Generation

EPITOPE FOCUSING BY VARIABLE EFFECTIVE ANTIGEN SURFACE CONCENTRATION

This application is a continuation of U.S. patent application Ser. No. 15/833,365, filed Dec. 6, 2017, now U.S. Pat. No. 10,196,427, which is a continuation of U.S. patent application Ser. No. 14/398,084, filed on Oct. 30, 2014, now U.S. Pat. No. 9,884,893, which is a U.S. National Stage Entry of International Application No. PCT/US2013/042098, filed May 21, 2013, which claims the benefit to U.S. Provisional Application 61/649,392, filed May 21, 2012 and U.S. Provisional Application 61/801,135, filed Mar. 15, 2013, each of which are incorporated herein by reference in their entirety.

BACKGROUND

Pathogenic agents such as, infectious bacteria, parasites, fungi, viruses and cancers, have evolved various strategies to evade detection and neutralization by host immune response. Such strategies can often undermine and complicate the development of successful vaccines towards these pathogens. For example, certain parasites have evolved the ability to enter intracellular habitats to avoid the effects of neutralizing antibodies circulating in the blood. Other pathogens, such as trypanosomes have evolved a process known as antigenic variation to change the character of their surface coats. Similarly, pathogens such as some bacteria and viruses have evolved mechanisms to introduce genetic variation in coding regions of their genomes, thereby generating slight alterations to structures of proteins within the pathogen to evade binding by immune cell receptors. Slight changes in variable loops, changes in glycosylation patterns, oligomerization and conformational masking may help the pathogen evade detection and neutralization by immune response molecules such as antibodies.

In some cases, pathogens may display one or more immunodominant epitopes, prone to elicit immune response, but that undergo structural variation or antigenic drift. The host immune response raises early neutralizing antibodies against one or more of these immunodominant epitopes in an attempt to reduce the titer of the dominant pathogenic phenotype. The immunodominant epitopes may also serve to mask immune response to other more conserved epitopes in the pathogen. Antigenic drift of immunodominant epitopes results in these early neutralizing antibodies becoming ineffective against the pathogen. This may occur during the course of a single infection, or over the course of multiple infections.

With respect to human pathogens, the human immunodeficiency virus-1 (HIV-1) provides an example of a highly effective strategy used to evade, and so to destroy, the human immune system. None of the vaccine approaches that have been attempted to date have proved successful due to the high prevalence of antigenic drift in multiple immunodominant epitopes of HIV-1 capsid proteins. Typical approaches using subunit vaccine strategies have failed, as the virus is able to evolve very quickly to evade neutralization by antibodies raised during vaccination.

The influenza virus hemagglutinin antigen (HA) provides another example of a pathogen-encoded immunodominant antigen that is subject to antigenic drift. Variation in the antigenic structure of HA correlates with the periodic epidemics of respiratory disease that are caused by this virus, despite the widespread use of influenza vaccine.

There is need in the art for novel approaches for the generation of improved vaccines. Specifically, there is a need for methods to generate antibodies to specific or desired epitopes of a particular antigen. In some cases, desired epitopes for vaccine development may be more highly conserved than other immunodominant epitopes. Such methods may be applied to the generation of antibodies for a wide range of antigens and protein targets, or vaccines for numerous human diseases, such as infections caused by viruses and microorganisms as well as cancer.

SUMMARY OF THE DISCLOSURE

In some aspects, the disclosure provides for an immunogenic composition for eliciting an immune response in a subject, the immunogenic composition comprising at least 6 antigens, wherein each antigen comprises a common target epitope, and wherein each antigen of the immunogenic composition comprises an individual concentration insufficient to be immunogenic in the subject.

In some aspects, the disclosure provides for an immunogenic composition for eliciting an immune response in a subject, the immunogenic composition comprising at least 6 antigens, wherein each antigen comprises a common target epitope, and wherein each antigen of the immunogenic composition comprises at least 100 amino acid residues.

In some aspects, the disclosure provides for an immunogenic composition for eliciting an immune response in a subject, the immunogenic composition comprising at least 6 antigens, wherein each antigen comprises: a common target epitope at least 90% identical across all antigens of the immunogenic composition; at most 90% identical sequence in surface exposed regions between any two antigen variants outside of the common target epitope.

In some aspects, the disclosure provides for a unit dose of an immunogenic composition comprising at least 6, antigens, wherein each antigen comprises a common target epitope, and wherein each antigen of the immunogenic composition comprises an individual concentration insufficient to be immunogenic in the subject.

In some aspects, the disclosure provides for a method of generating an immune response to a target epitope, the method comprising: creating with a computing device, a computation-guided library comprising a plurality of antigen variants, wherein each antigen variant comprises: a conserved target epitope region; and one or more non conserved regions, wherein the non conserved regions are outside the target epitope; obtaining a plurality of antigen variants of the computation-guided library; generating an immunogenic composition comprising the plurality of antigen variants, wherein an individual antigen variant is present in the immunogenic composition at an concentration insufficient to be immunogenic.

In some aspects, the immunogenic composition is contacted with an immune cell.

In some aspects, an antibody that binds the target epitope is isolated from the immune cell.

In some aspects, the immune cell is administered for treating or reducing the likelihood of a disease in a human subject in need thereof.

In some aspects, the disclosure provides for a computer executable algorithm for the generation of an immunogenic composition, the algorithm comprising: obtaining a target antigen protein sequence and one or more antigen homolog sequences; obtaining structural models from the target antigen protein sequence and the one or more antigen homolog sequences; aligning the structural models of target antigen and the one or more antigen homologs; extracting a positional weight matrix (PWM) of each amino acid residue frequency of the antigen protein sequence using the alignment of (c); identifying surface exposed amino acid residues in the PWM generated in (d); identifying amino acid residues of one or more target epitopes in the PWM generated in (d); identifying one or more target epitopes in the PWM generated in (d); generating a library of a plurality of antigen variants comprising: diversifying amino acid residues in non target epitope surface exposed amino acid residues of the PWM for each antigen variant; performing pairwise comparisons of one or more non target epitope surface exposed regions comprising at a commonly defined area between antigen variants of the library, wherein antigen variants of the library share at least 30% sequence identity in non surface exposed amino acid residues, and wherein antigen variants of the library share at most 90% sequence identity in non target epitope surface exposed amino acid residues; selecting two or more antigen variants generated in (h); generating an immunogenic composition comprising a plurality of antigen variants, wherein an individual antigen variant in the immunogenic composition is assigned a concentration insufficient to be immunogenic.

In some aspects, the disclosure provides for a computing device comprising a processor; and data storage, storing instructions that, upon execution by the processor, cause the computing device to perform functions comprising: obtaining a target antigen protein sequence and one or more antigen homolog sequences; obtaining structural models from the target antigen protein sequence and the one or more antigen homolog sequences; aligning the structural models of target antigen and the one or more antigen homologs; extracting a positional weight matrix (PWM) of each amino acid residue frequency of the antigen protein sequence using the alignment of (c); identifying surface exposed amino acid residues in the PWM generated in (d); identifying amino acid residues of one or more target epitopes in the PWM generated in (d); identifying one or more target epitopes in the PWM generated in (d); generating a library of a plurality of antigen variants comprising: diversifying amino acid residues in non target epitope surface exposed amino acid residues of the PWM for each antigen variant: performing pairwise comparisons of one or more non target epitope surface exposed regions comprising a commonly defined area between antigen variants of the library, wherein antigen variants of the library share at least 30% sequence identity in non surface exposed amino acid residues, and wherein antigen variants of the library share at most 90% sequence identity in non target epitope surface exposed amino acid residues; selecting two or more antigen variants generated in (h); generating an immunogenic composition comprising a plurality of antigen variants, wherein an individual antigen variant in the immunogenic composition is assigned a concentration insufficient to be immunogenic.

In some aspects the commonly defined area is at least 25 $Å^2$ or is oval in shape.

In some aspects the library of a plurality of antigen variants comprises at least $1 \times 10^6$ antigen variants.

In some aspects, the disclosure provides for a method for generating an immunogenic composition, the method comprising: introducing into a cell, a nucleic acid encoding a plurality of antigen proteins, wherein each antigen comprises a common target epitope; isolating the plurality of antigen proteins; generating an immunogenic composition comprising the plurality of antigen variants, wherein an individual antigen variant in the immunogenic composition is assigned a concentration insufficient to be immunogenic.

In some aspects, the disclosure provides for a kit comprising introducing into a cell, a nucleic acid encoding a plurality of antigen proteins, wherein each antigen comprises a common target epitope; isolating the plurality of antigen proteins; generating an immunogenic composition comprising the plurality of antigen variants, wherein an individual antigen variant in the immunogenic composition is assigned a concentration insufficient to be immunogenic.

In some aspects, the disclosure provides for a method for detecting the presence or absence of an antibody, the method comprising: contacting the immunogenic composition or one or more antigen variants of any of the preceding immunogenic compositions described herein, comprising one or more epitopes, with a composition comprising an antibody, under conditions suitable for binding of the antibody to the one or more epitopes; and detecting one or more epitopes complexed with the antibody.

In some aspects, the disclosure provides for any of the preceding immunogenic compositions described herein for use in a diagnostic for exposure to a pathogen or immune threat.

In some aspects, the disclosure provides for a virus like particle (VLP) comprising an immunogenic composition of preceding immunogenic compositions described herein.

In some aspects, the immune response elicited by the immunogenic composition is determined by an immunoassay.

In some aspects, the immune response elicited by the immunogenic composition is determined by nucleic acid sequencing.

In some aspects, the immunogenic composition elicits an antibody in a B-cell of an immunized subject, and wherein the antibody titers of an immunized subject compared to antibody titers of a non-immunized subject are measured.

In some aspects, the immunogenic composition elicits the production of antibodies.

In some aspects, the immunogenic composition elicits an adaptive immune response, humoral immune response or an innate immune response.

In some aspects, the immune response is a CD4+ T-cell response, including a Th1, Th2 and Th17 response.

In some aspects, the immunogenic composition is administered for treating or reducing the likelihood of a disease in human subject in need thereof.

In some aspects, the disease is selected from the group consisting of: infectious disease, autoimmune disease, inflammatory disease, neurological disease, addiction, cardiovascular disease, endocrine disease and cancer.

In some aspects, the antigen is selected from the group consisting of: pneumococcal antigens, tuberculosis antigens, anthrax antigens, HIV antigens, seasonal or epidemic flu antigens, *influenzae* antigens, Pertussis antigens, *Staphylococcus aureus* antigens, Meningococcal antigens, *Haemophilus* antigens, HPV antigens, or combinations thereof.

In some aspects, the antigen is selected from the group consisting of: protein, peptide, lipoprotein, lipid, carbohydrate, glycoprotein and antigen encoding nucleic acid.

In some aspects, the disclosure provides for recombinant expression vectors comprising nucleic acids encoding a plurality of antigen variants of the immunogenic composition of any of the preceding immunogenic compositions described herein.

In some aspects, the subject is a human.

In some aspects, the antigens share a common protein fold.

In some aspects, non exposed surface residues are not diversified.

In some aspects, immunogenic composition comprises at least 2, 3, 5, 10, 25, 50, 100, 200, 250, 500, 1000, 1500, 5000, or 10000 antigen variants.

In some aspects, the immunogenic composition elicits an antibody in a B-cell of an immunized subject, and wherein the antibody titers are measured to be at least 10-fold, 20-fold, 50-fold, 100-fold, or 1000-fold greater in an immunized subject than in an non-immunized subject.

In some aspects, the immunogenic composition elicits an antibody in a B-cell of an immunized subject, and wherein the antibody affinity for the immunogenic composition or one or more antigen variants of the immunogenic composition is measured.

In some aspects, the antibody affinity is determined by measuring the equilibrium dissociation constant of the antibody for the immunogenic composition or the one or more antigen variants of the immunogenic composition.

In some aspects, the the immunogenic composition elicits an antibody in B cells, wherein the antibody is measured to have a binding equilibrium dissociation constant to the immunogenic composition, or the one or more antigen variants of the immunogenic composition that is less than $10^{-7}$ M, $10^{-8}$ M, $10^{-9}$ M, $10^{-10}$ M, $10^{-11}$ M, or $10^{-12}$ M.

In some aspects the immunogenic composition elicits a class-switch recombination in B cells.

In some aspects the immunogenic composition elicits the antibody isotype produced by the B cells to switch from IgM to IgG.

In some aspects the immunogenic composition elicits an antibody in a B-cell of an immunized subject, and wherein the affinity maturation of antigen-specific antibodies is measured.

In some aspects the immunogenic composition elicits the formation of memory B cells or long-lived plasma cells capable of producing large amounts of high-affinity antibodies for extended periods of time.

In some aspects the immunogenic composition elicits a vigorous germinal center reaction in B cells.

In some aspects the immunogenic composition elicits one or more antibody isotypes, and wherein one or more antibody Isotypes are identified.

In some aspects the immunogenic composition elicits the production of IgG isotype antibodies.

In some aspects the immunogenic composition elicits B cells is determined by analyzing antibody function in neutralization assays.

In some aspects the immunogenic composition elicits helper T cells as determined by antigen-induced production of cytokines by T cells.

In some aspects the stimulation of helper T cell is determined by measuring antigen-induced production of cytokines by T cells.

In some aspects the cytokine is IFNγ, IL-4, IL-2, or TNFα.

In some aspects the immunogenic composition elicits an immune response from T cells, and wherein antigen-induced production of cytokines by T cells is measured by ELISPOT assay.

In some aspects the immunogenic composition elicits T cells, wherein immunized subjects comprise about 10-fold, 100-fold, 1000-fold, 100-fold more cytokine-producing cells than do naive controls.

In some aspects the immunogenic composition elicits T cells, wherein antigen-induced production of cytokines by T cells is measured by determining antigen-induced proliferation of T cells.

In some aspects the immunogenic composition elicits T cells, wherein the stimulation of an immune response in T cells is determined by measuring cellular markers of T cell activation.

In some aspects the immunogenic composition elicits B cells, wherein the stimulation of an immune response in T cells is determined by measuring cellular markers of B cell activation.

In some aspects the immunogenic composition is contacted with an immune cell.

In some aspects the generation of an immunogenic composition comprises generating structural ensembles, designing computation sequences, filtering the computation sequences, recombining designs, conformational re-sampling of a representation of an interacting segment, and receiving an input related to human-guided design and filtering.

In some aspects the data storage is further configured to store at least part of the antigen variant library.

In some aspects the methods of the disclosure are performed using phage, yeast, or mammalian display.

In some aspects a cell of the disclosure is selected from the group consisting of: a bacterial cell, fungal cell, insect cell, animal cell, human cell and plant cell.

In some aspects the immunogenic composition elicits the production of antibodies.

In some aspects the immunogenic composition elicits an adaptive immune response, humoral immune response or an innate immune response.

In some aspects the immunogenic composition is directed towards an antigen related to one member selected from the following group consisting of: virus, Influenza virus, HIV virus, bacteria, parasite, fungus, infectious disease, autoimmune disease, inflammatory disease, neurological disease, addiction, cardiovascular disease, endocrine disease and cancer.

In some aspects the library of a plurality of antigen variants is at least 2, $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, $1\times10^{20}$, $1\times10^{21}$, $1\times10^{22}$, $1\times10^{23}$, $1\times10^{24}$, or $1\times10^{25}$ antigen variants.

In some aspects the target epitope shares at least 75%, 80%, 85%, 90%, 95%, 99%, 99.9% or 100% homology with target epitopes across a plurality of antigen variants in the antigen library.

In some aspects the non target epitope regions shares at most 50%, 60%, 65%, 70%, 75%, 80%, 85%, 90%, homology with non target epitope regions across a plurality of antigen variants in the antigen library.

In some aspects the antigen is from a chemical weapon or an agent of bio warfare.

In some aspects the antigen is a protein or peptide, lipoprotein, lipid, carbohydrate, nucleic acid or combination thereof.

In some aspects the immunogenic composition comprises a pharmaceutically acceptable carrier, excipient, adjuvant, or vehicle.

In some aspects the immunogenic composition comprises a chemotherapeutic agent, a targeting moiety, an anti-cancer agent, an adjuvant, or a hapten.

In some aspects the immunogenic composition comprises an enzyme.

In some aspects the antibody is a humanized monoclonal antibody.

In some aspects the target epitope is a ligand binding site, functional motif or enzyme active site.

In some aspects the immunogenic composition is selected from the group consisting of: enzyme, vaccine, pharmaceutical and therapeutic.

In some aspects, the immunogenic composition further comprises an agent selected from the following group consisting of: B-cell targeting moiety, T-cell targeting moiety, anti-viral agent, chemotherapeutic agent, a toxin, immunostimulatory agent, adjuvant, and hapten.

INCORPORATION BY REFERENCE

All publications, patents, and patent applications mentioned in this specification are herein incorporated by reference to the same extent as if each individual publication, patent, or patent application was specifically and individually indicated to be incorporated by reference

BRIEF DESCRIPTION OF THE DRAWINGS

The novel features of a device of this disclosure are set forth with particularity in the appended claims. A better understanding of the features and advantages of this disclosure will be obtained by reference to the following detailed description that sets forth illustrative cases, in which the principles of a device of this disclosure are utilized, and the accompanying drawings.

FIG. 1 is a schematic representing 3 processes used for generating an immunogenic composition of the disclosure.

FIG. 2 is a schematic representing various in silico methods for generating a immunogenic composition of the disclosure.

DETAILED DESCRIPTION OF THE DISCLOSURE

I. General Overview

Figure 3:
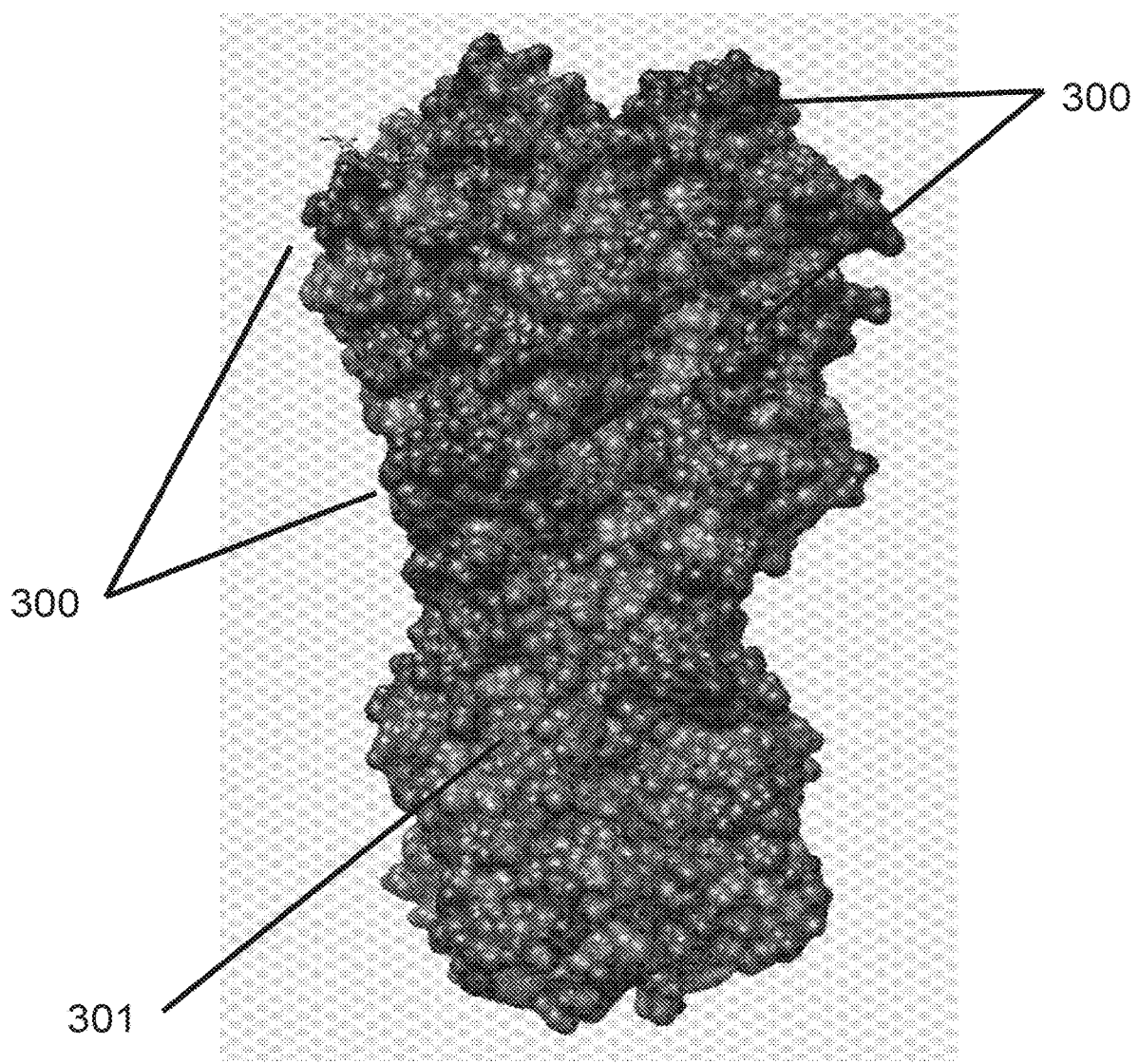
FIG. 3 is a reference structure of the HA protein with various conserved (black) and non conserved (grey) regions of surface exposed epitopes on the HA protein.

The present disclosure provides compositions and methods for the generation of an antibody or immunogenic composition, such as a vaccine, through epitope focusing by variable effective antigen surface concentration. Generally, the composition and methods of the disclosure comprise three processes: a "design process", (100), comprising one or more in silico bioinformatics steps to select and generate a library of potential antigens for use in the immunogenic composition; a "formulation process", (101), comprising in vitro testing of potential antigens, using various biochemical assays, and further combining two or more antigens to generate one or more immunogenic compositions; and an "administering process", (102), whereby the immunogenic composition is administered to immune cells, present either in vitro (i.e. cell culture) or in vivo (i.e. a host animal, subject or patient) as show in FIG. 1. Further steps may also be included, such as the isolation and scalable production of antibodies raised by host immune response to the immunogenic composition.

In the design process, a suite of bioinformatics tools or algorithms are first used to analyze and compare protein structures of an antigen of interest. A plurality of antigen structures, each representing different protein conformations or structural variations (e.g. resulting from mutations or genetic variability) may be compared. An algorithm may be used to generate a map of the protein surfaces of a particular antigen. In some cases, the map may differentiate between areas on the protein surface that are conserved and non-conserved across the plurality of antigen structures compared. In some cases, another algorithmic tool may be used to select one or more epitopes from regions identified as conserved in the antigen map.

After one or more epitopes are selected (i.e. target epitopes), an additional algorithm may be used to generate an in silico library of antigenic variants, each variant comprising one or more conserved target epitopes surrounded by non-conserved diversified surfaces. A subsequent algorithmic step is applied, whereby antigenic variants generated in the previous step may be filtered, according to various criteria, and selected to be combined in a mixture, or "ensemble," to formulate the immunogenic composition. In the formulation of the immunogenic composition, each antigenic variant may be assigned a specific concentration in the ensemble such that the ensemble itself is immunogenic, but that the concentration of individual antigenic variants is not immunogenic, or insufficient to produce an immune response when contacted with an immune cell.

In the formulation process, antigenic variants for one or more ensembles may be expressed and tested biochemically for various factors, such as protein stability and epitope specificity. Individual antigenic variants may be combined in an ensemble, with each variant at a specific concentration as predicted in the previous design process.

After biochemical testing and production of selected antigenic variants, an immunogenic composition is formulated from an ensemble of antigenic variants and subsequently administered to a subject or immune cell. In some cases, the subject may be a human subject in need of vaccination. In some cases, the subject or immune cell may be used to isolate an antibody raised against the immunogenic composition.

The compositions and methods may be particularly useful in variety of medical and biotechnology applications. For example, the compositions and methods of the disclosure may be used to develop vaccines directed towards the prevention and/or treatment of a variety of human diseases, ranging from infectious diseases from microorganisms such as bacteria and viruses, to cancer. In other applications, the compositions and methods of the disclosure may be used for the generation of antibodies, directed to a single epitope of interest in a protein. The generation of specific antibodies to a single epitope may have many applications, including the development of various antibody based tools and therapies for the identification, detection, diagnosis or treatment of various diseases. Further, compositions and methods of the disclosure may be also used to generate antibody based tools for basic research functions, including but not limited to immunoassays, protein purification, protein identification, protein quantification, protein characterization, and protein structural domain mapping.

II. Definitions

The terminology of the present disclosure is for the purpose of describing particular cases only and is not intended to be limiting of compositions, methods and devices of this disclosure.

The compositions and methods of this disclosure as described herein may employ, unless otherwise indicated, conventional techniques and descriptions of molecular biology (including recombinant techniques), cell biology, biochemistry, microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., Genome Analysis: A Laboratory Manual Series (Vols. I-IV) (1999); Weiner, et al., Eds., Genetic Variation: A Laboratory Manual (2007); Dieffenbach, Dveksler, Eds., PCR Primer: A Laboratory Manual (2003); Bowtell and Sambrook, DNA Microarrays: A Molecular Cloning Manual (2003); Mount, Bioinformatics: Sequence and Genome Analysis (2004); Sambrook and Russell, Condensed Protocols from Molecular Cloning: A Laboratory Manual (2006); and Sambrook and Russell, Molecular Cloning: A Laboratory Manual (2002) (all from Cold Spring Harbor Laboratory Press); Stryer, L., Biochemistry (4th Ed.) W.H. Freeman, N.Y. (1995); Gait, "Oligonucleotide Synthesis: A Practical Approach" IRL Press, London (1984); Nelson and Cox, Lehninger, Principles of Biochemistry, 3rd Ed., W.H. Freeman Pub., New York (2000); and Berg et al., Biochemistry, 5th Ed., W.H. Freeman Pub., New York (2002), all of which are herein incorporated by reference in their entirety for all purposes. Before the present compositions, research tools and methods are described, it is to be understood that this disclosure is not limited to the specific methods, compositions, targets and uses described, as such may, of course, vary. It is also to be understood that the terminology used herein is for the purpose of describing particular aspects only and is not intended to limit the scope of the present disclosure, which will be limited only by appended claims.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Ranges can be expressed herein as from "about" one particular value, and/or to "about" another particular value. When such a range is expressed, another case includes from the one particular value and/or to the other particular value. Similarly, when values are expressed as approximations, by use of the antecedent "about," it will be understood that the particular value forms another case. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5. The term "about" also accounts for typical error or imprecision in measurement of values.

As used herein, the term "antibody" is meant to refer to immunoglobulin molecules (e.g., any type, including IgG, IgE, IgM, IgD, IgA and IgY, and/or any class, including, IgG1, IgG2, IgG3, IgG4, IgA1 and IgA2) isolated from nature or prepared by recombinant means or chemically synthesized. The terms "antibody" and "immunoglobulin" can be used interchangeably throughout the specification, unless indicated otherwise.

As used herein, antibody may also refer to an antibody fragment which may represent a portion of a whole antibody which retains the ability to exhibit antigen binding activity or immunogenicity. Antibody and antibody fragment may be used interchangeably herein. Examples of antibodies or antibody fragments include, but are not limited to, Fv, disulphide-linked Fv, single-chain Fv, Fab, variable heavy region (VH), variable light region (VL), and fragments of any of the above antibody fragments which retain the ability to exhibit antigen binding activity, e.g., a fragment of the variable heavy region VH retains its ability to bind its antigen.

As used herein, the term antibody that "specifically (or selectively) binds to" or is "specific for" or is "specifically (or selectively) immunoreactive with" a particular polypeptide or an epitope on a particular polypeptide is one that binds to that particular polypeptide or epitope on a particular polypeptide without substantially binding to any other polypeptide or polypeptide epitope. Antibody affinity for antigens can be measured by enzyme linked immunosorbent assay (ELISA).

Alternatively, an antibody that specifically binds to an antigen, may refer to the binding of an antigen by an antibody or fragment thereof with a dissociation constant (Kd) of at least 3 $\mu$M, 2 $\mu$M, 1 $\mu$M, 900 nM, 800 nM, 700 nM, 600 nM, 500 nM, 400 nM, 300 nM, 200 nM, 100 nM, 1 nM, 900 pM, 800 pM, 700 pM, 600 pM, 500 pM, 400 pM, 300 pM, 200 pM, 100 pM, 1 pM, 900 fM, 800 fM, 700 fM, 600 fM, 500 fM, 400 fM, 300 fM, 200 fM, 100 fM, or 1 fM. In some cases antibodies or fragments thereof may have a dissociation constant (Kd) of at most 3 $\mu$M, 2 $\mu$M, 1 $\mu$M, 900 nM, 800 nM, 700 nM, 600 nM, 500 nM, 400 nM, 300 nM, 200 nM, 100 nM, 1 nM, 900 pM, 800 pM, 700 pM, 600 pM, 500 pM, 400 pM, 300 pM, 200 pM, 100 pM, 1 pM, 900 fM, 800 fM, 700 fM, 600 fM, 500 fM, 400 fM, 300 fM, 200 fM, 100 fM, or 1 fM as measured by any suitable biochemical assay, including but not limited to surface plasmon resonance analysis using, for example, a BIACORE surface plasmon resonance system and BIACORE kinetic evaluation software.

For preparation of monoclonal or polyclonal antibodies, any technique known in the art can be used (see, e.g., Kohler and Milstein, Nature 256:495497 (1975); Kozbor et al, Immunology Today 4:72 (1983); Cole et al, pp. 77-96 in Monoclonal Antibodies and Cancer Therapy, Alan R. Liss, Inc. (1985)). Techniques for the production of single chain antibodies (U.S. Pat. No. 4,946,778) can be adapted to produce antibodies to polypeptides of this disclosure. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al, Nature 348: 552-554 (1990); Marks et al., Biotechnology 10:779-783 (1992)).

The term "immunoassay" is meant to refer to an assay that uses an antibody to specifically bind an antigen. The immunoassay is characterized by the use of specific binding properties of a particular antibody to isolate, target, and/or quantify the antigen.

As used herein, the terms "biological sample" or "patient sample" as used herein, is meant to refer to a sample obtained from an organism or from components (e.g., cells) of an organism. The sample can be of any biological tissue or fluid. The sample may be a clinical sample which is a sample derived from a patient. Such samples include, but are not limited to, sputum, blood, serum, plasma, blood cells (e.g., white cells), tissue samples, biopsy samples, urine, peritoneal fluid, and pleural fluid, saliva, semen, breast exudate, cerebrospinal fluid, tears, mucous, lymph, cytosols, ascites, amniotic fluid, bladder washes, and bronchioalveolar lavages or cells therefrom, among other body fluid samples. The patient samples may be fresh or frozen, and may be treated, e.g. with heparin, citrate, or EDTA, or other suitable treatment known in the art. Biological samples may also include sections of tissues such as frozen sections taken for histological purposes.

As used in this disclosure, the term "epitope" is meant to refer to any antigenic determinant on an immunogen, e.g., any primary immunogen, to which an antibody binds through an antigenic binding site. Determinants or antigenic determinants on an antigen usually consist of chemically active surface groupings of molecules such as amino acids or sugar side chains and usually have specific three dimensional structural characteristics, as well as specific charge characteristics. In some cases, an epitope may be an area of surface exposed residues and/or carbohydrate moieties on an antigen. In some cases, the area ranges from 100 Å-1500 Å. In some cases, an epitope may be defined as a an area of of surface exposed residues on an antigen ranging from at least 25 $Å^2$, 50 $Å^2$, 100 $Å^2$, 200 $Å^2$, 300 $Å^2$, 400 $Å^2$, 500 $Å^2$, 600 $Å^2$, 700 $Å^2$, 800 $Å^2$, 900 $Å^2$, 1000 $Å^2$, 1100 $Å^2$, 1200 $Å^2$, 1300 $Å^2$, 1400 $Å^2$ or 1500 $Å^2$. In some cases, an epitope may be defined as a an area of of surface exposed residues on an antigen ranging from at most 25 $Å^2$, 50 $Å^2$, 100 $Å^2$, 200 $Å^2$, 300 $Å^2$, 400 $Å^2$, 500 $Å^2$, 600 $Å^2$, 700 $Å^2$, 800 $Å^2$, 900 $Å^2$, 1000 $Å^2$, 1100 $Å^2$, 1200 $Å^2$, 1300 $Å^2$, 1400 $Å^2$ or 1500 $Å^2$. In some cases, an epitope may be 650-900. In some cases, an an epitope may range from 650 $Å^2$-750 $Å$, 750 $Å^2$-800 $Å^2$, 800 $Å^2$-850 $Å^2$ or 850 $Å^2$-900 $Å^2$.

A "hapten" is a small molecule that, when attached to a larger carrier such as a protein, can elicit the production of antibodies that bind specifically to it (in either the free or combined state). A "hapten" is able to bind a preformed antibody, but fails to stimulate antibody generation on its own. In the context of this invention, the term "hapten" includes modified amino acids, either naturally occurring or non-naturally occurring. Thus, for example, the term "hapten" includes naturally occurring modified amino acids such as phosphotyrosine, phosphothreonine, phosphoserine, or sulphated residues such as sulphated tyrosine (sulphotyrosine), sulphated serine (sulphoserine), or sulphated threonine (sulphothreonine); and also may include non-naturally occurring modified amino acids such as p-nitro-phenylalanine.

A "hapten-labeled antigen" in the context of this invention refers to a hapten attached to an antigen of interest. The antigen of interest may be a peptide, or protein. The hapten can be positioned anywhere in the epitope of interest.

The terms "isolated," "purified" or "biologically pure" may refer to material that is substantially or essentially free from components that normally accompany it as found in its native state. Purity and homogeneity may be typically determined using analytical chemistry techniques such as polyacrylamide gel electrophoresis or high performance liquid chromatography. A protein that is the predominant species present in a preparation may be substantially purified. The term "purified" may denote that a nucleic acid or protein gives rise to essentially one band in an electrophoretic gel. Particularly, it may indicate that the nucleic acid or protein is at least 85% pure, at least 95% pure, or at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Amino acid may also be referred to as "amino acid residue" or "residue," used interchangeably herein.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. The probes can be directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with a reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed and an operably linked to a promoter.

An "immune cell" is any immune cell capable of providing an immune response to immunogenic stimuli, such as exposure to one or immunogens or ensemble of antigens. Immune cells may include but are not limited to Neutrophils, Eosinophils, Basophils, Lymphocytes, T cells, B cells, Cytotoxic, Plasma cells, T cells, Granulocytes, Helper T cells, Macrophages, Mast cells, Memory cells, Monocytes, platelets, Dendritic cells, antigen presenting cells (APCs), or any cell considered part of an immune system of a host animal or subject. In some cases, an immune cell may also comprise a hybrid of one or more cells. For example, an immune cell may comprise a hybridoma, whereby an immune cell may be fused to an immortalized cell, such as a cancer cell.

The terms "identical" or percent "identity," in the context of two or more nucleic acids or polypeptide sequences, may refer to two or more sequences or subsequences that are the same or have a specified percentage of amino acid residues or nucleotides that are the same. In some cases, 2 or more sequences may be homologous if they share at least 20%, 25%, 30%, 35%, 40%, 45% 50%, 55%, 60% identity, 65%, 70%, 75%, 80%, 85%, 90%, 91%, 92%, 93%, 94%, 95%, 96%, 97%, 98%, 99% or higher identity to a reference sequence when compared and aligned for maximum correspondence over a comparison window, or designated region as measured using one of the following sequence comparison algorithms or by manual alignment and visual inspection. In some cases, 2 or more sequences 2 or more sequences may be homologous if they share at most 20%, 25%, 30%, 35%, 40%, 45% 50%, 55%, 60% identity, 65%, 70%, 75%, 80%, 85%, 90%, 91%, 92%, 93%, 94%, 95%, 96%, 97%, 98%, 99% or higher identity to a reference sequence. This definition also refers to the compliment of a test sequence. Preferably, the identity exists over a region that is at least 25 amino acids or nucleotides in length or in some cases over a region that is 50-100 amino acids or nucleotides in length. In some cases, 2 or more sequences may be homologous and share at least 30% identity over at least 80 amino acids in a sequence according to the Sander-Schneider homology limit.

Alternatively, an indication that two nucleic acid sequences or polypeptides are identical is that the polypeptide encoded by the first nucleic acid is immunologically cross reactive with the antibodies raised against the polypeptide encoded by the second nucleic acid, as described below. Thus, a polypeptide is typically identical to a second polypeptide, for example, where the two peptides differ only by conservative substitutions. Another indication that two nucleic acid sequences are substantially identical is that the two molecules or their complements hybridize to each other under stringent conditions, as described herein.

For sequence comparison, generally one sequence acts as a reference sequence, to which test sequences may be compared. When using a sequence comparison algorithm, test and reference sequences may be entered into a computer, subsequent coordinates may be designated, if necessary, and sequence algorithm program parameters may be designated. Any suitable algorithm may be used, including but not limited to Smith-Waterman alignment algorithm, Viterbi, Bayesians, Hidden Markov and the like. Default program parameters can be used, or alternative parameters can be designated. The sequence comparison algorithm may then be used to calculate the percent sequence identities for the test sequences relative to the reference sequence, based on the program parameters. Any suitable algorithm may be used, whereby a percent identity is calculated. Some programs for example, calculate percent identity as the number of aligned positions that identical residues, divided by the total number of aligned positions.

A "comparison window", as used herein, includes reference to a segment of any one of the number of contiguous or non-contiguous positions which may range from 10 to 600 positions. In some cases the comparison window may comprise at least 10, 20, 50, 100, 200, 300, 400, 500, or 600 positions. In some cases the comparison window may comprise at most 10, 20, 50, 100, 200, 300, 400, 500, or 600 positions. In some cases the comparison window may comprise at least 50 to 200 positions, or at least 100 to at least 150 positions in which a sequence may be compared to a reference sequence of the same number of contiguous or non contiguous positions after the two sequences are optimally aligned. Methods of alignment of sequences for comparison are well-known in the art. Optimal alignment of sequences for comparison can be conducted, e.g., by the local homology algorithm of Smith and Waterman, Adv. Appl. Math. 2:482 (1981), by the homology alignment algorithm of Needleman and Wunsch, J. Mol. Biol. 48:443 (1970), by the search for similarity method of Pearson and Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al, eds. 1995 supplement)).

In some cases, a comparison window may comprise any subset of the total alignment, either contiguous positions in primary sequence, adjacent positions in tertiary space but discontinuous in the primary sequence, or any other subset of 1 up to all residues in the alignment.

As used herein, the term "vaccine" is meant to encompass any immunogenic composition that is capable of inducing an immune response in a subject. The vaccine can include one or more immunogenic composition, e.g., any primary immunogenic composition together with a secondary immunogenic composition. Immune response may include responses that result in at least some level of immunity in the subject to which the immunogenic composition is administered.

As used herein, the term "immunogenic composition" is any substance, formulation or organism that provokes an immune response (produces immunity) when contacted with an immune cell. In some cases, immunogenic compositions encompass all substances or formulations that can be recognized by the adaptive, humoral or innate immune system when administered to a host animal or subject. In some cases, immunogenic compositions are those substances that elicit a response from the immune system.

As used herein, the term "intermediate antibodies" define antibodies (including B cell associated antibodies, i.e., BCRs) with zero to intermediate somatic mutational diversification on the maturational pathway of an antibody from a germline antibody to a maturated antibody. An intermediate antibody can have zero or more mutated amino acid residues compared to the germline antibody but has fewer mutated residues compared to the mature antibody. Analysis of somatic hypermutations can be performed by classifying to the closest V-gene and J-gene by VDJFasta algorithm or any other sequence classifier, aligning the sequence to its germline counterparts using the VDJFasta algorithm or any other sequence alignment algorithm, and then taking the percent identity of the alignment. The intermediate antibody may have between 0% to 95%, of the mutations of the corresponding mature antibody. In some cases the intermediate antibody has at least 0%, 1%, 2%, 3%, 4%, 5%, 6%, 7%, 8%, 9%, 10%, 15%, 25%, 30%, 35%, 40%/a, 45%, 50%, 55%, 60%, 65%, 70%, 75%, 80%, 85%, or 90% of the mutations of the corresponding mature antibody. In some cases the intermediate antibody has at most 1%, 2%, 3%, 4%, 5%, 6%, 7%, 8%, 9%, 10%, 15%, 25%, 30%, 35%, 40%, 45%, 50%, 55%, 60%, 65%, 70%, 75%, 80%, 85%, or 90% of the mutations of the corresponding mature antibody.

The term "in vitro translation system", which is used herein interchangeably with the term "cell-free translation system" refers to a translation system which is a cell-free extract containing at least the minimum elements necessary for translation of an RNA molecule into a protein. An in vitro translation system may comprise at least ribosomes, tR As, initiator methionyl-tRNA$^{Met}$, proteins or complexes involved in translation, e.g., eIF2, eIF3, the cap-binding (CB) complex, comprising the cap-binding protein (CBP) and eukaryotic initiation factor 4F (eIF4F).

The term "somatic mutational diversification (SMD)" is a measure of the number of mutated amino acid residues compared to the germline and is a consequence of the natural B cell diversification processes, including affinity maturational processes in which the B cell undergoes hypermutation in a germinal center in the presence of an antigen. It is expressed as the percentage of that number compared to the total number of amino acid residues in the sequences. Generally, the number of amino acids encoded by the VH gene is used to measure the SMD because usually the heavy chain variable region is a major determinant of the antibody specificity and the VH gene encodes most of the amino acid residues of the heavy chain variable region. Sometimes, the VL gene can also be used to analyze SMD.

III. Immunogenic Composition Design: Epitope Selection and Generation of Antigenic Variant Ensembles A. Antigen Structural Analysis The composition and methods of the disclosure first provide for a design process involving the structural analysis, (200) of one or more target antigen proteins as shown in FIG. 2. Generally, a three dimensional structure, structural representative or structural model is first obtained of a target antigen and analyzed for potential epitopes against which an antibody may be raised. In some case, a target epitope may be chosen based on the presence of known or predicted neutralizing antibodies that may selectively bind to the target epitope. In some cases, an antigen may be a single protein of interest or a complex of two or more proteins. In some cases an antigen may refer to an antigen domain, or a region or section of a larger protein or protein complex. In some cases an antigen may be a fragment of a protein or a polypeptide sequence. Generally, an antigen selected for structural analysis may be any polypeptide sequence or glycoprotein.

An antigen can be an intact (i.e., an entire or whole) antigen, or a functional portion of an antigen that comprises one or more epitopes. An antigen may be a peptide functional portion of an antigen. "Intact" refers to full length antigen as that antigen polypeptide occurs in nature. An intact antigen may adopt the native protein fold as seen in nature, presenting both primary sequence epitopes as well as tertiary sequence conformational epitopes. This is in direct contrast to delivery of only a small portion or peptide of the antigen. Delivering an intact antigen to a cell may elicit an immune response to a full range of epitopes of the intact antigen, rather than just a single or selected few peptide epitopes.

Alternatively, an intact antigen can be divided into many parts, depending on the size of the initial antigen. Typically, where a whole antigen is a multimer polypeptide, the whole protein can be divided into sub-units and/or domains where each individual subunit or domain of the antigen can be associated with the polymer according to the methods as disclosed herein. Alternatively, in some cases, an intact antigen can be divided into functional fragments, or parts, of the whole antigen, for example, at least 2, 3, 4, 5, 6, 7, 8, 9, 10, 11, 12, 13, 14 15, 16, 17, 18, 19, 20, 21, 22, 23, 24, 25, 30, 35, 40, 45, 50, 55, 60, 65, 70, 75, 80, 85, 90, 95 Or 100 portions (e.g., pieces or fragments), inclusive, and where each individual functional fragment of the antigen can be associated with the polymer according to the methods as disclosed herein. In some cases the antigen may be divided into at most 2, 3, 4, 5, 6, 7, 8, 9, 10, 11, 12, 13, 14 15, 16, 17, 18, 19, 20, 21, 22, 23, 24, 25, 30, 35, 40, 45, 50, 55, 60, 65, 70, 75, 80, 85, 90, 95 Or 100 portions (e.g., pieces or fragments), inclusive.

The fragmentation or division of a full length antigen polypeptide can be an equal division of the full length antigen polypeptide, or alternatively, in some cases, the fragmentation may be asymmetrical or unequal. Any combination of overlapping fragments of a full length whole antigen may be used in the generation of subsequent antigen library as described herein.

In some cases, an antigen may be selected for structural analysis based on the availability of one or more three dimensional structures or models available for the protein. In some cases, structures or structural models may not be available for a particular antigen. Available structures may include any suitable structures, as solved by a variety of techniques known in the art, including but not limited to X-ray crystallography (i.e. crystal structure), nuclear magnetic resonance (NMR), small angle X-ray diffraction (SAX), cryo-electron microscopy, electron microscopy or in silico modeling methods, such as threading or homology modeling. Generally, one or more protein structures may be obtained via any suitable database, including but not limited to databases such as the publicly available Protein Data Bank (PDB) or the Molecular Modeling Database (MMDB). Structures could also be generated using any other known techniques in the art.

In some cases, an experimental protein structure may not be available. In some cases a structural model or representative may be used. If the exact crystal structure of a particular antigen is not known, but its protein sequence is similar or homologous to another known sequence with a known crystal structure, a homology model may be generated and used with the compositions and methods of this disclosure. Structural models can be generated using Modeller (N. Eswar, M. A. Marti-Renom, B. Webb, M. S. Madhusudhan, D. Eramian, M. Shen, U. Pieper, A. Sali. Comparative Protein Structure Modeling With MODELLER. Current Protocols in Bioinformatics, John Wiley & Sons, Inc., Supplement 15, 5.6.1-5.6.30, 200). Appropriate structural modeling templates can be identified by creating a profile Hidden Markov Model (HMM) of the reference sequences using HMMer (*Profile Hidden Markov Models*. S.

R. Eddy. Bioinformatics, 14:755-763, 1998), and then using the HMM to search for homologous scaffolds in PDB with a minimum expectation value (e-value) of at $1\times10^{-3}$. In some cases, the e-value may be at least, $1\times10^{-1}$, $1\times10^{-2}$, $1\times10^{-3}$, $1\times10^{-4}$, $1\times10^{-5}$, $1\times10^{-6}$. In some cases, the e-value may be at most, $1\times10^{-1}$, $1\times10^{-2}$, $1\times10^{-3}$, $1\times10^{-4}$, $1\times10^{-5}$, $1\times10^{-6}$. In such instances, it is expected that the conformation of the particular antigen may be similar to the known crystal structure of a homologous protein. The known structure may, therefore, be used as the reference structure for all variants of the target antigen, or in some cases, may be used to predict the structure of the target antigen (i.e., in "homology modeling" or "molecular modeling").

The resolution of protein structures for a selected antigen may range from IA to 100 Å. In some cases, protein structures for a selected antigen may range from 1 Å to 6 Å. In some cases protein structures for a selected antigen may range from IA to 3 Å, 2 Å to 4 Å, 3 Å to 6 Å, or 4 Å to 6 Å. In some cases, a protein structure or structural model may be at least 1 Å, 2 Å, 3 Å, 4 Å, 5 Å, 6 Å, 7 Å, 8 Å, 9 Å, 10 Å, 15 Å, 20 Å, 25 Å, 30 Å, 35 Å, 40 Å, 45 Å, 50 Å, 60 Å, 70 Å, 80 Å, 90 Å, or 100 Å. In some cases a protein structure or structural model may be at most IA, 2 Å, 3 Å, 4 Å, 5 Å, 6 Å, 7 Å, 8 Å, 9 Å, 10 Å, 15 Å, 20 Å, 25 Å, 30 Å, 35 Å, 40 Å, 45 Å, 50 Å, 60 Å, 70 Å, 80 Å, 90 Å, or 100 Å.

One or more antigen proteins may also be selected based on other factors, such as size, shape, complexity, ability to elicit broadly neutralizing antibodies, biological relevance for an immunogenic composition or the degree of characterization as known in the art. In yet other cases, an antigen may be selected based on known antibodies that may bind one or more epitopes on the protein.

For example, an antigen may range from 5 KD-1000 KD in size, as single protein or a complex of proteins. In some cases, an antigen may be at least 5, 10, 15, 20, 30, 40, 50, 60, 70, 80, 90, 100, 200, 300, 400, 500, 600, 700, 800, 900 or 1000 KD in size. In some cases, an antigen may be at most 5, 10, 15, 20, 30, 40, 50, 60, 70, 80, 90, 100, 200, 300, 400, 500, 600, 700, 800, 900 or 1000 KD in size.

For example, an antigen may range from 50 amino acids to—100,000 amino acids in size, as a single protein or a complex of proteins. In some cases, an antigen may be at least 50, 100, 200, 300, 400, 500, 600, 700, 800, 900, 1000, 5000, 10000, 20000, 30000, 40000, 50000, 60000, 70000, 80000, 90000, or 100000 amino acids in size. In some cases, an antigen may be at most 50, 100, 200, 300, 400, 500, 600, 700, 800, 900, 1000, 5000, 10000, 20000, 30000, 40000, 50000, 60000, 70000, 80000, 90000, or 100000 amino acids in size. In some cases, an antigen is at least 100 amino acids in length. In some cases an antigen is a minimal number of amino acids comprising a protein fold.

In the case of biological relevance for vaccine for example, an antigen may be selected based on the amount of antigen expressed by a particular pathogen, or how well the antigen may be exposed to immune cells in a host animal. Examples may include but are not limited to viral capsid proteins, surface receptors of cancer cells or parasites, transemembrane proteins of pathogens, secreted toxins, soluble growth factors and the like. Generally any protein may be selected as an antigen.

Suitable antigen proteins may include but are not limited to ligands, cell surface receptors, cytokines, hormones, transcription factors, signaling molecules, cytoskeletal proteins, virulence factors, viral proteins, bacterial proteins, proteins from pathogens and enzymes. Suitable classes of enzymes include, but are not limited to, hydrolases such as proteases, carbohydrases, lipases; isomerases such as racemases, epimerases, tautomerases, or mutases; transferases, kinases, oxidoreductases, and phophatases. Suitable enzymes may be listed in the Swiss-Prot enzyme database. Suitable antigens may include, but are not limited to, all of those found in the protein data base compiled and serviced by the Research Collaboratory for Structural Bioinformatics (RCSB, formerly the Brookhaven National Lab).

In some cases, an antigen may be selected, such that the antigen is not expressed by a known pathogen. For example, in applications relating to the development of antibody based tools, any protein may be designated an antigen, whereby an antibody raised against an epitope on the protein is desired.

After one or more protein structures or structural models are obtained, the structure is analyzed using any suitable algorithm that may be used to estimate geometric relationships, such as distance, between individual residues in the antigen. In the three dimensional folding of a protein, amino acid residues, not found adjacent sequentially in the primary sequence may be proximal to one another spatially. Generally, a suitable algorithm provides for estimating the geometric relationship, such as distance between residues defined by Cartesian coordinates. For example, one such distance geometry program, DGEOM, is a distance geometry program for molecular model-building and conformational analysis available from Chiron Corporation of Emeryville, Calif. Havel, et al. *J Theor Biol.* 104:359-81 (1983); Havel et al. *J Theor Biol.* 104:383-400 (1983). Another such tool is Modeller (N. Eswar, M. A. Marti-Renom, B. Webb, M. S. Madhusudhan, D. Eramian, M. Shen, U. Pieper, A. Sali. Comparative Protein Structure Modeling With MODELLER Current Protocols in Bioinformatics, John Wiley & Sons, Inc., Supplement 15, 5.6.1-5.6.30, 200), in which both structural proximity as well as percent surface accessibility can be calculated. Molecular structures can be described by the set of all pairs of interatomic distances produced using physical constraints of the protein structure. Distance measures between residues can also be obtained directly from the PDB file by reading it using BioPerl, BioPython, or any other bioinformatics framework.

For example, to identify all residues in a hypothetical epitope in a HA protein centered around residue S100, a PDB model of HA may be accessed using the bioinformatic program BioPerl in which a list of every residue with a carbon alpha backbone position less than 25 Angstroms from the carbon alpha backbone position of S100 is generated.

Further, antigen structural analysis may also provide information relating to which residues of the protein may be more surface exposed than others, some of which may be buried in the interior of the protein. In some cases, certain algorithms may provide a score for the relative "exposure" of each residue in a protein structure or model. This can be performed with Modeller (N. Eswar, M. A. Marti-Renom, B. Webb, M. S. Madhusudhan, D. Eramian, M. Shen, U. Pieper, A. Sali. Comparative Protein Structure Modeling With MODELLER. Current Protocols in Bioinformatics, John Wiley & Sons, Inc., Supplement 15, 5.6.1-5.6.30, 200).

In some cases, certain residues are readily exposed to the outside environment. In some cases, certain residues are partially buried in the three dimensional folds of the protein. In other cases, certain residues, such as highly hydrophobic amino acids, are completely buried in the interior core of the protein. Given that immunogenic B-cell epitopes are generally comprised of residues that are readily available or exposed to a an immune receptor B cell receptor (BCR), residues that are identified as highly exposed to the exterior of the protein and found proximal one another, may be selected as part of one or more potential epitopes of the antigen in subsequent steps (C. Epitope mapping) and described further herein. In other cases, MHC-dependent epitopes displayed to T cell receptor (TCR) may not be found in surface exposed regions and can be found anywhere in the protein. In some cases, epitopes may be derived from region of the protein that are not surface exposed.

B. Antigen Homolog Alignment

Generally, after initial antigen structural analysis, one or more sequences, homologous to the primary sequence of the target antigen may be aligned and compared, (201). This step may be used to improve selection of functional variation of the protein, as determined by subsequent steps (Surface Heterogeneity Optimization). A variety of computational methods and strategies may be employed to align sequences and compare three dimensional structures of the proteins sequences. In some cases, protein structures are available for variety of homologous antigens or antigen variants. For example, for certain antigens such as HA protein or the HIV gp120 protein, numerous crystal structures have been solved for various mutation substitutions or variants, and many (e.g. thousands) of sequences are available in public databases, such as public influenza databases. In some cases these variants have been experimentally constructed (e.g. selected residues of recombinant protein have been purposely mutated and the structure of the mutated protein solved), while in other cases these variants may exist in nature (e.g as a result of genetic variation in different strains of a virus). In this step of the composition and methods of the disclosure, any protein structures or models of relevant homologs may be aligned and compared. In some cases, each homolog may contribute additional information to variation observed to be tolerated on the native fold, and to identify variation never observed. In some cases, variation derived from natural variation may be used to identify amino acid positions suitable for further diverisification or amino acids positions that do not tolerate variation and and may be avoided during diversification in subsequent steps described herein.

In some cases, sequences that may be homologous to the target antigen or target antigen domain with a known or predicted structure may share at least 25%, 30%, 45%, 50%, 60%, 65%, 70%, 75%, 80%, 85%, 90%, 95%, 96%, 97%, 98%, 99%, 99.9%, 99.99% or 99.999% identity as described herein. In some cases, the sequences homologous to the target antigen or target antigen domain with a known or predicted structure share at most 25%, 30%, 45%, 50%, 60%, 65%, 70%, 75%, 80%, 85%, 90%, 95%, 96%, 97%, 98%, 99%, 99.9%, 99.99% or 99.999% identity. Percent identity may be determined or calculated using a variety of computational techniques as described herein. For example, homology can be calculated using the NCBI standard BLASTp programs for protein using default conditions, in regions aligned together (without insertions or deletions in either of the two sequences being compared) including all residues for the sequences compared.

In certain cases, insertions or deletions or "gapped" sequences may be disregarded. For example, the *Thermus Aquaticus* Phenylalanyl tRNA Synthetase alpha subunit appears to have an "insert" region from residues 156 to 165 when compared to its homologs from other species. This region can be disregarded in calculating sequence identity.

Percent identity may be calculating using any suitable methods, including but not limited to creating a profile Hidden Markov Model of a reference sequence using HMMer (*Profile Hidden Markov Models*. S. R. Eddy. *Bioinformatics,* 14:755-763, 1998), and then using the HMM to search for homologous scaffolds in PDB for homology with a minimum expectation (e-value) or threshold. In some cases, the e-value may be at least, $1\times10^{-1}$, $1\times10^{-2}$, $1\times10^{-3}$, $1\times10^{-4}$, $1\times10^{-5}$, or $1\times10^{-6}$. In some cases, the e-value may be at most, $1\times10^{-1}$, $1\times10^{-2}$, $1\times10^{-3}$, $1\times10^{-4}$, $1\times10^{-5}$, or $1\times10^{-6}$. Other programs that may provide similar calcuations include MUSCLE, or mafft.

Alternatively, in some cases, the compositions and methods of the disclosure also provide for comparison of homologous domains of particular proteins. For example, while the overall percent identity of two or more proteins may be less than 50%, certain regions of the proteins, such as one or more domains, might be used for sequence alignment. In this case, an epitope may be selected from a desired domain homologous to the proteins and sequences aligned and compared.

Generally, antigen homologs may be compared from known antigen variants, or by variants generated or predicted computationally. In some cases, mutations or variations made to the target antigen sequence may yield a protein that does not have a structure solved by experimentation. In many cases, a variety of techniques may be used to model the predicted structure of these variants or homologs. In some cases, modeled structures may use a reference. In some cases modeled structures may be reference-free.

Generally, any of the many methods of model generation can be applied at this step in the over-all methodology. The alignment methods described herein are provided only for example. Other methods may be used to deduce structures that are consistent with distance and general model constraints. Two strategies that may be particularly useful with the compositions and methods of the disclosure are constrained threading and constrained sequence/structure alignment. Other possible methods include but are not limited to dynamic programming and clique detection.

For example, constrained threading is a general computational strategy to generate models by threading a sequence through a database of sequence-unique protein folds. Various software programs are available in the art to generate such models. For example, the publically available algorithm provided by Alexandrov et al. "Fast Protein Fold Recognition via Sequence to Structure Alignment and Contact Capacity Potentials." Protein Science Bulletin. (1996), incorporated by reference herein, may be used. This program involves entering the sequence of the protein, determining the alignment mode and allowing the software algorithm to generate the model. In global alignments, all positions are considered. In free shift alignments gaps at the beginning or at the end are not scored. Local alignments may be maximal common substring alignments. For any of these alignment modes, the program may provide a given number of top scoring alignments.

Various models may be generated for a single homolog and evaluated using various constraints and parameters. Parameters such as total constraint error, the number of distance constraints, the pairwise distance separation, and the pairwise distance as defined by the structure or reference for the two residues in a constraint may be used to evaluate the most useful models.

Other programs or algorithms may be used in homolog alignment. In some cases, one or more algorithms may use an overall stepped process such as threading. In this case, the primary sequence of the protein being analyzed is threaded through each selected protein structure. For example, the backbone of the antigen homolog under consideration is laid on top of a backbone for the currently selected target antigen. After the homolog under consideration has been aligned with a selected protein such as the structure of the target antigen, the selected protein is scored. In some cases a score based on (1) sequence identity between the two proteins, (2) alignment of secondary structures between the two proteins, and (3) a contact capacity potential of the protein in its threaded format. The second scoring criterion may involve approximating secondary structures of the protein based on the primary sequence. The third scoring criterion may be based on the how closely the local environment (neighboring amino acids) of an amino acid residue matches with its empirically-determined preferred environment. Other software programs and other scoring criteria (e.g., hydrophobicity, potential mean force) can be used.

Residues of selected models may be subsequently converted into three dimensional coordinates by a computer program such as DGEOM, as described herein, and compared to the target antigen structure.

Another computational strategy for antigen homolog alignment may comprise constrained sequence/structure alignment. This approach employs the constraints to first build a set of structural models, and then evaluate models by applying a pairwise hydrophobic contact potential to each model, and rank-ordering models based on this potential function. An algorithm as provided by Bryant et al. "An Empirical Energy Function for Threading Protein Sequence Through the Folding Motif," *Proteins.* 1993 16 92-112, incorporated by reference in its entirety herein, may be used. In this approach, alignments to the fold may be defined by systematically matching residues of the target protein or antigen linked by a restraint to residues of the fold for which the interatomic distance of the alpha carbons is less than the extended crosslinker plus side chain atoms (<23.85 Angstroms in the case of the BS3 linkers).

The protein sequence can then be mapped onto the fold working back from the first-matched residue to the first residue of the sequence, or to the first of the fold, forward from-the first matched residue and back from the second in a symmetrical fashion, and forward from the second matched residue. Alignments can be scored using the pairwise hydrophobic contact potential defined by Bryant et al., 1993, and the best score obtained for each fold was retained to rank the fold.

In both model generation approaches, the model most complementary to known constraints and/or experimental parameters may be selected for the construction of a homology model. The threading alignment can be used to match amino acids in the sequence to positions in the structure. Other alignment protocols could be used as well. The model can then be constructed using standard homology modeling techniques. Additionally, distance constraint violations within the model may assist in further refinement of the model. Refinement of the model can be done using distance geometry, energy minimization, and/or molecular dynamics.

Any of the techniques, or combination of techniques as described herein may be used to generated predicted structural models for antigen homolog alignment.

In some cases, master-slave modeling may be used in alignment of structures, whereby a pivot (master) structure may be aligned to all other structures (slaves) to it based on pairwise alignments. If there is any error or inconsistency in the master-slave alignments, the final multiple structural superposition and alignment may be erroneous. One such program, CE-MC (Guda et al., 2001) may be used whereby a subsequent Monte Carlo step to increase the number of aligned columns and correct errors. Another widely used technique is the progressive approach (PAL) (Yang and Honig, 2000; Ye and Godzik, 2005 and may be used with the compositions and methods of this disclosure. Positions in the model may be then mapped the alignment for all members and then to the profile of the hiden markov model coordinates of the design.

As described herein, structural models generated computationally, or synthetically, may be performed for a range of homologs. In some cases, 1-1,000,000 homologs may be generated or obtained and structurally aligned to the target antigen. In some cases at least 1, 10, 100, 500, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, or 1000000 different homologous structures of antigen variants may be computationally generated or obtained and compared to the target antigen. In some cases at most 1, 10, 100, 500, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, or 1000000 different homologous structures of antigen variants may be computationally generated or obtained and compared to the target antigen. All or part of the collection of homologs generated may be compared for further analysis.

C. Epitope Identification and Selection

After one or more homologous antigen structures have been generated or obtained, multiple structures may be compared spatially to identify and select a target epitope on the target antigen, (202). In some cases, a target epitope is a patch of structurally proximal, surface exposed residues on the antigen, such as for an epitope for BCRs. In some cases, an epitope is a patch of adjacent residues found anywhere in the protein, such as in surface exposed, or non surface exposed regions of the antigen. Non surface exposed epitopes may be used to select epitopes for T-cell receptors (TCRs). In some cases, when a known antibody, such as a neutralizing antibody, has been previously characterized, one or more target epitopes on an antigen surface may refer to all unique combinations of residues where the maximum solvent exposed surface circumference distance in A between any two members is less than or equal to the maximum distance between an antigen residues observed in known antibody-antigen contacts from published structures. In this case, information regarding the specific spatial binding position of an antibody to a target epitope may be determined experimentally or be publically available. Co-crystallization, high resolution cryo-EM, or NMR of an antibody or antibody fragment bound to a target epitope on an antigen may provide this experimental information. Antibody epitopes may range from 100 $Å^2$ to 1500 $Å^2$ as described herein.

Alternatively, information for a given target epitope and antibody may not be known. In some cases, a target epitope may refer to all combinations observed by in-silico protein-protein docking of multiple antibody models against the target epitope on the target antigen. In some cases, a target epitope across two homologs of the antigen protein may be scored as function of target epitope percent identity. Percent identity may be calculated as the following: Target Epitope Percent Identity=((Residues in Target Epitope)−(Hamming Distance between Target Epitopes in Homologs))/(Residues in Target Epitope). In some case Target Epitope average similarity may be calculated as the following: Target Epitope average similarity=Σ (BLOSUM62 similiarity score between all homologous positions)/Residues in Epitope).

In some cases, no previous known information regarding antibody-epitope binding interactions may be previously known, whereby in silico docking may be limited or unable to be performed. In some cases, a target epitope may be selected de novo from the structural comparisons of sequence homologs. In some cases, structural comparison of variants may provide information regarding the identification of conserved surface exposed residues in an antigen. Antigens, for which there are numerous variants found in nature, such as viral proteins, may be particularly useful. In other cases, in silico model generation may provide some predicative information regarding surface residues that must remain conserved for stability of the protein. In some cases, conserved surface residues of a particular antigen may be determined experimentally, or as known in the art. A protein map comprising multiple aligned structures of one or more homologs and the target antigen may be generated. A structural comparison map may be useful for determining which residues may comprise an epitope (a related by geometric distances) and which of these epitopes may be most highly conserved.

In one example, this strategy may be particularly useful in the design of a functional vaccine. In the example of viral protein such as HA protein, the influenza virus may be able to mutate to evade multiple antibodies generated to epitopes that are prone to mutation. Slight changes to the genome of the virus translate to differences in the residues of the protein. These changes may cause the virus to escape immune recognition. This step of the composition and methods of the disclosure may allow for the identification of surfaces of "broadly neutralizing epitopes" in the antigen protein that may be resistant to such changes. Identification and ultimate selection of these areas for target epitopes to which an antibody may be raised, may decrease the likelihood of viral evasion of antibodies through mutation or antigenic drift in a host or subject. Epitope selection and strategies for vaccine development are further described herein.

D. Surface Heterogeneity Optimization

After a target epitope is identified and/or selected, another algorithm is used to generate a population or library of antigenic variants that 1) maintain the three dimensional conformation and spatial specificity of the target epitope, while 2) varying the sequence composition and spatial specificity of the protein surface surrounding the target epitope, (203). The methods and compositions of the disclosure provide for the generation of an immunogenic composition comprising two or more antigen variants, whereby the effective concentration of a target epitope common to all antigen variants is higher than the concentration of any additional surface features or regions of the antigen surrounding the target epitope. In effect, this step may help to diversify the antigen regions surrounding the target epitope such that the diversity decreases the effective concentration of non-target epitope surface. This strategy may produce a focused immune response to the desired target epitope, while avoiding an immune response to undesired regions of the antigen (i.e. non target epitope surfaces of the protein).

The compositions and methods of the disclosure provide for a general computational strategy for surface heterogeneity optimization of multiple antigenic variants or members. In some cases, an "inverse protein folding" strategy may be used for optimization of amino acid sequences in non-target epitope surfaces of the protein. Similar to protein design, such approach seeks to find a sequence or set of sequences that will fold into a desired structure. Antigenic members, each containing a conserved target epitope, may still fold in a similar fashion as the target antigen. In some cases similar folds between the target antigen and antigenic members is desired. In some cases, the similarity of folds between antigenic variants and the target antigen may aid in the correct presentation of the native target epitope. Unlike alternative approaches in vaccine development, whereby target epitopes, such as a peptide or protein domain may be isolated out of context of the full protein as a lineage peptide or fused to additional sequences, the target epitope is conserved across a plurality of antigenic members and may be exposed to the exterior of the protein in a conformation similar to the conformation as found in the original target antigen. In some cases, presentation of the epitope in conformations similar to the epitope's native conformation may increase the likelihood of strong and targeted immune response to the natural or native target epitope.

In a generalized approach, non target epitope residue positions that are selected for heterogeneity optimization may be determined based various criteria. Information related to relative sequence conservation or predicted protein stability models may indicate which residues may be easier to change and optimize than others. During optimization and generation of antigen variants, changes in sequence in non-target epitope regions may be selected to have minimal impact on the conformation of the target epitope region of the antigen and the general folds of the antigen. In some cases, residues that have the least impact may be more prone for selection and change during the optimization process. In some cases, changes to a combination of residues may have an impact or little impact on the target epitope region. The general strategy of the algorithm is optimization of maximal change to non target epitope regions of the antigen variants, wherein the antigen variant still adopts a similar protein fold of the target antigen, and the target epitope remains spatially conserved between the antigen variant and the original target antigen. In some cases, maximal change is reflected by maximal decrease in percent identity of comparable non target epitope regions between antigenic variants.

In some cases, a set of homologs may be diversified in the non target epitope regions by first generating a positional weight matrix for all positions in the antigen sequence. As described herein, antigen homolog sequences may be first selected and aligned, such as with the program MUSCLE. Probability scores from the alignment may then be used to generate a probabilistic, statistical or stochastic model for subsequent analysis of individual amino acid positions in the sequence. Generally, any suitable model may be used. For example, hidden markov, dynamic programming, support vector machine, Bayesian network, trellis decoding, Viterbi decoding, expectation maximization, Kalman filtering, or neural network methodologies may be used. Various suitable programs may be used to generate these models. For example, as described herein, the program HMMer may be used to generate a hidden markov model (HMM). The HMM may be used to search any database, such as PDB for homolog structures or models. One or more structural models may then be aligned using the HMM derived for each sequence.

After the structural models have been aligned, a positional weight matrix (PWM) may be extracted from the HMM. Generally a positional weight is a matrix of score values that gives a weighted match to any given substring of fixed length. It has one row for each symbol of the alphabet, and one column for each position in the sequence. The score assigned by a PWM to a substring $s=(s_j)_{j=1}^{N}$ is defined as $\sum_{j=1}^{N} m_{s_j,j}$, where j represents position in the substring, $s_j$ is the symbol at position j in the substring, and $m_{\alpha,j}$ is the score in row α, column j of the matrix. In some cases, a PWM score is the sum of position-specific scores for each symbol in the substring. In some cases, the PWM can be interpreted as the identity and frequency of amino acids permitted at each structurally conserved position in all known variants of the antigen.

Using a PWM, each position in the structure may be mapped to a position in the alignment, correlating a column in the HMM, and a column in the PWM. Further, amino acids identified as surface exposed, as described herein, may be mapped to each column in the PWM from the structure (e.g as provided by a program such as Modeller).

Further, identified epitopes, as described herein may be mapped to the PWM. In some cases, epitopes are known in the art for a particular antigen or protein. In some cases, an epitope is chosen for a particular antigen or protein as described herein. In some cases, non-exposed residues may be assigned as reference sequence and may be excluded from diversivication. In some cases, non surface exposed residues or epitopes may be computationally masked to prevent diversification. With this strategy, non exposed residues, or residues found in the core of the protein may be conserved, while exposed residues outside the target epitope region are diversified.

Diversification of non-target epitope surface exposed sequences may be performed by manipulating diversity frequencies in the remainder of the positions that are surface exposed and not part of target epitopes. Using computation-guided simulations, individual amino acid positions may be diversified by substituting a different amino acid residue for each position, in silico. Diversification of each position provides for the generation of sequences that may then be further tested and analyzed.

For example, a collection of $1\times10^6$ sequences can be sampled from the PWM design in-silico by bioinformatics simulation and analyzed. If the sequences are either so similar to one another that they contain many off-target epitopes in common, or so distant from the reference structure that they have a low probability of folding, the PWM may be altered and retested to generate additional sequences.

Optimization or altering of the PWM may be performed by techniques such as linear scaling of non-dominant amino acid frequencies compared to dominant amino acid frequencies at each position. Testing of molecules may comprise observing identity across one or more antigens. In some cases, antigen variant molecules may be at least 25%, 30%, 35%, 40%, 45%, 50%, 55%, 60%, 65%, 70%, 75%, 80%, 85%, or 90% identical identical to a known reference sequence. In some cases, antigen variant molecules may be at least 25%, 30%, 35%, 40%, 45%, 50%, 55%, 60%, 65%, 70%, 75%, 80%, 85%, or 90% identical. In some cases, percent identity of one antigen to another may reflect homology. In some cases, percent identity of one antigen to another may reflect the likelihood of antigen sequences generated from the PWM to maintain the protein fold of the reference sequence. Generally any percent identity between antigens may be accepted, provided the protein fold of the antigen is conserved in one or more antigen variants generated by the PWM for the library.

Further, testing comprises observing percent identity of a plurality of non target epitopes, defined as any collection of surface exposed residues within a defined area centered on the carbon alpha backbone of a residue also on the surface. In some cases, the area is at least 25 $Å^2$, 50 $Å^2$, 100 $Å^2$, 200 $Å^2$, 300 $Å^2$, 400 $Å^2$ or 500 $Å^2$, 600 $Å^2$, 700 $Å^2$, 800 $Å^2$, 900 $Å^2$, 1000 $Å^2$, 1200 $Å^2$, 1500 $Å^2$, or 2000 $Å^2$. In some cases, the area is at most 25 $Å^2$, 50 $Å^2$, 100 $Å^2$, 200 $Å^2$, 300 $Å^2$, 400 $Å^2$ or 500 $Å^2$, 600 $Å^2$, 700 $Å^2$, 800 $Å^2$, 900 $Å^2$, 1000 $Å^2$, 1200 $Å^2$, 1500 $Å^2$, or 2000 $Å^2$. In some cases, the epitope area is 25-100 $Å^2$. In some cases, the epitope area is 100-200 $Å^2$. In some cases, the epitope area is 200-300 $Å^2$. In some cases, the epitope area is 300-400 $Å^2$. In some cases, the epitope area is 400-500 $Å^2$.

Generally, the percent identity of non target epitopes may be compared pairwise between antigen variants generated by the PWM. For example, a certain residue position may be chosen in the antigen and one or more antigen variants. A residue may also be chosen between different antigen variants. Percent identity of all residues within a defined area, such as 25 $Å^2$ around the chosen residue, may be compared and percent identity calculated. The non target epitope area may be described by any suitable geometric shape, including but not limited to an oval, disc, circle, square, triangle, rectangle, star, polygon and the like. In some cases, the area is defined by an oval shape.

The percent identities of a plurality of non target epitope areas may be compared in a pairwise analysis. In some cases percent identity greater than 90% of a commonly defined area between antigen variants may indicate the antigen variants may be too similar in those non target epitope regions. In some cases, non target epitope regions or areas may be at at least 0%, 10%, 20%, 30%, 40%, 50%, 60%, 70%, 80% or 90% identical. In some cases, non target epitope regions or areas may be at at most 0%, 10%, 20%, 30%, 40%, 50%, 60%, 70%, 80% or 90% identical.

Figure 5:
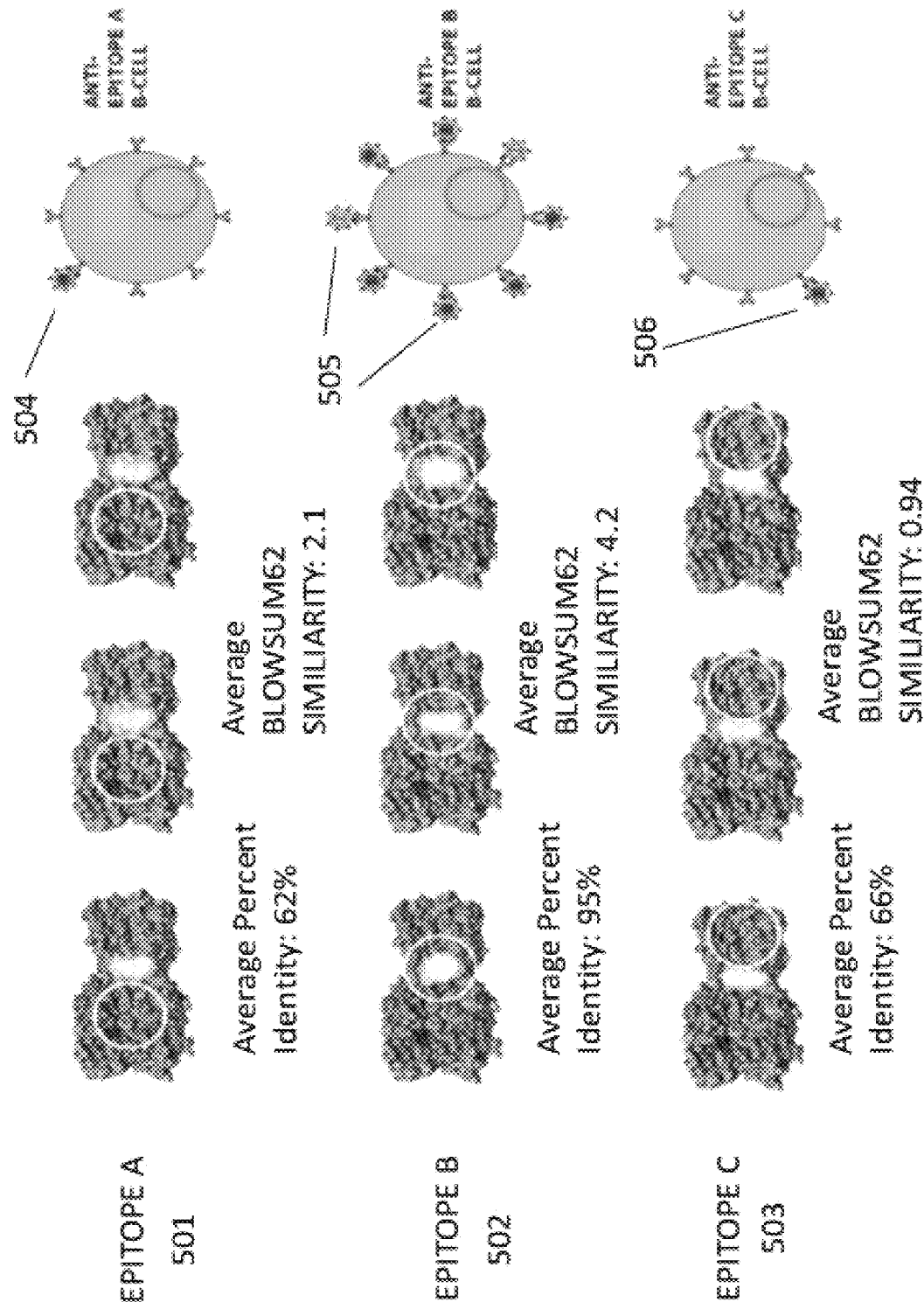
FIG. 5 is a schematic representation of 3 epitopes of the same target protein, and varying sequence identities of the 3 epitopes between antigens variants of the target protein.

For example, for a given protein as shown in FIG. 5, multiple epitopes are found on the surface of a target antigen. In this example, 3 epitopes are shown, epitope A, (501), epitope B, (502), and epitope C, (503) for different antigen variants. In this example, epitope B is chosen as the target epitope, while epitopes A and C are chosen for diversification. As described herein, diversification yields changes in percent identity of non-target epitopes across antigen variants of an immunogenic composition. Using a commonly defined oval area of 100 $Å^2$, percent identity may be calculated for each epitope (A, B, C) across each of the antigen variants. The commonly defined area may be centered around a particular residue within the epitope or area adjacent to the epitope. In the case of epitope A, a non target epitope region, the average percent identity is determined to be 62% in this example. Similarly, for epitope C, another non epitope region, the average percent identity is determined to be 66% in this example. For the target epitope region, epitope B, the epitope is common to all antigen variants and has an average percent identity of 95%. Given the relative difference between the percent identity of epitope B and epitopes A and C, epitope B is considered conserved between the antigen variants.

Further, the cartoon diagrams as shown in FIG. 5, indicates a simplified model of BCR recognition of epitopes A, B and C. When combined together, the 3 antigen variants of this example immunogenic composition present different effective concentrations of epitopes A, B and C. Given the diversification of epitopes A and C across the 3 epitopes, BCR recognition of either epitope A (504) or recognition of epitope C (506) is relatively low, as indicated by binding of only one molecule by either B cell. However, the effective concentration of epitope B, due to its conservation (high percent identity) across all antigen variants in the immunogenic composition is higher than for A or C. Thus BCR recognition may be higher for epitope B, (505) as indicated by the binding of multiple antigens by the B cell. This differential recognition of epitopes based on differences in effective concentration provides for eliciting an immune response selectively to the target epitope.

In some cases, if sequence generated by the PWM fails to meet a threshold as described herein, the PWM may be altered to be either more or less diverse. As an alternative to PWM-library optimization, a human user could manually design and test variant sequences.

As an alternative to linear scaling, a random monte carlo stochastic sampling, a genetic algorithm, or manual or human user intervention could also be used to optimize the final PWM.

In some cases for selected residues in the non target epitope regions, the side chains of any positions to be varied are then removed. The resulting structure consisting of the protein backbone (including the fixed backbone structure of the analog) and the remaining sidechains may be called the template. Each variable residue position can then be optionally classified as a core residue, a surface residue, or a boundary residue. In that case, each classification defines a subset of possible amino acid residues for the position (for example, core residues generally will be selected from the set of hydrophobic residues, surface residues generally will be selected from the hydrophilic residues, and boundary residues may be either). Each amino acid residue or the analog can be represented by a discrete set of all allowed conformers of each side chain, called rotamers. Thus, to arrive at different potential antigenic variants for a backbone, all possible sequences may be screened, where each backbone position can be occupied either by each amino acid in all its possible rotameric states, or a subset of amino acids. For this purpose, the analog backbone is treated as part of the target antigen template.

In some cases, not all possible sequences may be screened for each backbone position. In some cases, the frequency of amino acids and individual positions may be used to determine which positions may be more tolerant than others for diverisification. In some cases, where there is homolog data available, amino acid position frequency may be used to provide further skewing optimization in the PWM, wherein positions that are tolerant of changes may be diversified, while positions that are evolutionarily conserved may be masked or blocked from diversification.

For sequences that meet percent identity thresholds, (e.g. exhibit non-target percent identity less than 90% and target epitope conservation), sequence may be further tested in silico for predicted biochemical stability. For example, a criterion such as theoretical quantitative stability may be used as a measure of the stability of a conformation and thus stability of the presented conserved target epitope. For example, different antigen sequences may be tested by calculating $\Delta G$ of individual folded molecules. Molecules for which $\Delta G$ is substantially higher than the reference sequence or antigen may be excluded or lower ranked (as described herein). In other silico tests, stability may be tested by applying a thermal function to predicted folds of individual antigen variants. Variants that are found to be thermally unstable (e.g. predicted to denature, unfold, or improperly fold), may be excluded or lower ranked in the library.

Methods to rank rank-list sequences may performed using any suitable methods. For example profile scores (Bowie et al., Science 253(5016): 164-70 (1991), incorporated by reference) and/or potentials of mean force (Hendlich et al., J. Mol. Biol. 216(1): 167-180 (1990), also incorporated by reference) can also be calculated to score sequences. These methods assess the match between a sequence and a 3D protein structure and hence can act to screen for fidelity to the protein structure. By using different scoring functions to rank sequences, different regions of sequence space can be sampled in the computational screen.

Furthermore, scoring functions can be used to screen for sequences that would create metal or co-factor binding sites in the protein (Hellinga, Fold Des. 3(1):R1-8 (1998), hereby expressly incorporated by reference). Similarly, scoring functions can be used to screen for sequences that would create disulfide bonds in the protein. These potentials attempt to specifically modify a protein structure to introduce a new structural motif.

Similarly, molecular dynamics calculations can be used to computationally screen sequences by individually calculating mutant sequence scores and compiling a rank ordered list.

In a preferred embodiment, residue pair potentials can be used to score sequences (Miyazawa et al., Macromolecules 18(3):534-552 (1985), expressly incorporated by reference) during computational screening.

Similarly, as outlined above, other computational methods are known, including, but not limited to, sequence profiling (Bowie and Eisenberg, Science 253(5016): 164-70, (1991)), rotamer library selections (Dahiyat and Mayo, Protein Sci 5(5): 895-903 (1996); Dahiyat and Mayo, Science 278(5335): 82-7 (1997); Desjarlais and Handel, Protein Science 4: 2006-2018 (1995); Harbury PNAS USA 92(18): 8408-8412 (1995); Kono et al., Proteins: Structure, Function and Genetics 19: 244-255 (1994); Hellinga and Richards, PNAS USA 91: 5803-5807 (1994)); and residue pair potentials (Jones, Protein Science 3: 567-574, (1994)), all of which are expressly incorporated by reference.

The computational processing results in a set of optimized protein sequences that each contain the target epitope displayed in a native conformation as the target antigen, and non target epitope sequences that have been optimized to fold in a similar fashion as the target antigen, but comprise a protein surface highly divergent from surfaces of the target antigen. These optimized protein sequences may be significantly different from the wild-type sequence from which the backbone was taken. That is, each optimized protein sequence may comprises at least one residue change, or at least 1%, 2%, 3%, 4%, 5%, 6%, 7%, 8%, 9%, 10%, 11,%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 80%, or 90% or more variant amino acids from the starting or wild-type sequence. In some cases each optimized protein sequence may comprises at most one residue change, or at least 1%, 2%, 3%, 4%, 5%, 6%, 7%, 8%, 9%, 10%, 11,%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 80%, or 90% or more variant amino acids from the starting or wild-type sequence.

The library or a population of optimized sequences, may be outputted as a rank-ordered list. Generally, all possible sequences of a protein may be ranked; however, the number of sequences may be capped due to computational limitation. Thus, in general, some subset of all possible sequences may be used as the primary library. In some cases a library may include at least $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, $1 \times 10^{18}$, $1 \times 10^{19}$, $1 \times 10^{20}$, $1 \times 10^{21}$, $1 \times 10^{22}$, $1 \times 10^{23}$, $1 \times 10^{24}$, $1 \times 10^{25}$, $1 \times 10^{30}$, $1 \times 10^{35}$, $1 \times 10^{40}$, or $1 \times 10^{50}$ antigen variants or antigen members. In some cases a library may include at most $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1\times10^{17}$, $1\times10^{18}$, $1\times10^{19}$, $1\times10^{20}$, $1\times10^{21}$, $1\times10^{22}$, $1\times10^{23}$, $1\times10^{24}$, $1\times10^{25}$, $1\times10^{30}$, $1\times10^{35}$, $1\times10^{40}$, or $1\times10^{50}$ antigen variants or antigen members. Generally, the top or highest ranked $1\times10^3$ to $1\times10^{13}$ sequences are chosen for the library. The cutoff for inclusion in the rank ordered list of the primary library can be done in a variety of ways. For example, the cutoff may be just an arbitrary exclusion point: the top 1% of sequences may comprise the library. Alternatively, all sequences scoring within a certain limit of the global optimum can be used; for example, all sequences with 10 kcal/mol of the global optimum could be used as the primary library. This method has the advantage of using a direct measure of fidelity to a three dimensional structure to determine inclusion. This approach can be used to insure that library mutations are not limited to positions that have the lowest energy gap between different mutations. Alternatively, the cutoff may be enforced when a predetermined number of mutations per position is reached. As a rank ordered sequence list is lengthened and the library is enlarged, more mutations per position are defined. Alternatively, the total number of sequences defined by the recombination of all mutations can be used as a cutoff criterion for the primary sequence library. In some cases the values for the total number of sequences range from 100 to $1\times10^2$. In some cases values range from 1000 to $1\times10^{13}$. In some cases values range from 1000 to $10\times10^7$. Alternatively, the first occurrence in the list of predefined undesirable residues can be used as a cutoff criterion. For example, the first hydrophilic residue occurring in a core position would limit the list. It should also be noted that while these methods are described in conjunction with limiting the size of the primary library, these same techniques may be used to formulate the cutoff for inclusion in the secondary library as well.

E. Variable Surface Concentration Ensemble Generation

After generation of antigen variants in silico, another algorithm is used to aid in selection and formulation of an immunogenic composition comprising two or more antigen variants, (204). The composition and methods of the disclosure provide for generation of one or more immunogenic compositions, wherein an immunogenic composition may be able to elicit an immune response from a subject or immune cell, but that individual antigen variants or antigen members of the immunogenic composition may be held at a concentration insufficient to elicit an immune response. In some cases, the concentration of antigen members is too low to elicit a response individually. However, when combined into an ensemble for an immunogenic composition, the sum of the effective concentration of the target epitope, as found across antigen members in the ensemble, is sufficient to elicit an immune response. The algorithm used, to generate a variable surface concentration ensemble (or mixture of antigen members or antigen variants) employs a general strategy to combine different antigen variants into a mixture, wherein there is sufficient separation between effective concentrations of the target epitope and non-target epitopes that an immunization can be expected to only result in sufficient concentration of antigen for B-cell or T-cell activation of the target epitopes, but not the non target epitopes surfaces.

In some cases, each antigen member or antigen variant is assigned a score, based on the predicted concentration of the target epitope. The concentration of the target epitope may be calculated as a function of similarity (e.g. percent identity) across all target epitopes in the antigen member library generated in the previous step as well as disimiliarity across non target epitopes (e.g. percent identity). For example, target epitopes that may be predicted to have undergone more spatial change than others may be assigned a lower concentration score. The algorithm may then select either a predetermined number or non predetermined number of antigen members or antigen variants to create an ensemble mixture, and assign each antigen member or variant a concentration, such that the concentration of target epitope equals or exceeds a certain threshold concentration. In some cases the threshold concentration may be the minimum concentration of target epitope required to elicit an immune response.

In some cases, an ensemble may include at least 2, 5, 10, 15, 20, 25, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 25000, 50000, or 100000 antigen members or antigen variants. In some cases, an ensemble may include at most 2, 5, 10, 15, 20, 25, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 25000, 50000, or 100000 antigen members or antigen variants.

Additionally, in some cases, some antigen variants may not contain the target epitope. In some cases, a particular ensemble may comprise a mixture of antigen variants. In some cases, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 90%, 95%, 99%, 99.999% of an ensemble may comprise antigen variants without a target epitope. In some cases, at most 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 90%, 95%, 99%, 99.999% of an ensemble may comprise antigen variants without a target epitope.

In some cases, at least 1, 2, 3, 4, 5, 6, 7, 8, 9, 10, 20, 30, 40, 50, 60, 70 80, 90 or 100 ensembles may be generated for a particular antigen. In some cases, at most 1, 2, 3, 4, 5, 6, 7, 8, 9, 10, 20, 30, 40, 50, 60, 70 80, 90 or 100 ensembles may be generated for a particular antigen.

IV. Formulation: Biochemical Testing and Formulation of an Immunogenic Composition After the design process, the various algorithms as described herein, provide one or more ensembles, each ensemble comprising a plurality of antigenic members or variants designed and optimized in in silico. Generally, the design process provides amino acid sequences of all the antigenic variants in an ensemble. In order to develop and formulate the immunogenic composition from the ensemble, recombinant protein for each ensemble may be made in vitro for the subsequent administering process, wherein the immunogenic composition is exposed to the immune system of an animal or subject or an immune cell.

A. General Recombinant Methods for Expression of Antigen Protein

Antigen variants or antigen members of an ensemble may be produced in vitro using a variety of methods including recombinant and traditional biochemical purification methods.

In some cases sequences as provided by the design process for various antigen variants may be cloned into an appropriate expression vector and expressed in a host cell. Successful protein expression and/or biochemical testing of individual proteins may be used to validate the stability of the protein sequence and utility as a member of the immunogenic composition to be formulated for administration.

Generally, after the design process, an ensemble, comprising a plurality of antigen variant sequences, is generated in silico. The amino acid sequences generated in this step may be reverse translated into corresponding nucleic acid sequences. Nucleic acid sequences may be further optimized by applying codon optimization techniques known the art for particular expression systems to be used. For example, nucleic acid sequences may be codon optimized for expression in *E. coli* or insect cells, or human cells or expression in virtually any host cell as described herein.

Generally, any suitable host cell may be used to express antigen variant proteins. Generally, host cells may include bacteria, (e.g. *E. coli*), fungal cells, (e.g. *S. Cerevisiae*), insect cells (Sf9, Hi5, Sf21 cell lines), animal cells (e.g. CHO, HEK293, HeLa), plant cells (*N. tabacum, A. thaliana*) and the like. Host cells may be present in vitro (i.e. tissue culture cells or cell lines), or in vivo (i.e. cells in an organism).

As mentioned previously, methods well known to those skilled in the art may be used to construct cloning vectors containing antigen variant sequences, transcriptional and translational control elements and DNA sequences. Exemplary techniques are described in Sambrook, J. et al. (1989) Molecular Cloning, A Laboratory Manual, Cold Spring Harbor Press, Plainview, N.Y., Ausubel, F. M. et al. (1989) Current Protocols in Molecular Biology, John Wiley & Sons, New York, N.Y., and Green, E. et al. (1997) Genome Analysis, A Laboratory Manual, Cold Spring Harbor Press, Plainview, N.Y. In some cases, sequences generated by the design process may be synthetically manufactured prior to cloning into expression vectors.

In order to obtain antigen expression of sufficient quantity, cloning of the antigen sequences into an expression vector may be employed. An expression vector may contain necessary elements for transcription and/or translation of the inserted coding sequences. Expression vectors and systems known in the art may be employed for producing full length or only portions of the polypeptides of the biological agents and compounds of the disclosure.

Generally, nucleic acid sequences of individual antigen variants are operably linked to one or more transcriptional control sequences, e.g., a promoter and an enhancer. Generally, such nucleic acids are also incorporated into a plasmid or an expression vector, which is then introduced into a host cell to allow expression of the protein. The type of transcriptional control sequences used may depend on the particular expression system used, e.g., whether the system is prokaryotic (e.g., bacterial) or eukaryotic (e.g., yeast, avian, insect or mammalian), or an in vitro transcription system.

In some cases, the expression system is a prokaryotic expression system. Generally, a nucleic acid encoding a protein of interest is operably linked to one or more transcriptional control elements, such as a promoter; the nucleic acid is introduced into a prokaryotic host cell; and the host cell is cultured such as to produce the protein of interest. A plasmid may comprise sequences required for appropriate transcription of the nucleic acid in bacteria, e.g., a promoter and a transcription termination signal. The vector or plasmid can further comprise sequences encoding factors allowing for the selection of bacteria comprising the nucleic acid of interest, e.g., gene encoding a protein providing resistance to an antibiotic and sequences required for the amplification of the nucleic acid, e.g., a bacterial origin of replication. Exemplary vectors for the expression of a protein in prokaryotic cells, such as *E. coli*, include but are not limited to plasmids of the types: pBR322-derived plasmids, pEMBL-derived plasmids, pEX-derived plasmids, pBTac-derived plasmids and pUC-derived plasmids.

Any of the numerous prokaryotic expression systems known in the art can be used in the invention. Numerous systems are commercially available, (e.g., from Novagen and Life Technologies). Exemplary systems are described herein. The expression vector can be introduced into the prokaryotic host cells according to methods known in the art, e.g., heat shock transfection of chemically competent cells or electroporation. Host cells having incorporated the expression vector are then identified and used for the production of the protein of interest.

The nucleic acid encoding the protein of interest can be under the control of an inducible promoter. Such promoters are well known in the art and are found in commercially available vectors. The presence of an inducible promoter facilitates expression of proteins that may otherwise be toxic to the host cells. For example, the powerful phage T5 promoter, which is recognized by *E. coli* RNA polymerase, can be used together with a lac operator repression module to provide tightly regulated, high level expression or recombinant proteins in *E. coli*. Such vectors are available commercially, e.g., from Qiagen (Chatsworth, Calif.; QIAexpress pQE vectors). Other inducible promoters are those that are inducible by iron or in iron-limiting conditions. In some cases, an inducible promoter is used which can be activated by temperature, isopropylthio-beta-galactoside (IPTG), NaCl, or other stimuli.

Eukaryotic protein expression systems can be based on any suitable eukaryotic species (e.g., mammalian cells, insect cells, yeast cells and plant cells). Generally, a nucleic acid encoding a protein of interest is operably linked to at least one transcriptional control element, e.g., a promoter and an enhancer. Eukaryotic transcriptional control elements are well known in the art and are described, e.g., in Goeddel; Gene Expression Technology: Methods in Enzymology 185, Academic Press, San Diego, Calif. (1990).

A number of vectors exist for the expression of recombinant proteins in yeast. For instance, YEP24, YIP5, YEP51, YEP52, pYES2, and YRP 17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein).

In addition, drug resistance markers such as ampicillin, zeomycin, bleomycin, DHFR, or neomycin can be used for selection of prokaryotic or eukaryotic host cells containing the recombinant vector.

An alternative eukaryotic expression system which can be used to express a recombinant protein is an insect system. For example, a baculovirus expression system can be used. Examples of such baculovirus expression systems include pVL-derived vectors (such as pNL 1392, pVL1393 and pVL941), pAcUW-derived vectors (such as pAcUW1), and pBlueBac-derived vectors (such as the β-gal containing pBlueBac III).

In another insect system, *Autographa californica* nuclear polyhedrosis virus (AcNPN) is used as a vector to express foreign genes. The virus grows in *Spodoptera frugiperda* cells (Sf cells). The gene sequence may be cloned into non-essential regions (for example the polyhedrin gene) of the virus and placed under control of an AcNPN promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, (e.g., see Smith et al., 1983, J. Nirol., 46:584, Smith, U.S. Pat. No. 4,215,051).

In cases in which plant expression vectors are used, the expression of a protein may be driven by any of a number of promoters and expression systems. For example, viral promoters such as the 35S RNA and 19S RNA promoters of CaMV (Brisson et al., 1984, Nature, 310:511-514), or the coat protein promoter of TMN (Takamatsu et al., 1987, EMBO J., 6:307-311) may be used; alternatively, plant promoters such as the small subunit of RUBISCO (Coruzzi et al., 1994, EMBO J., 3:1671-1680; Broglie et al., 1984, Science, 224:838-843); or heat shock promoters, eg., soybean lisp 17.5-E or hsp 17.3-B (Gurley et al., 1986, Mol. Cell. Biol., 6:559-565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, New York, Section VIII, pp. 421-463; and Grierson & Corey, 1988, Plant Molecular Biology, 2d Ed., Blackie, London, Ch. 7-9.

In some cases, mammalian expression vectors may contain both prokaryotic sequences, to facilitate the propagation of the vector in bacteria, and one or more eukaryotic transcription units that are expressed in eukaryotic cells. The pcDNAI/amp, pcDNAI/neo, pRc/CMN, pSN2gpt, pSN2neo, pSN2-dhfr, pTk2, pRSNneo, pMSG, pSVT7, pko-neo and pHyg derived vectors are non-limiting examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPN-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some cases, stable expression of polynucleotide sequences of each antigen member sequence in a host cell line may be used. For example, cell lines which stably each antigen may be generated. An individual cell line for each antigen member may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells, which successfully express the introduced sequences. Resistant clones of stably transformed cells may be proliferated using tissue culture techniques appropriate to the cell type.

In some cases generating trangenic expression cell lines or organisms containing stably integrated expression constructs may be useful for long-term, high-yield production of recombinant antigen members or antigen variants.

In another example, a transgenic organism may be generated for the production of one or more antigen variants. For example, transgenic plants may be engineered to express one or more antigen variants, such as *A. thaliana* or *N. tabacum*. In some cases, an appropriately engineered vector comprising polynucleotide sequence of the antigen variant and various regulatory sequences (i.e. promoter sequence, terminator sequences etc. . . . ) may be introduced into a plant via agrobacteria mediated "floral dip" transformation as known in the art. Transgenic seeds may be recovered, wherein stable integration of the antigen variant sequence containing construct has occurred. Transgenic seeds may then be propagated to produce plants expressing the antigen variants and subsequently used to extract, purify and test the antigen variant protein.

As another example, a host cell strain or organism may be chosen for its ability to modulate the expression of the inserted sequences or to process the expressed proteins or peptides in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the antigen.

In other cases, expression of antigen variant sequences may also be generated using transient expression systems using any of the host, vectors, or methods described herein. For example, insect cells may used to generate protein using transient expression of constructs using baculo virus as described herein. Plants may also be used for transient expression of constructs using viral based methods, or agrobacteria mediated methods as described herein.

In some cases generating transgenic expression cell lines or organisms containing transient expression constructs may be useful for generating and testing antigen variant proteins faster and in high-throughput compatible formats.

Generally, any suitable amount of protein may be expressed. In some cases, antigen variant protein may be produced in quantities of at least 1 μg, 10 μg, 100 μg, 1 μg, 10 μg, 100 μg, 200 μg, 300 μg, 400 μg, 500 μg, 600 μg, 700 μg, 800 μg, 900 μg, 1 μg, 10 μg, 100 μg, 200 μg, 300 μg, 400 μg, 500 μg, 600 μg, 700 μg, 800 μg, 900 μg, 1 ng, 10 ng, 100 ng, 200 ng, 300 ng, 400 ng, 500 ng, 600 ng, 700 ng, 800 ng, 900 ng, 1 mg, 10 mg, 100 mg, 200 mg, 300 mg, 400 mg, 500 mg, 600 mg, 700 mg, 800 mg, 900 mg or 1 g. In some cases, antigen variant protein may be produced in quantities of at most 1 μg, 10 μg, 100 μg, 1 μg, 10 μg, 100 μg, 200 μg, 300 μg, 400 μg, 500 μg, 600 μg, 700 μg, 800 μg, 900 μg, 1 μg, 10 μg, 100 μg, 200 μg, 300 μg, 400 μg, 500 μg, 600 μg, 700 μg, 800 μg, 900 μg, 1 ng, 10 ng, 100 ng, 200 ng, 300 ng, 400 ng, 500 ng, 600 ng, 700 ng, 800 ng, 900 ng, 1 mg, 10 mg, 100 mg, 200 mg, 300 mg, 400 mg, 500 mg, 600 mg, 700 mg, 800 mg, 900 mg or 1 g.

B. High Throughput Methods for Antigen Variant Expression

In some cases, such as in instances in which numerous antigen variants of an ensemble may be produced, high throughput expression methods may be used.

In some cases phage display may be used, whereby a plurality of antigen variants or antigen member sequences of one or more ensembles are pooled. Using methods in the art, each antigen variant may be expressed on a portion of the phage, including areas such as capsid or tail. Phage display methodologies, may be used to test antigens recognized by antibodies as provided by (Scott, J. K. et al. (1990) "Searching for Peptide Ligands using an Epitope Library," Science 249(4967):386-390), incorporated by reference in its entirety herein.

In some cases a phage display library may be constructed to express one or more antigen variants. In some cases, antigen variants are displayed on the surface of a phage in the form of a fusion with a coat protein of the phage. This chimeric outer surface protein is the processed product of the polypeptide expressed by a display gene, or antigen variant sequence, or partial antigen variant sequence, inserted into the phage genome. Generally, the genome of the phage may allow introduction of the display gene either by tolerating additional genetic material or by having replaceable genetic material; the virion may be capable of packaging the genome after accepting the insertion or substitution of genetic material; and the display of the coat protein-antigen vairant protein fusion on the phage surface may not disrupt virion structure sufficiently to interfere with phage propagation.

When the viral particle is assembled, its coat proteins may attach themselves to the phage: a) from the cytoplasm, b) from the periplasm, or c) from within the lipid bilayer. The immediate expression product of the antigen variant may comprise, at its amino terminal, a functional secretion signal peptide, if the coat protein attaches to the phage from the periplasm or from within the lipid bilayer. If a secretion signal is necessary for the display of the antigen variant protein, in some cases, the bacterial cell in which the antigen variant is expressed is of a "secretion-permissive" strain.

In some cases, the polynucleotide sequence encoding the antigen variant may precede the sequence encoding the coat protein proper if the amino terminal of the processed coat protein is normally free, or may follow it if the carboxy terminal is the normal free end.

When variegation is introduced, multiple infections could generate hybrid viral particles that carry the gene for one antigen variant but have at least some copies of a different antigen variant on their surfaces; in some cases, this may be minimized whereby cells are infected with phage under conditions resulting in a low multiple-of-infection (MOI). For a given bacteriophage, a coat protein is usually one that is present on the phage surface in the largest number of copies, as this allows the greatest flexibility in varying the ratio of coat protein-antigen variant to wild type coat protein and also gives the highest likelihood of obtaining satisfactory affinity separation. One example of suitable coat protein may include but is not limited to M13 gIII protein.

In many cases the wild-type coat protein gene is preserved. The antigen variant sequence may be inserted either into a second copy of the recipient coat protein gene or into a novel engineered coat protein gene. In some cases the coat protein and antigen variant sequence are placed under control of a regulated promoter including but not limited to promoters such as lacUV5, tac, or trp.

Generally, any suitable position for insertion of the antigen variant gene into a phage genome may be used. In some cases bacteriophage are highly ordered, such as a filamentous phage. Filamentous phage can be described by a helical lattice; isometric phage, by an icosahedral lattice. Each monomer of each major coat protein sits on a lattice point and makes defined interactions with each of its neighbors. Antigen variants that fit into the lattice by making some, but not all, of the normal lattice contacts may destabilize the virion by: a) aborting formation of the virion, b) making the virion unstable, or c) leaving gaps in the virion so that the nucleic acid is not protected. In some cases use phage display to produce antigen variants for ensembles employs techniques for engineered coat protein-antigen variant fusion proteins such that those residues of the parental coat proteins that interact with other proteins in the virion are kept intact in the assembled virion.

In some cases, such as M13 gVIII, the entire mature protein may be retained. In other cases, engineering a coat protein-antigen variant fusion protein capable of functional phage assembly may be performed by truncating the coat protein. In some cases, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% of the wildtype coat protein may be used in a fusion with an antigen variant. In some cases, at most 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% of the wildtype coat protein may be used in a fusion with an antigen variant.

In some cases, the coat protein may be mutated or altered to engineer a a coat protein-antigen variant fusion protein capable of functional phage assembly. In some cases at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% of the wildtype coat protein may be mutated or altered in a fusion with an antigen variant. In some cases at most 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% of the wildtype coat protein may be mutated or altered in a fusion with an antigen variant.

In some cases, the individual phage library may be used to express or display an individual antigen variant (i.e. all phage display an identical antigen variant). In other cases, a phage library may be used to one or more antigen variants (i.e. phage display non-identical antigen variant). In some cases, one more phage libraries may be combined to create an ensemble as part of a immunogenic composition. Further formulations of immunogenic compositions comprising phage libraries are described herein.

Failed expression or expression of non functional protein may be quickly tested using such a method or any of the methods as described herein.

The recombinant antigen variant proteins can also be produced in an in vitro system, e.g., in an in vitro transcription and translation system. Many vectors for in vitro transcription are available commercially. These may contain one or more of the promoters SP6, T3 and T7 and may additionally contain a poly A sequence at the 3' end of the poly linker in which the DNA of interest is inserted. Vectors that can be used for in vitro transcription are also described, e.g., in U.S. Pat. No. 4,766,072. In vitro transcription can be conducted with a nucleic acid that is not per se a vector, but merely contains the elements necessary for in vitro transcription. For example, such a template nucleic acid may comprise an RNA polymerase promoter located upstream of the antigen variant sequence to transcribe. Such template nucleic acids can be obtained, e.g., by polymerase chain reaction (PCR) amplification of a sequence of interest using a primer that contains an RNA polymerase promoter. PCR amplification methods are well known in the art.

An in vitro transcription reaction can be carried out according to methods well known in the art. Kits for performing in vitro transcription kits are also commercially available from several manufacturers.

In an illustrative case, a vector containing an RNA Polymerase promoter and an antigen variant sequence of interest is preferably first linearized downstream of the antigen variant sequence by e.g., restriction digest with an appropriate restriction enzyme. The linearized DNA is then incubated in the presence of ribonucleotides, an RNAase inhibitor, an RNA polymerase recognizing the promoter that is operably linked upstream of the insert to be transcribed. Following the transcription reaction, RNAase free DNAse can be added to remove the DNA template and the RNA can be purified by, e.g., a phenol-chlorophorm extraction. Further details and variations of this general method may be found in the art (e.g., in Molecular Cloning A Laboratory Manual, 2nd Ed., ed. by Sambrook, Fritsch and Maniatis (Cold Spring Harbor Laboratory Press: 1989)).

In vitro synthesized RNA can be in vitro translated using an in vitro translation system. A variety of in vitro translation systems are well known in the art and are commercially available. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, 111; and GIBCO/BRL, Grand Island, N.Y. In vitro translation systems typically comprise macromolecules, such as enzymes, translation, initiation and elongation factors, chemical reagents, and ribosomes.

Synthesis of recombinant proteins can be generally adapted to high throughput, e.g., in multi-well plates. For example, proteins can be expressed in multi-well plates using the Rapid Translation System of Roche (RTS 100 *E. coli* HY Kit; Roche). This kit contains everything needed to perform protein expression in tubes or multi-well plates, and includes *E. coli* lysate, reaction mix, amino acid mixture (without methionine), methionine, reconstitution buffer, GFP control vector, and 200 µl thin-walled tubes.

In certain high throughput embodiments, nucleic acids encoding proteins of interest for use in an in vitro transcription and translation assay, such as that of the RTSIOO system from Roche, are prepared in a multi-well plate, in which it is then transcribed and translated. For example, a nucleic acid comprising a sequence encoding a protein of interest is incubated in a well of a multi-well plate together with two primers and reagents for conducting PCR.

For example, the amplified product can comprise the promoter at its 5' end, to permit in vitro transcription. After conducting a PCR reaction to amplify the nucleic acid encoding the protein of interest, and optionally linking a promoter to it, the nucleic acid may be used in an in vitro transcription reaction. The method may comprise a step of removing certain reagents used in the PCR reaction prior to in vitro transcription and translation. For example, one or both primers can be removed from the reaction. Alternatively, the PCR product can be purified away from some or most of the PCR reagents. For example, the PCR product can be synthesized with a label (which will essentially not affect the transcription of the PCR product), e.g., biotin, and the PCR products isolated on an avidin or streptavidin solid surface, e.g., beads.

In another example, high throughput protein expression may include methods using two-hybrid systems, whereby a library of antigen sequences are introduced in plurality of individual host cells and induced to express individual antigen variants. In some cases, this method, as known in the art, may use yeast as the host cell. In other cases, insect cells or mammalian cells may be suitable for protein expression.

C. Protein Purification

Generally, after successful expression, any suitable means for protein purification may be used. Exemplary techniques are described in Sambrook, J. et al. (1989) Molecular Cloning, A Laboratory Manual, Cold Spring Harbor Press, Plainview, N.Y., Ausubel, F. M. et al. (1989) Current Protocols in Molecular Biology, John Wiley & Sons, New York, N.Y., and Green, E. et al. (1997) Genome Analysis, A Laboratory Manual, Cold Spring Harbor Press, Plainview, N.Y.

Purifying an identified mutant protein comprises separating it (completely or partially) from at least one contaminant. Identified molecules can be purified from undesired contaminants purified via one or more purification steps. Some purification processes can result in a "homogeneous" preparation comprising at least 70% (e.g., at least 80%, at least 90% by weight, or at least 95%) by weight of the identified molecule(s). Other purification processes (e.g., obtaining a cell lysate, cell extract or cell culture supernatant) can result in a lower degree of purification, which may nonetheless be suitable for a particular use. For example, cell lysates and cell extracts can be used to make an in vitro translation transcription (IVTT) system.

Steps for purifying identified protein(s) from cultured cells can depend on whether the identified protein(s) remains inside cultured cells or are secreted into the cell culture growth medium. For identified proteins that remain within cultured cells, purification typically involves disrupting the cells (e.g., by mechanical shear, freeze/thaw, osmotic shock, chemical treatment, and/or enzymatic treatment). Such disruption results in a cell lysate that contains the identified molecule and other cellular constituents. In some cases, much of the undesired cellular material can be removed by filtration or centrifugation to yield a cell extract that contains the partially purified molecule.

Chromatographic techniques often are used to further purify an identified protein from cell culture growth medium, products of cellular metabolism, and/or other cellular constituents. Such techniques can separate polypeptides on the basis of size, charge, hydrophobicity, or presence of purification tags, to name a few. Chromatographic separation schemes can be tailored to particular identified polypeptides, using one or more chromatographic techniques and/or separation media. During chromatographic separation, an identified polypeptide can move at a different rate through a separation medium, or can adhere selectively to the separation medium, relative to undesired molecules. In addition, an identified protein can be positively selected or negatively selected. Thus, in some negative selection schemes using chromatographic separation, identified molecules can be separated from undesired molecules when the undesired molecules adhere to the separation medium and the identified molecule(s) do(es) not. In such a scheme, the identified molecules are present in the eluate or flow-through and undesired molecules are retained in association with the separation medium. Alternatively, in positive selection schemes, the identified molecules can be separated from undesired molecules when identified (desired) molecules adhere to the separation medium and undesired molecules do not. In such a scheme, the eluate or flow-through contains undesired molecules, and the separation medium retains the the identified proteins. The identified molecules can be then be recovered, for example, by exposing the separation medium to a chemical or enzymatic agent suitable for dissociating the desired polypeptide.

Ion exchange chromatography is just one chromatographic technique that can be used to purify the identified proteins. In ion exchange chromatography, charged portions of molecules in solution are attracted by opposite charges of an ion exchange medium when the ionic strength of the solution is sufficiently low. Solutes can be dissociated from an ion exchange medium and eluted from an ion exchange column by increasing the ionic strength of the solution. Changing the pH to alter solute charge is another way to dissociate solutes from an ion exchange medium. Ionic strength and/or pH can be changed gradually (gradient elution) or stepwise (stepwise elution).

Metal ion affinity chromatography (MIAC) is another chromatographic technique that can be used to purify identified molecules. MIAC is an affinity chromatography technique that involves the binding of desired molecules to metal ions. Immobilized metal ion affinity chromatography (IMAC) is a type of MIAC technique that involves the use of a separation medium to which metal ions have been chelated. The identified polypeptides may be immobilized on such a metal chelate substrate, reportedly via interaction(s) between metal ion(s) and electron-donating amino acid(s) such as histidine and cysteine. Thus, IMAC routinely is used to purify recombinant polypeptides that include polyhistidine or polycysteine motifs (tags). Whether, and with what affinity, a particular desired polypeptide will bind to a metal chelate substrate can depend on the conformation of the polypeptide, the number of available coordination sites on the chelated metal ion ligand, and the number of amino acid side chains available to bind the chelated metal ion ligand.

The nature of a tag will depend on the particular affinity purification system used. Various systems are available. In one embodiment, the affinity chromatographic system is immobilized metal affinity chromatography (IMAC), which is based on binding of a tag to a metal ion resin. Metal ions can be, e.g., zinc, nickel, or cobalt ions. The tag can be a polyhistidine sequence, which interacts specifically with metal ions such as nickel, cobalt, iron, or zinc. A polyhistidine tag can be 2, 3, 4, 5, 6, 7, 8, 9, 10, 11, 12, 13, 14, 15, 16, 17, 18, 19, 20, 25, 30, 35, 40, or 50×His or other, provided that it binds essentially specifically to a metal ion. In some cases, the His tag is a 6×His or 12×His tag. The tag can also be a polylysine or polyarginine sequence, comprising at least four lysine or four arginine residues, respectively, which interact specifically with zinc, copper or a zinc finger protein. Commercially available systems for IMAC include the following systems, which are sold as kits and as individual components, e.g., vectors, bacterial strains, affinity resins and instructions for use: QIAexpress Ni-NTA Protein Purification System of Qiagen (Qiagen, CA); HAT™ Protein Expression & Purification System (Clontech, Palo Alta, Calif.); pTrcHis Xpress™ Kit (InVitrogen); and Bug-Buster™ HisEind® Purification Kit (Novagen).

In a preferred embodiment, the invention comprises purifying a plurality of recombinant proteins in multi-well plates. The affinity resins may be present on magnetic beads, thereby allowing easy removal of the beads from the wells.

In some cases the tag peptide comprises a glutathione-S-transferase (GST) fusion protein and the affinity purification comprises using glutathione, GST or an antibody to GST. Systems for expressing and purifying recombinant proteins comprising a GST tag are available from Novagen as BugBuster™ GSTBind™ Purification Kit and GST-Tag™ Assay Kit. Exemplary vectors for producing such fusion proteins include the pGEX prokaryotic expression vectors from Pharmacia (Piscataway, N.J), e.g., pGEX-5. GST fusion proteins can be affinity purified using glutathione-Sepharose (Sigma Chem. Co.; St. Louis, Mo.) resin; GST-sepharose (Phamarcia-LKB); resin linked to an antibody specific for GST, e.g., mouse anti-GST-Sepharose® 4B (Zymed Laboratories). Protein purification can be performed as described, e.g., in Kuge et al. (1997) Protein Science 6: 1783.

Other affinity purification systems comprise a T7 tag, e.g., available in the T7*Tag® Purification Kit (Novagen); an S tag or thioredoxin (trxA) tag (Novagen); and a Self-Cleavable Chitin-binding Tag, e.g., in the IMPACT™-TWTN System and IMPACT™-CN System (New England Biolabs); or a myc epitope or a peptide portion of the *Haemophilus* influenza hemagglutimn protein, against which specific antibodies can be prepared and also are commercially available. Other affinity systems include maltose sepharose or agarose affinity chromatrography using a maltose binding protein, and lectin affinity chromatography.

Additional affinity purification systems are based on the interaction between a tag peptide and an antibody to the tag peptide. Tag specific antibodies can be raised using a protein containing the tag peptide, or a peptide portion thereof, as an immunogen. Such an immunogen can be prepared from natural sources, produced recombinantly, or can be synthesized using routine chemical methods. An otherwise non-immunogenic epitope can be made immunogenic by coupling the hapten to a carrier molecule such bovine serum albumin (BSA) or keyhole limpet hemocyanin (KLH), or by expressing the epitope as a fusion protein. Various other carrier molecules and methods for coupling a hapten to a carrier molecule are well known in the art (see, for example, Harlow and Lane, "Antibodies: A laboratory manual" (Cold Spring Harbor Laboratory Press 1988)).

Electrophoresis techniques can also be used to purify desired polypeptides. Electrophoresis is based on the principle that charged particles migrate in an applied electrical field. If electrophoresis is carried out in solution, molecules are separated according to their surface net charge density. If carried out in semisolid materials (gels), the matrix of the gel adds a sieving effect so that particles migrate according to both charge and size.

Gel-based electrophoresis can be carried out in a variety of formats, including in standard-sized gels, minigels, strips, gels designed for use with microtiter plates and other high throughput (HTS) applications, and the like. Two commonly used media for gel electrophoresis and other separation techniques are agarose and polyacrylamide gels. In general, electrophoresis gels can be either in a slab gel or tube gel form.

Electrophoresis can performed in the presence of a charged detergent like sodium dodecyl sulfate (SDS) which coats, and thus equalizes the charges of most polypeptides such that migration is more dependent upon size (molecular weight) than charge. Polypeptides often are electrophoresed in the presence SDS, e.g., SDS-PAGE techniques. In addition to SDS, one or more other denaturing agents, such as urea, can be used to minimize the effects of secondary and tertiary structure on the electrophoretic mobility of polypeptides. Such additives typically are not necessary for nucleic acids, which have a similar surface charge irrespective of their size and whose secondary structures generally are broken up by the heating of the gel that happens during electrophoresis.

Isoelectric focusing (IEF) is an electrophoresis technique that involves passing a mixture through a separation medium having a pH gradient or other pH function. An IEF system has an anode at a position of relatively low pH end and a cathode disposed at another position of higher pH. Molecules having a net positive charge under the acidic conditions near the anode will move away from the anode. As they move through the IEF system, molecules enter zones having less acidity, causing their positive charges to diminish. Each molecule will stop moving when it reaches a point in the system having a pH equivalent to its isoelectric point (pI).

Two-dimensional (2D) electrophoresis involves a first electrophoretic separation in a first dimension, followed by a second electrophoretic separation in a second, transverse dimension. In a common 2D electrophoretic method, polypeptides are subjected to IEF in a polyacrylamide gel in the first dimension, which results in separation on the basis of pI, and the molecules are then subjected to SDS-PAGE in the second dimension, resulting in further separation on the basis of size.

Capillary electrophoresis (CE) achieves molecular separations on the same basis as conventional electrophoretic methods, but does so within the environment of a narrow capillary tube (25 to 50 .mu.m). The main advantages of CE are that very small volumes of sample are all that are required, and that separation can be performed very rapidly, thus increasing sample throughput relative to other electrophoresis formats. Examples of CE include capillary electrophoresis isoelectric focusing (CE-IEF) and capillary zone electrophoresis (CZE). Capillary zone electrophoresis (CZE) is a technique that separates molecules on the basis of differences in mass to charge ratios, which permits rapid and efficient separations of charged substances. In general, CZE involves introducing a sample into a capillary tube and applying an electric field to the tube. The electric potential of the field pulls the sample through the tube and separates it into its constituent parts. Constituents of the sample having greater mobility travel through the capillary tube faster than those with slower mobility. As a result, the constituents of the sample are resolved into discrete zones in the capillary tube during their migration through the tube. An on-line detector can be used to continuously monitor the separation and provide data as to the various constituents based upon the discrete zones. It should be recognized that a recombinant protein fused to a tag peptide or other second polypeptide is in a sufficiently purified form to allow MS analysis, since the mass of the tag peptide will be known and can be considered in the determination. The tag peptide can also be cleaved from the polypeptide prior to the MS analysis, as described infra.

D. Biochemical Validation

In some instances, antigen variants or antigen members may be further validated with various biochemical assays. Successful expression of soluble protein, as determined by the presence of protein expression and/or successful purification of protein may provide some information regarding validation of the antigen variants. However further information may be required. For example, antigen members or variants may be tested for target epitope specificity using a variety of biochemical tests. In some cases, the protein structure may be determined, as with common methods in the art, such as X-ray crystallography. In other cases, biochemical assays using a known binding antibody may be used.

In cases in which an antibody may already be characterized or available, various immuno assays such as ELISA, western blot or surface Plasmon resonance may be used to assess the binding affinity for the target epitope for a particular antibody. This information may be used to validate or reject predicted affinities from the design process and/or may be used to adjust the "effective concentration assigned each antigen variant or member.

In another assay, the binding of the target epitope to a T-cell or B-cell may be determined using other immuno based assays such as fluorescence activated cell sorting (FACS). In this case, a pool of immune cells may be exposed to a purified antigen, and relative percentages or counts of cells with affinity for the antigen may be assessed and correlated with the strength of binding for the target epitope.

In addition to activity or specificity based assays, general biochemical stability and conformational specificity may also be assess using other traditional biochemical techniques. For example, differential scanning calorimetry (DCS) may be used to assess the melting temperature of individual antigen variants or members. This method may be used to assess the stability of the protein at various temperatures. Other traditional techniques may include but are not limited to fluorescence, circular dichroism spectroscopy, hydrogen exchange-mass spectroscopy, differential scanning fluorometry (DSF), protein crystallization, mass spec, MALDI-TOF and pulse proteolysis. Other methods may be used using specific ligands or binding agents that may be capable of detecting misfolding protein or exposure of the hydrophobic core, such as the use of sypro orange. Generally any biochemical assay that provides information about either the conformational stability of antigen variants, or specificity of recognition of an antibody to a target epitope on the antigen variant may be used to validate each antigen variant. Validated antigen members may be further selected to be incorporated into a formulation of an immunogenic composition.

Apart from this and/or in addition, the antigens selected for formulation of the immunogenic composition and the immunogenic composition itself may show only low to undetectable levels of aggregation even during storage under one or more of the above stress conditions. For example, at least 0.01%, 0.05%, 0.1%, 0.2%, 0.5%, 1%, 2%, 3%, 4%, 5%, 10%, 20% or 30% of the antigen variant or immunogenic composition are aggregated after storage under one or more of the above stress conditions. In some cases at most 0.01%, 0.05%, 0.1%, 0.2%, 0.5%, 1%, 2%, 3%, 4%, 5%, 10%, 20% or 30% of the antigen variant or immunogenic composition are aggregated after storage under one or more of the above stress conditions.

Aggregation as used in the present disclosure may include the development of high molecular weight aggregates, i.e. aggregates with an apparent molecular weight in SE-HPLC analysis of more/higher than the 44 kDa. As described above, 44 kDa is the apparent molecular weight observed in SE-HPLC analysis for dimers. Aggregation can be assessed by various methods known in the art. Without being limiting, examples include SE-HPLC, analytical ultracentrifugation, dynamic light scattering and/or subvisible particle counting.

In an analytical ultracentrifuge, a sample being spun can be monitored in real time through an optical detection system, using ultraviolet light absorption and/or interference optical refractive index sensitive system. This allows the operator to observe the evolution of the sample concentration versus the axis of rotation profile as a result of the applied centrifugal field. With modem instrumentation, these observations are electronically digitized and stored for further mathematical analysis. Two kinds of experiments are commonly performed on these instruments: sedimentation velocity experiments and sedimentation equilibrium experiments.

Sedimentation velocity experiments aim to interpret the entire time-course of sedimentation, and report on the shape and molar mass of the dissolved macromolecules, as well as their size-distribution (Perez-Ramirez and Steckert (2005) Therapeutic Proteins: Methods and Protocols. C. M. Smales and D. C. James, Eds. Vol. 308: 301-318. Humana Press Inc, Totowa, N.J., US.). The size resolution of this method scales approximately with the square of the particle radii, and by adjusting the rotor speed of the experiment size-ranges from 100 Da to 10 GDa can be covered. Sedimentation velocity experiments can also be used to study reversible chemical equilibria between macromolecular species, by either monitoring the number and molar mass of macromolecular complexes, by gaining information about the complex composition from multi-signal analysis exploiting differences in each components spectroscopic signal, or by following the composition dependence of the sedimentation rates of the macromolecular system, as described in Gilbert-Jenkins theory.

The kinds of information that can be obtained from an analytical ultracentrifuge include the gross shape of macromolecules, the conformational changes in macromolecules, and size distributions of macromolecular samples. For macromolecules, such as proteins, that exist in chemical equilibrium with different non-covalent complexes, the number and subunit stoichiometry of the complexes and equilibrium constant constants can be studied. (see also Scott D. J., Harding S. E. and Rowe A. J. Analytical Ultracentrifugation Techniques and Methods, RSC Publishing)

Dynamic light scattering (also known as Photon Correlation Spectroscopy or Quasi-Elastic Light Scattering) is a technique in physics, which can be used to determine the size distribution profile of small particles in solution. When a beam of light passes through a colloidal dispersion, the particles or droplets scatter some of the light in all directions. When the particles are very small compared with the wavelength of the light, the intensity of the scattered light is uniform in all directions (Rayleigh scattering); for larger particles (above approximately 250 nm diameter), the intensity is angle dependent (Mie scattering). If the light is coherent and monochromatic, as from a laser for example, it is possible to observe time-dependent fluctuations in the scattered intensity using a suitable detector such as a photomultiplier capable of operating in photon counting mode.

Aggregation can also be measured by the PAMAS SVSS-C (Small Volume Syringe System-C) instrument (PArtikelMess-und AnalyseSysteme GMBH), which is a particle size distribution analyzer for low viscous fluids. It uses the principle of light obscuration to detect sub-visible particles in the size range 1 µm-200 µm. The validation criteria/specified limits of the European Pharmacopoeia (EP<2.9.19 Particulate Contamination: sub-visible particles) for small and large volume parenterals are defined by the total counts per container:

The tendency for aggregate formation of a polypeptide in a certain formulation can also be measured by elastic light scattering. Elastic light scattering can be measured in a spectrofluorometer (e.g. excitation and emission wavelength 500 nm) by temperature-induced denaturation as measured e.g. at an angle of 90°. Preferably the maximum scatter will stay within the absorption detection limit. The scatter should be 1000 abs. or lower, preferably 750 abs or lower, such as 500 abs or lower.

Apart from this and/or in addition, the antigens selected for formulation of the immunogenic composition and the immunogenic composition itself may show only low to undetectable levels of fragmentation and/or precipitation (insolubility) even during storage. Fragmentation and degradation can be measured e.g. by SE-HPLC and/or RP-HPLC. For example, at least 0.01%, 0.05%, 0.1%, 0.2%, 0.5%, 1%, 2%, 3%, 4%, 5%, 10%, 20% or 30% of the antigen variant or immunogenic composition are degraded, fragmented or insoluble after storage under one or more of the above stress conditions. In some cases at most 0.01%, 0.05%, 0.1%, 0.2%, 0.5%, 1%, 2%, 3%, 4%, 5%, 10%, 20% or 30% of the antigen variant or immunogenic composition are degraded, fragmented or insoluble after storage.

Preferably, the antigen variants present in the formulations of the present disclosure have a solubility of at least 0.7 mM, at least 0.8 mM, at least 0.9 mM, at least 1.0 mM, at least 1.1 mM, at least 1.2 mM, at least 1.3 mM, at least 1.4 mM, at least 1.5 mM, at least 1.6 mM, at least 1.7 mM, at least 1.8 mM, at least 1.9 mM, at least 2.0 mM, at least 2.1 mM, at least 2.2 mM, at least 2.3 mM, at least 2.4 mM, at least 2.5 mM, at least 2.6 mM, at least 2.7 mM, at least 2.8 mM, at least 2.9 mM, at least 3.0 mM, at least 3.2 mM, at least 3.4 mM, at least 3.6 mM and/or at least 30 mg/ml, at least 40 mg/ml, at least 50 mg/ml, at least 60 mg/ml, at least 65 mg/ml, at least 70 mg/ml, at least 80 mg/ml, at least 90 mg/ml, at least 100 mg/ml, at least 110 mg/ml, at least 120 mg/ml, at least 130 mg/ml, at least 140 mg/ml, at least 150 mg/ml.

The techniques of static light scattering (SLS), tangential flow filtration (TFF), Fourier Transform Infrared Spectroscopy (FTIR), circular dichroism (CD), urea-induced protein unfolding techniques, intrinsic tryptophan fluorescence, differential scanning calorimetry (DSC), and/or 1-anilino-8-naphthalenesulfonic acid (ANS) protein binding can also be used to assess the physical properties and stability of polypeptides.

Apart from this and/or in addition, the formulations of the present invention show very little to no loss of potency and/or biological activity of their polypeptides, even during storage under one or more of the above stress conditions.

Apart from this and/or in addition, the antigens selected for formulation of the immunogenic composition and the immunogenic composition itself may show only very little to no loss of potency and/or biological activity of the antigen (if measurable) even during storage. For example, at least 0.01%, 0.05%, 0.1%, 0.2%, 0.5%, 1%, 2%, 3%, 4%, 5%, 10%, 20% or 30% of the antigen variant or immunogenic composition are biologically inactive after storage under one or more of the above stress conditions. In some cases at most 0.01%, 0.05%, 0.1%, 0.2%, 0.5%, 1%, 2%, 3%, 4%, 5%, 10%, 20% or 30% of the antigen variant or immunogenic composition are biologically inactive after storage.

The potency and/or biological activity of a biological describes the specific ability or capacity of said biological to achieve a defined biological effect. The potency and biological activities of the polypeptides of the disclosure can be assessed by various assays including any suitable in vitro assay, cell-based assay, in vivo assay and/or animal model known per se, or any combination thereof, depending on the specific disease or disorder involved. Suitable in vitro assays will be clear to the skilled person, and for example include ELISA; FACS binding assay; Biacore; competition binding assay (AlphaScreen, Perkin Elmer, Massachusetts, USA; FMAT); TRAP assay (osteoclast differentiation assay; Rissanen et al. 2005, J. Bone Miner. Res. 20, Suppl. 1: S256); NF-kappaB reporter gene assay (Mizukami et al. 2002, Mol. Cell. Biol. 22: 992-1000).

For example, in one embodiment, Biacore kinetic analysis uses Surface Plasmon Resonance (SPR) technology to monitor macromolecular interactions in real time and is used to determine the binding on and off rates of polypeptides of the formulations of the invention to their target. BIAcore kinetic analysis comprises analyzing the binding and dissociation of the target from chips with immobilized polypeptides of the invention on their surface.

E. Immunogenic Composition Formulation

After expression, optional purification and validation of antigen members, an ensemble is constructed per the parameters provided for by the design process. Antigen members of an ensemble are assigned a concentration in the ensemble such that the concentration of an individual antigen member is incapable of eliciting an immune response, yet the ensemble as a mixture may be capable of an immune response. In some cases, an immunogenic composition may comprise an ensemble of antigen members each provided at the indicated concentration calculated in the design process. In some cases, the ensemble may be constructed from individual antigen members or variants individually expressed, purified and combined at the specified concentration. In other cases, the ensemble may exist as a product of a high throughput expression method such as a phage library, ribosome library or hybrid system. In some cases, one or more phage libraries, ribosome libraries, in vitro translation products, or purified proteins may be combined into an ensemble to formulate an immunogenic composition.

i. Pharmaceutical Compositions

In addition to the ensemble of antigen variants, an immunogenic composition of the disclosure may comprise any suitable additional components in generation of a pharmaceutical composition. A pharmaceutically acceptable composition, when administered to a subject, can elicit an immune response against a cell that recognizes the target epitope across all antigen variants in the ensemble. The pharmaceutically acceptable compositions of the present disclosure can be useful as vaccine compositions for prophylactic or therapeutic treatment of a any disease or symptoms thereof.

In some cases, the pharmaceutically acceptable composition further comprises a physiologically acceptable carrier, diluent, or excipient. Techniques for formulating and administering also can be found in Remington's Pharmaceutical Sciences, Mack Publishing Co., Easton, Pa., latest edition.

Pharmaceutically acceptable carriers known in the art include, but are not limited to, sterile water, saline, glucose, dextrose, or buffered solutions. Agents such as diluents, stabilizers (e.g., sugars and amino acids), preservatives, wetting agents, emulsifying agents, pH buffering agents, additives that enhance viscosity, and the like. Preferably, the medium or carrier will produce minimal or no adverse effects.

In some cases, the pharmaceutically acceptable composition further comprises a physiologically acceptable adjuvant. Preferably, the adjuvant employed provides for increased immunogenicity. The adjuvant can be one that provides for slow release of antigen (e.g., the adjuvant can be a liposome), or it can be an adjuvant that is immunogenic in its own right thereby functioning synergistically with antigens. For example, the adjuvant can be a known adjuvant or other substance that promotes nucleic acid uptake, recruits immune system cells to the site of administration, or facilitates the immune activation of responding lymphoid cells. Adjuvants include, but are not limited to, immunomodulatory molecules (e.g., cytokines), oil and water emulsions, aluminum hydroxide, glucan, dextran sulfate, iron oxide, sodium alginate, Bacto-Adjuvant, synthetic polymers such as poly amino acids and co-polymers of amino acids, saponin, paraffin oil, and muramyl dipeptide.

In some cases, the adjuvant is an immunomodulatory molecule. For example, the immunomodulatory molecule can be a recombinant protein cytokine, chemokine, or immunostimulatory agent or nucleic acid encoding cytokines, chemokines, or immunostimulatory agents designed to enhance the immunologic response.

Examples of immunomodulatory cytokines include interferons (e.g., IFNα, IFNβ and IFNγ), interleukins (e.g., IL-1, IL-2, IL-3, IL-4, IL-5, IL-6, IL-7, IL-8, IL-9, IL-10, IL-12 and IL-20), tumor necrosis factors (e.g., TNFα and TNFβ), erythropoietin (EPO), FLT-3 ligand, gIp10, TCA-3, MCP-1, MIF, MIP-1α, MIP-1β, Rantes, macrophage colony stimulating factor (M-CSF), granulocyte colony stimulating factor (G-CSF), and granulocyte-macrophage colony stimulating factor (GM-CSF), as well as functional fragments of any of the foregoing. Any immunomodulatory chemokine that binds to a chemokine receptor, i.e., a CXC, CC, C, or CX3C chemokine receptor, also can be used in the context of the present disclosure. Examples of chemokines include, but are not limited to, Mip1α, Mip-1β, Mip-3α (Larc), Mip-3β, Rantes, Hcc-1, Mpif-1, Mpif-2, Mcp-1, Mcp-2, Mcp-3, Mcp-4, Mcp-5, Eotaxin, Tarc, Elc, I309, IL-8, Gcp-2 Gro-α, Gro-β, Gro-γ, Nap-2, Ena-78, Gcp-2, Ip-10, Mig, I-Tac, Sdf-1, and Bca-1 (Blc), as well as functional fragments of any of the foregoing.

In some cases, the adjuvant is a cytokine selected from the group consisting of: GM-CSF, G-CSF, IL-2, IL-4, IL-7, IL-12, IL-15, IL-21, TNF-α, and M-CSF. In some cases, the adjuvant is comprised of incomplete Freund's adjuvant (Montanide ISA 51) or *Corynebacterium granulosum* P40.

In some cases, these adjuvants cannot be expressed from a vector, in which case the adjuvant, when used, can be administered simultaneously or sequentially, in any order.

In some cases, methods and compositions of the disclosure can be used as part of combination therapies, for example as methods and/or compositions comprising one or more other agents such as, but not limited to, chemotherapeutic, immunotherapeutic, immunomodulatory, anti-angiogenic, anti-viral agents, and hormonal agents.

Examples of anti-viral agents include, but are not limited, a ganciclovir (e.g., CYTOVENE®), a valganciclovir (e.g., Valcyte@), a foscarnet (e.g., FOSCAVIR®), a cidofovir (e.g., VISTIDE®, HPMPC), an adefovir (e.g., PMEA, PREVEON®, HEPSERA®), an acyclovir (e.g., ZOVIRAX®), a valacyclovir (e.g., VALTREX™, ZELITREX™), a polyanion, and a protein kinase C inhibitor (e.g., a bis-indolylmaleide). In one case, the anti-viral agent employed in combination with the compositions and methods of the present disclosure is a ganciclover, a valganciclovir, a cidofovir, or a foscamet.

In some cases, the one or more other additional agents or components of the immunogenic composition can be a chemotherapeutic agent, naturally occurring or synthetic, for example as described in "Cancer Chemotherapeutic Agents", American Chemical Society, 1995, W. O. Foye Ed. This may be particularly useful if the immunogenic composition is directed towards cancer.

In some cases, the chemotherapeutic agent is selected from the group consisting of a small molecule receptor antagonists such as vatalanib, SU 11248 or AZD-6474, EGFR or HER2 antagonists such as gefitinib, erlotinib, CI-1033 or Herceptin, antibodies such as bevacizumab, cetuximab, rituximab, DNA alkylating drugs such as cisplatin, oxaliplatin or carboplatin, anthracyclines such as doxorubicin or epirubicin, an antimetabolite such as 5-FU, pemetrexed, gemcitabine or capecitabine, a camptothecin such as irinotecan or topotecan, an anti-cancer drug such as paclitaxel or docetaxel, an epipodophyllotoxin such as etoposide or teniposide, a proteasome inhibitor such as bortezomib or anti-inflammatory drugs such as celecoxib or rofecoxib, optionally in form of the pharmaceutically acceptable salts, in form of the hydrates and/or solvates and optionally in the form of the individual optical isomers, mixtures of the individual enantiomers or racemates thereof.

In some cases, chemotherapeutic agent may include but is not limited to a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, an antagonist of the mitogen-activated protein kinase such as BAY-43-9006 or BAY-57-9006, a quinazoline derivative such as 4-[(3-chloro-4-fluorophenyl)amino]-6-{[4-(N,N-dimethylamino)-1-oxo-2-bute-n-1-yl]amino}-7-((S)-tetrahydrofuran-3-yloxy) quinazoline or 4-[(3-chloro-4-fluoro-phenyl)amino]-6-{[4-(homomorpholin-4-yl)-1-oxo-2-bu-ten-1-yl]amino}-7-[(S)-(tetrahydrofuran-3-yl)oxy]-quinazoline, or a pharmaceutically acceptable salt thereof, a protein kinase receptor antagonist which is not classified under the synthetic small molecules such as atrasentan, rituximab, cetuximab, Avastin™ (bevacizumab), IMC-1C11, erbitux (C-225), DC-101, EMD-72000, vitaxin, imatinib, a protein tyrosine kinase inhibitor which is a fusion protein such as VEGFtrap, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), pemetrexed, tegafur/uracil, uracil mustard, fludarabine, gemcitabine, capecitabine, mercaptopurine, cladribine, thioguanine, methotrexate, pentostatin, hydroxyurea, or folic acid, a phleomycin, a bleomycin or a derivative or salt thereof, CHPP, BZPP, MTPP, BAPP, liblomycin, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, an anti-cancer drug from plants such as paclitaxel (taxol), docetaxel or taxotere, a vinca alkaloid such as navelbine, vinblastin, vincristin, vindesine or vinorelbine, a tropolone alkaloid such as colchicine or a derivative thereof, a macrolide such as maytansine, an ansamitocin or rhizoxin, an antimitotic peptide such as phomopsin or dolastatin, an epipodophyllotoxin or a derivative of podophyllotoxin such as etoposide or teniposide, a steganacin, an antimitotic carbamate derivative such as combretastatin or amphetinile, procarbazine, a proteasome inhibitor such as bortezomib, an enzyme such as asparaginase, pegylated asparaginase (pegaspargase) or a thymidinephosphorylase inhibitor, a gestagen or an estrogen such as estramustine (T-66) or megestrol, an anti-androgen such as flutamide, casodex, anandron or cyproterone acetate, an aromatase inhibitor such as aminoglutethimide, anastrozole, formestan or letrozole, a GNrH analogue such as leuprorelin, buserelin, goserelin or triptorelin, an anti-estrogen such as tamoxifen or its citrate salt, droloxifene, trioxifene, raloxifene or zindoxifene, a derivative of 17β-estradiol such as ICI 164,384 or ICI 182,780, aminoglutethimide, formestane, fadrozole, finasteride, ketoconazole, a LH-RH antagonist such as leuprolide, a steroid such as prednisone, prednisolone, methylprednisolone, dexamethasone, budenoside, fluocortolone or triamcinolone, an interferon such as interferon β, an interleukin such as IL-10 or IL-12, an anti-TNFα antibody such as etanercept, an immunomodulatory drug such as thalidomide, its R- and S-enantiomers and its derivatives, or revimid (CC-5013), a leukotrien antagonist, mitomycin C, an aziridoquinone such as BMY-42355, AZQ or EO-9, a 2-nitroimidazole such as misonidazole, NLP-1 or NLA-1, a nitroacridine, a nitroquinoline, a nitropyrazoloacridine, a "dual-function" nitro aromatic such as RSU-1069 or RB-6145, CB-1954, a N-oxide of nitrogen mustard such as nitromin, a metal complex of a nitrogen mustard, an anti-CD3 or anti-CD25 antibody.

In some cases, the chemotherapeutic agent is selected from the group consisting of compounds interacting with or binding tubulin, synthetic small molecule VEGF receptor antagonists, small molecule growth factor receptor antagonists, inhibitors of the EGF receptor and/or VEGF receptor and/or integrin receptors or any other protein tyrosine kinase receptors which are not classified under the synthetic small-molecules, inhibitors directed to EGF receptor and/or VEGF receptor and/or integrin receptors or any other protein tyrosine kinase receptors, which are fusion proteins, compounds which interact with nucleic acids and which are classified as alkylating agents or platinum compounds, compounds which interact with nucleic acids and which are classified as anthracyclines, as DNA intercalators or as DNA cross-linking agents, including DNA minor-groove binding compounds, anti-metabolites, naturally occurring, semi-synthetic or synthetic bleomycin type antibiotics, inhibitors of DNA transcribing enzymes, and especially the topoisomerase I or topoisomerase II inhibitors, chromatin modifying agents, mitosis inhibitors, anti-mitotic agents, cell-cycle inhibitors, proteasome inhibitors, enzymes, hormones, hormone antagonists, hormone inhibitors, inhibitors of steroid biosynthesis, steroids, cytokines, hypoxia-selective cytotoxins, inhibitors of cytokines, lymphokines, antibodies directed against cytokines, oral and parenteral tolerance induction agents, supportive agents, chemical radiation sensitizers and protectors, photo-chemically activated drugs, synthetic poly- or oligonucleotides, optionally modified or conjugated, non-steroidal anti-inflammatory drugs, cytotoxic antibiotics, antibodies targeting the surface molecules of cancer cells, antibodies targeting growth factors or their receptors, inhibitors of metalloproteinases, metals, inhibitors of oncogenes, inhibitors of gene transcription or of RNA translation or protein expression, complexes of rare earth elements, and photo-chemotherapeutic agents.

In some cases, the chemotherapeutic agent is selected from the group consisting of paclitaxel (taxol), docetaxel, a vinca alkaloid such as navelbine, vinblastin, vincristin, vindesine or vinorelbine, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an immunomodulatory drug such as thalidomide, its R- and S-enantiomers and its derivatives, or revimid (CC-5013)), an ethyleneimine compound, an alkylsulphonate, daunorubicin, doxorubicin (adriamycin), liposomal doxflubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), uracil mustard, fludarabine, gemcitabine, capecitabine, mercaptopurine, cladribine, thioguanine, methotrexate, pentostatin, hydroxyurea, or folic acid, an acridine or a derivative thereof, a rifamycin, an actinomycin, adramycin, a camptothecin such as irinotecan (camptosar) or topotecan, an amnsacrine or analogue thereof, a tricyclic carboxamide, an histonedeacetylase inhibitor such as SAHA, MD-275, trichostatin A, CBHA, LAQ824, or valproic acid, or a proteasome inhibitor such as bortezomib.

In some cases, the chemotherapeutic agent is a compound which reduces the transport of hyaluronan mediated by one or more ABC transporters, or drug transport inhibitor, such as a P-glycoprotein (P-gp) inhibitor molecule or inhibitor peptide, an MRP 1 inhibitor, an antibody directed against and capable of blocking the ABC transporter, an antisense oligomer, iRNA, siRNA or aptamer directed against one or more ABC transporters. Examples of P-glycoprotein (P-gp) inhibitor molecules in accordance with the present disclosure are zosuquidar (LY 335973), its salts (especially the trichloride salt) and its polymorphs, cyclosporin A (also known as cyclosporine), verapamil or its R-isomer, tamoxifen, quinidine, d-alpha tocopheryl polyethylene glycol 1000 succinate, VX-710, PSC833, phenothiazine, GF120918 (II), SDZ PSC 833, TMBY, MS-073, S-9788, SDZ 280-446, XR(9051) and functional derivatives, analogues and isomers of these.

ii. Haptens and Scaffolds

Ensembles comprising a plurality of antigen variants may also comprise additional components. In some instances, antigen variants may be further derivatized to include a hapten. Haptens, or small, low molecular weight molecules may be attached to antigens, or in particular one or more epitopes on a particular antigen variant. As known in the art, haptens may be any low molecular weight molecule or moiety. In some cases, a hapten may comprise a phosphate group linked an amino acid. This may include but is not limited to phosphothreonine or phosphotyrosine. In some cases, artificial amino acids phosphothreonine and phosphotyrosine or mimics of phosphothreonine and phosphotyrosine may be incorporated directly into the antigen variant. IN some cases these haptens may be in or around the target epitope.

In other cases, haptens may be drugs or small molecules which may be crosslinked or affinity bound to the antigen variant, or target epitope on the antigen variant. In some cases, haptens may include but are not limited to drugs such as hallucinogens, for example mescaline and LSD; cannabinoids, for example THC; dissociative drugs such as PCP/phencyclidine and ketamine; stimulants, for example amphetamines, cocaine, phenmetrazine, methylphenidate; nicotine; depressants, for example, nonbarbiturates (e.g. bromides, chloral hydrate etc.), methaqualone, barbiturates, diazepam, flurazepam, phencyclidine, and fluoxetine; opium and its derivatives, for example, heroin, methadone, morphine, meperidine, codeine, pentazocine, and propoxyphene; prescription drugs including opioids (for pain), central nervous system depressants (for anxiety and sleep disorders), and stimulants (for ADHD and narcolepsy). Opioids include hydrocodone (Vicodin®), oxycodone (OxyContin®), propoxyphene (Darvon®), hydromorphone (Dilaudid®), meperidine (Demerol®), and diphenoxylate (Lomotil®). Central nervous system depressants include barbiturates such as pentobarbital sodium (Nembutal®), and benzodiazepines such as diazepam, (Valium®) and alprazolam (Xanax®). Stimulants include dextroamphetamine (Dexedrine®), methylphenidate (Ritalin® and Concerta®), and amphetamines (Adderall®); club drugs include GHB, Rohypnol®, ketamine, and others; and "designer drugs" such as "ecstasy."

Further, antigen variants, may be bound or fused to additional molecules or proteins known as scaffolds. Generally scaffolds include molecules which themselves are not immunogenic, but provide suitable platform on which to express or attach various antigen variants. For example, phage coat proteins may be considered scaffold proteins. In some cases, antigen variants may be irreversibly or reversibly linked to phage coat proteins. In other cases, scaffolds may other proteins such as other viral coat proteins, protein complexes capable of oligomerization. In some cases, scaffolds may be other organic or inorganic molecules which may polymerize, such as dendrimers. In some cases, scaffolds may be useful for immunogenic composition such as vaccines, whereby the immunogen (i.e immunogenic composition comprising the ensemble) is concentrated in a single molecule, rather than dispersed.

iii. DNA Based Formulations

In some cases, the immunogenic composition of the disclosure may comprise nucleic acids encoding the antigen variant proteins of the immunogenic composition. In some cases, nucleic acids may be administered to a subject or immune cell rather than purified proteins. In some cases, a subject or immune cell generates the antigen variant protein from nucleic acids delivered to the subject or immune cell The compositions and methods of the disclosure provide for any suitable delivery vector of antigen variant encoding nucleic acids to cells in a human subject or patient in need thereof.

In some cases, delivery of the nucleic acid may be performed using any suitable "vector" (sometimes also referred to as "gene delivery" or "gene transfer vehicle). Vector, delivery vehicle, gene delivery vehicle or gene transfer vehicle, may refer to any suitable macromolecule or complex of molecules comprising a polynucleotide to be delivered to a target cell. In some cases, a target cell may be any cell to which the nucleic acid or gene is delivered.

For example, suitable vectors may include but are not limited to, viral vectors such as adenoviruses, adeno-associated viruses (AAV), and retroviruses, liposomes, other lipid-containing complexes, and other macromolecular complexes capable of mediating delivery of a polynucleotide to a target cell.

In some cases, a vector may be an organic or inorganic molecule. In some cases, a vector may be small molecule (i.e. <5 kD), or a macromolecule (i.e. >5 kD). For example a vector may include but is not limited to inert, non-biologically active molecules such as metal particles. In some cases, a vector may be gold particles.

In some cases a vector may comprise a biologically active molecule. For example, vectors may comprise polymerized macromolecules such as dendrimers.

In some cases, a vector may comprise a recombinant viral vector that incorporates one or more nucleic acids. As described herein, nucleic acids may refer to polynucleotides. Nucleic acid and polynucleotide may be used interchangeably. In some cases nucleic acids may comprise DNA or RNA. In some cases RNA nucleic acids may include but are not limited to a transcript of a gene of interest (e.g. antigen variant sequence), intronsuntranslated regions, termination sequences and the like. In other cases, DNA nucleic acids may include but are not limited to sequences such as hybrid promoter gene sequences, strong constitutive promoter sequences, the antigen variant of interest, untranslated regions, termination sequences and the like. In some cases, a combination of DNA and RNA may be used.

As described in the disclosure herein, the term "expression construct" is meant to include any type of genetic construct containing a nucleic acid or polynucleotide coding for gene products in which part or all of the nucleic acid encoding sequence is capable of being transcribed. The transcript may be translated into a protein. In some cases it may be partially translated or not translated. In certain aspects, expression includes both transcription of a gene and translation of mRNA into a gene product. In other aspects, expression may only include transcription of the nucleic acid encoding antigen variants of the immunogenic composition.

In some cases, a plurality of nucleic acids may be delivered by suitable vectors, each nucleic acid encoding one or more antigen members or variants of the immunogenic composition. Individual concentrations of antigen member proteins may be controlled by suitable expression control elements, such as promoters, enhancers, repressors and the like. In some instances, the administration of nucleic acids to generate antigen variant proteins of an immunogenic composition in a subject or immune cell may be referred to as a "nucleic acid vaccine."

iv. General Formulation Methods

Generally, the immunogenic compositions of this disclosure may be purified from culture supernatant using a process wherein the clarified supernatant (obtained by centrifugation) is captured on any combination of columns selected from (without being limiting) affinity chromatography resin such as Protein A resin, Cation Exchange Chromatography (CIEC) or an Anion Exchange Chromatography (AIEC) using for example Poros SOHS (FORDS), SOURCE 30S or SOURCE 15S (GE Healthcare), SP Sepharose (GE Healthcare), Capto S (GE Healthcare), Capto MMC (GE Healthcare) or Poros 50HQ (POROS), SOURCE 30Q or SOURCE 15Q (GE Healthcare), Q Sepharose (GE Healthcare), Capto Q and DEAE Sepharose (GE Healthcare), Size exclusion chromatography (SE-HPLC) using for example Superdex 75 or Superdex 200 (GE Healthcare), hydrophobic interaction chromatography (HIC) using for example octyl, butyl sepharose or equivalents, optionally also including a tangential flow filtration (TFF) step. Any combination of columns can be used for the purification of the polypeptides of the invention, such as e.g. Protein A resin followed by Cation Exchange Chromatography or two Cation Exchange Chromatography steps.

The present invention also provides methods for preparing the stable formulations of the invention comprising the ensembles of the invention. More particularly, the present invention provides methods for preparing stable formulations of such ensembles, said methods comprising concentrating a fraction containing the purified antigen variants to a final concentration of more than 30 mg/ml, 40 mg/ml, 50 mg/ml, 60 mg/ml, 70 mg/ml, 80 mg/ml, 90 mg/ml, 100 mg/ml, or 150 mg/ml, such as e.g. 65 mg/ml using a semipermeable membrane with an appropriate molecular weight (MW) cutoff and diafiltering and/or ultrafiltering to buffer exchange and further concentrate the polypeptide fraction into the formulation buffer using the same membrane.

The pH of the formulation may range from 3.0 to about 12.0. The pH of the immunogenic composition may be at least 3, 4, 5, 6, 7, 8, 9, 10, 11 or 12 pH units. The pH of the immunogenic composition may be at most 3, 4, 5, 6, 7, 8, 9, 10, 11 or 12 pH units.

The formulations of the present invention may be sterilized by various sterilization methods, including sterile filtration, radiation, etc. In a specific embodiment, the polypeptide formulation is filter-sterilized with a presterilized 0.2 micron filter.

The formulations of the invention may be lyophilized (freeze dried) if desired. Accordingly, the invention also encompasses lyophilized forms of the formulations of the invention. Preferably the final residual water content of the lyophilized formulation is extremely low, around 1% to 4%.

The formulations of the invention may also be spray dried if desired. Accordingly, the invention also encompasses spray dried forms of the formulations of the invention. Preferably the final residual water content of the spray dried formulation is extremely low, around 1% to 4%.

Spray drying is a method of producing a dry powder from a liquid or slurry by rapidly drying with a hot gas. Spray drying works by dispersing the liquid formulation into a controlled drop size spray and passing hot air as the heated drying media.

In some cases, the liquid, lyophilized or spray dried formulation of the present invention is supplied in a hermetically sealed container. Liquid formulations may comprise a quantity between 1 ml and 20 ml. In some cases, liquid formulations may be at least 1 ml, 2 ml, 3 ml, 4 ml, 5 ml, 6 ml, 7 ml, 8 ml, 9 ml, 10 ml, 15 ml, or 20 ml.

The liquid, lyophilized or spray dried formulations of the present invention can be prepared as unit dosage forms by preparing a vial containing an aliquot of the liquid, lyophilized or spray dried formulation for a one time use. For example, a unit dosage of liquid formulation per vial may contain 1 ml, 2 ml, 3 ml, 4 ml, 5 ml, 6 ml, 7 ml, 8 ml, 9 ml, 10 ml, 15 ml, or 20 ml of the formulation. In a preferred aspect, the unit dosage form is suitable for subcutaneous administration to a subject. In another aspect, the subject is a human.

The amount of a formulation of the present invention which will be effective in the prevention, treatment and/or management of a certain disease or disorder can be determined by standard clinical techniques well-known in the art or described herein, The precise dose to be employed in the formulation will also depend on the route of administration, and should be decided according to the judgment of the practitioner and each patient's circumstances. Effective doses may be extrapolated from dose-response curves derived from in vitro or animal model test systems. For formulations of the polypeptide, encompassed by the invention, the dosage administered to a patient may further be calculated using the patient's weight in kilograms (kg) multiplied by the dose to be administered in mg/kg.

The required volume (in ml) to be given is then determined by taking the mg dose required divided by the concentration of the polypeptide formulation. The final calculated required volume will be obtained by pooling the contents of as many vials as are necessary into syringe(s) to administer the polypeptide formulation of the invention.

The present invention also encompasses a finished packaged and labeled pharmaceutical product. This article of manufacture or kit includes the appropriate unit dosage form in an appropriate vessel or container such as a glass vial or other container that is hermetically sealed. In one embodiment, the unit dosage form is suitable for intravenous, intramuscular, intranasal, oral, topical or subcutaneous delivery. Thus, the invention encompasses formulations, preferably sterile, suitable for each delivery route. In the case of dosage forms suitable for parenteral administration (such as e.g. subcutaneous administration) the active ingredient, e.g., polypeptide of the invention is sterile and suitable for administration as a particulate free solution. In other words, the invention encompasses both parenteral solutions and lyophilized or spray dried powders, each being sterile, and the latter being suitable for reconstitution prior to injection.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises the formulation containing the polypeptide. The packaging material includes instruction means which indicate that said polypeptide can be used to prevent, treat and/or manage one or more symptoms associated with the disease or disorder by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a formulation containing the polypeptide of interest, and wherein said packaging material includes instruction means which indicate that said agents can be used to prevent, treat and/or manage the disease or disorder by administering specific doses and using specific dosing regimens as described herein.

The formulations, containers, pharmaceutical unit dosages and kits of the present invention may be administered to a subject to prevent, treat and/or manage a specific disease and/or disorder in subject in need thereof.

V. Administration of the Immunogenic Composition

After an immunogenic composition is formulated from an ensemble of a plurality of antigen variants and other optional components as described herein, the immunogenic composition may be administered to a subject, animal or cell to induce an immune response.

The pharmaceutical unit dosage forms can be made suitable for any form of delivery of the polypeptide of the invention including (without being limiting) parenteral delivery, topical delivery, pulmonary delivery, intranasal delivery, vaginal delivery, enteral delivery, rectal delivery, oral delivery and/or sublingual delivery. In one aspect, the present invention relates to a pharmaceutical unit dosage form suitable for parenteral (such as e.g. intravenous, intraarterial, intramuscular, intracerebral, intraosseous, intradermal, intrathecal, intraperitoneal, subcutaneous, etc) administration to a subject, comprising a formulation of the invention in a suitable container. In some cases, an immunogenic composition may be administered at least 1, 2, 3, 4, 5, 6, 7, 8, 9, 10 or 20 times to a subject. In some cases, an immunogenic composition may be administered at most 1, 2, 3, 4, 5, 6, 7, 8, 9, 10 or 20 times to a subject.

Generally, any animal that possesses an immune system may be used to administer an immunogenic composition. For example an immunogenic composition of the disclosure may be administered to a human, a non-human primate, livestock, a mammal, a bovine, equine, porcine, ovine, caprine, feline, canine, buffalo, guinea pig, hamster, rabbit, mice, fish, shark, bird or reptile subject.

Administering an immunogenic composition of this disclosure to an animal or subject may be performed for a variety of reasons. In some cases, immunogenic compositions may be administered as a vaccine or for therapeutic applications as described herein.

In some cases, the immunogenic composition may also used to harvest antibodies from a host animal. In some cases, animals just as goats, mice, rodents, chickens and rabbits may be used specifically for antibody harvest and purification as described in the art. In some cases, one or more of these animals may be administered the immunogenic composition. In some cases, the host immune response generates circulating antibodies in the serum of these animals. Harvesting the serum of these animals may be useful in generating and isolating an antibody of interest.

In some cases, an immunogenic composition may be administered or used to expose an immune cell. In some cases, cultured immune cells, such as T cell, B cell, dendritic cells, antigen presenting cells, or any suitable immune cell, may be cultured and exposed to immunogenic composition in vitro. In this case, the immune cell may elicit an immune response to the immunogenic composition in vitro. In some cases, immune cells may comprise a cultured cell line. In some cases immune cells may be extracted and harvested from a patient. As described herein, the methods and compositions of the disclosure may be used to "train" immune cells of a subject, such as used in a therapeutic application. In some cases, immune cells may be isolated and extracted from a subject, contacted with an immunogenic composition as provided by the disclosure, and returned to the subject.

In another example, immune cells may be used to test the immunogenic response of the immunogenic composition. As described herein, techniques such as FACS may be used to test the specificity and/or immunogenicity of a plurality of antigen variants when contacted with immune cells such as B cells.

In another example, such as with a hybridoma, or immortalized B cell, this cell results from a fusion between a B cell and an immortalized cell line such as cancer cell line, and may be used. An immunogenic composition may be applied to a culture of hybridomas. In some cases, recognition of the target epitope by one or more hybridoma cells may elicit an immune response in the form on antibody production. In some cases, antibodies produced in this way may be purified and used. Generally, any immune cell may be used in this manner. In some instances, exposure to an immune cell may be used to test an immunogenic composition, or in some cases it may be used to elicit a response for isolation of a particular antibody to target epitope.

IV. Applications

A. Vaccine Development i. Vaccine Strategies

The composition and methods of this disclosure provide for numerous applications. One important application is the development of improved vaccines towards any pathogenic, cancer, autoimmune antigens or small molecules, such as drugs.

In some cases, an antigen may be derived (e.g., selected) from a pathogenic organism. In some cases, the antigen is a cancer or tumor antigen, e.g., an antigen derived from a tumor or cancer cell.

In some cases, an antigen derived from a pathogenic organism is an antigen associated with an infectious disease; it can be derived from any of a variety of infectious agents, including virus, bacterium, fungus or parasites.

In some cases, a target antigen is any antigen associated with a pathology, for example an infectious disease or pathogen, or cancer or an immune disease, inflammatory disease, addiction disease, neurological disease, or autoimmune disease. In some cases, an antigen can be expressed by any of a variety of infectious agents, including virus, bacterium, fungus or parasite. A target antigen for use in the methods and compositions as disclosed herein can also include, for example, pathogenic peptides, toxins, toxoids, subunits thereof, or combinations thereof (e.g., cholera toxin, tetanus toxoid).

The present disclosure provides for a plurality of antigen variants selected from a computation-guided library. In some cases, vaccines of the disclosure may also comprise recombinant proteins or peptides, carbohydrates, glycoproteins, glycopeptides, proteoglycans, inactivated organisms, and viruses, dead organisms and virus, genetically altered organisms or viruses, or cell extracts. In some aspects, an immunogenic composition may comprise nucleic acids, carbohydrates, lipids, and/or small molecules. In some aspects, an immunogenic composition is one that elicits an immune response. In other aspects, an immunogenic composition is a polynucleotide that encodes a protein or peptide that when the protein or peptide is expressed an immune response is elicited. In some aspects, an immunogenic composition is an antigen. In some aspects, an immunogenic composition is a protein or peptide. In some aspects, an immunogenic composition is used for vaccines.

Any of the antigens described herein may be in the form of whole killed organisms, peptides, proteins, glycoproteins, glycopeptides, proteoglycans, nucleic acids that encode a protein or peptide, carbohydrates, small molecules, or combinations thereof. In some aspects, an immunogenic composition is derived from a microorganism for which at least one vaccine already exists. In some aspects, an immunogenic composition is derived from a microorganism for which no vaccines have been developed.

In some aspects, an immunogenic composition or vaccine of the disclosure comprises two types of antigens which are both derived from a single genus of microorganism. In some aspects, an immunogenic composition or vaccine of the disclosure comprises two types of immunogenic compositions which are both derived from a single genus and species of microorganism. In some aspects, an immunogenic composition or vaccine of the disclosure comprises two types of antigens which are both derived from a single genus, species, and strain of microorganism. In some aspects, a immunogenic composition or vaccine of the disclosure comprises two types of antigens which are both derived from a single clone of a microorganism.

In some aspects, an immunogenic composition or vaccine of the disclosure comprises two or more types of antigens which are derived from different strains of a single species of microorganism. In some aspects, an immunogenic composition or vaccine of the disclosure comprises two or more types of antigens which are derived from different species of the same genus of microorganism. In other aspects, an immunogenic composition or vaccine of the disclosure comprises two or more types of antigens each derived from different genera of microorganism.

In some aspects, a immunogenic composition or vaccine of the disclosure comprises a single type of antigen that elicits an immune response in both B cells and T cells. In some aspects, an immunogenic composition or vaccine of the disclosure comprises two types of antigens, wherein the first immunogenic composition stimulates B cells, and the second type of antigen stimulates T cells. In some aspects, one or both antigens may stimulate T cells and B cells. In some aspects, an immunogenic composition or vaccine of the disclosure comprises greater than two types of antigens, wherein one or more types of antigens stimulate B cells, and one or more types of antigens stimulate T cells.

In some aspects, the immunogenic composition comprises a T cell antigen or plurality of antigen variants, and the T cell antigen is derived from the same pathogen against which vaccination is intended. In this case, an initially small number of naive T cells are stimulated to generate pathogen-specific effector and memory T cells. In some aspects, the antigen may be taken from an unrelated source, such as an infectious agent to which wide-spread immunity already exists (e.g., tetanus toxoid or a common component of influenza virus, such as hemagglutinin, neuraminidase, or nuclear protein). In the latter case, the vaccine exploits the presence of memory T cells that have arisen in response to prior infections or vaccinations. Memory cells in general react more rapidly and vigorously to antigen rechallenge and, therefore, may provide a superior source of help to B cells.

Other antigens include, but are not limited to, degenerative disease antigens, infectious disease antigens, cancer antigens, allergens, alloantigens, atopic disease antigens, autoimmune disease antigens, contact sensitizers, haptens, xenoantigens, or metabolic disease enzymes or enzymatic products thereof and as described herein.

ii. Antigen Selection

In some cases, a vaccine may be developed using the composition and methods of the disclosure, to antigens selected from Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), Marek's disease virus, herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions and methods described herein are contemplated for use in treating infections with these viral agents.

In some cases, a vaccine may be developed using the composition and methods of the disclosure, to antigens selected from fungal pathogens which include but are not limited to aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans*. Components of these organisms can be included as antigens in the MAPS described herein.

In some cases, a vaccine may be developed, using the compositions and methods of the disclosure, to antigens selected from infectious microbes including but not limited to *Bordatella pertussis, Brucella, Enterococci* sp., *Neisseria meningitidis, Neisseria gonorrheae, Moraxella*, typeable or nontypeable *Haemophilus, Pseudomonas, Salmonella, Shigella, Enterobacter, Citrobacter, Klebsiella, E. coli, Helicobacter pylori, Clostridia, Bacteroides, Chlamydiaceae, Vibrio cholera, Mycoplasma, Treponemes, Borelia burgdorferi, Legionella pneumophilia, Mycobacteria* sps (such as *M. tuberculosis, M. avium, M. intracellular e, M. kansaii, M. gordonae, M. leprae), Staphylococcus aureus, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Leptospira sps., Pasteurella multocida, Bacteroides* sp., *Fusobacterium nucleatum, Streptobacillus moniliformis, Treponema pallidum, Treponema pertenue*, and *Actinomyces israelii*. The compositions and methods described herein are contemplated for use in treating or preventing infections against these bacterial agents.

Additional parasite pathogens from which antigens can be derived include, for example: *Entamoeba histolytica, Plasmodium falciparum, Leishmania* sp., *Toxoplasma gondii, Rickettsia*, and the Helminths.

In some cases, a vaccine may be developed, using the compositions and methods of the disclosure, to antigens selected from a truncated pneumococcal PsaA protein, pneumolysin toxoid pneumococcal serine/threonine protein kinase (StkP), pneumococcal serine/threonine protein kinase repeating unit (StkPR), pneumococcal PcsB protein, staphylococcal alpha hemolysin, *Mycobacterium tuberculosis* mtb protein ESAT-6, *M. tuberculosis* cell wall core antigen, *Chlamydia* CT144, CT242 or CT812 polypeptides or fragments of these, *Chlamydia* DNA gyrase subunit B, *Chlamydia* sulfite synthesis/biphosphate phosphatase, *Chlamydia* cell division protein FtsY, *Chlamydia* methionyl-tRNA synthetase, *Chlamydia* DNA helicase (uvrD), *Chlamydia* ATP synthase subunit I (atpI), or *Chlamydia* metal dependent hydrolase.

In some cases, a vaccine may be developed, using the compositions and methods of the disclosure, to antigens selected from the pathogen Myocobacterium tuberculosis (TB), an intracellular bacterial parasite. One example of a TB antigen is TbH9 (also known as Mtb 39A). Other TB antigens include, but are not limited to, DPV (also known as Mtb8.4), 381, Mtb41, Mtb40, Mtb32A, Mtb64, Mtb83, MA9.9A, Mtb9.8, Mtbl6, Mtb72f, Mtb59f, Mtb88f, Mtb71f, Mtb46f and Mtb31 f, wherein "f" indicates that it is a fusion or two or more proteins.

In some cases, a vaccine may be developed, using the compositions and methods of the disclosure, to antigens selected from *Chlamydia* species for use in the immunogenic compositions of the present disclosure. Chlamydiaceae (consisting of Chlamydiae and *Chlamydophila*), are obligate intracellular gram-negative bacteria. *Chlamydia trachomatis* infections are among the most prevalent bacterial sexually transmitted infections, and perhaps 89 million new cases of genital chlamydial infection occur each year. The *Chlamydia* of the present disclosure include, for example, *C. trachomatis, Chlamydophila pneumoniae, C muridarum, C. suis, Chlamydophila abortus, Chlamydophila psittaci, Chlamydophila caviae, Chlamydophila felis, Chlamydophila pecorum*, and *C pneumoniae*. Animal models of chlamydial infection have established that T-cells play a critical role both in the clearance of the initial infection and in protection from re-infection of susceptible hosts. Hence, the immunogenic compositions as disclosed herein can be used to provide particular value by eliciting cellular immune responses against chlamydial infection.

More specifically, Chlamydial antigens useful in the present disclosure include DNA gyrase subunit B, sulfite synthesis/biphosphate phosphatase, cell division protein FtsY, methionyl-tRNA synthetase, DNA helicase (uvrD); ATP synthase subunit I (atpI) or a metal-dependent hydrolase (U.S. Patent Application Pub. No. 20090028891). Additional *Chlamydia trachomatis* antigens include CT144 polypeptide, a peptide having amino acid residues 67-86 of CT144, a peptide having amino acid residues 77-96 of CT144, CT242 protein, a peptide having amino acids 109-117 of CT242, a peptide having a mino acids 112-120 of CT242 polypeptide, CT812 protein (from the pmpD gene), a peptide having amino acid residues 103-111 of the CT812 protein; and several other antigenic peptides from *C trachomatis*:

In some cases, a vaccine may be developed, using the compositions and methods of the disclosure, to antigens selected from fungal antigens derived from *Candida* species and other yeast; or other fungi (*aspergillus*, other environmental fungi). Regarding other parasites, malaria as well as worms and amoebae may provide the antigenic antigen for use in the in the immunogenic compositions and methods as disclosed herein.

In some cases, an antigen for use in the immunogenic compositions as disclosed herein can also include those used in biological warfare, such as ricin, which may provoke an immune response.

Additionally, the present disclosure also provides immunogenic compositions comprising antigens which raise an immune response against cancer. In these conjugates, an antigen is an antigen expressed by a cancer or tumor, or derived from a tumor. In some cases, such antigens are referred to herein as a "cancer antigen" and are typically a protein expressed predominantly on the cancer cells, such that the conjugate elicits both potent humoral and potent cellular immunity to this protein. A large number of cancer-associated antigens have been identified, several of which are now being used to make experimental cancer treatment vaccines and are thus suitable for use in the present cases. Antigens associated with more than one type of cancer include Carcinoembryonic antigen (CEA); Cancer/testis antigens, such as NY-ESO-1; Mucin-1 (MUC 1) such as Sialyl Tn (STn); Gangliosides, such as GM3 and GD2; p53 protein; and HER2/neu protein (also known as ERBB2). Antigens unique to a specific type of cancer include a mutant form of the epidermal growth factor receptor, called EGFRvIII; Melanocyte/melanoma differentiation antigens, such as tyrosinase, MARTI, gplOO, the lineage related cancer-testis group (MAGE) and tyrosinase-related antigens; Prostate-specific antigen; Leukaemia-associated antigens (LAAs), such as the fusion protein BCR-ABL, Wilms' tumour protein and proteinase 3; and Idiotype (Id) antibodies. See, e.g., Mitchell, 3 Curr. Opin. Investig. Drugs 150 (2002); Dao & Scheinberg, 21 Best Pract. Res. Clin. Haematol. 391 (2008).

Another approach in generating an immune response against cancer employs antigens from microbes that cause or contribute to the development of cancer. These vaccines have been used against cancers including hepatocellular carcinoma (hepatitis B virus, hepatitis C virus, *Opisthorchis viverrin*), lymphoma and nasoparyngeal carcinoma (Epstei-Barr virus), colorectal cancer, stomach cancer (*Helicobacter pylori*), bladder cancer (Schisosoma hematobium), T-cell leukemia (human T-cell lymphtropic virus), cervical cancer (human papillomavirus), and others. To date, there have been clinical trials for vaccines targeting Bladder Cancer, Brain Tumors, Breast Cancer, Cervical Cancer, Kidney Cancer, Melanoma, Multiple Myeloma, Leukemia, Lung Cancer, Pancreatic Cancer, Prostate Cancer, and Solid Tumors. See Pardoll et al., ABELOFF S CLIN. ONCOL. (4th ed., Churchill Livingstone, Philadelphia 2008); Sioud, 360 Methods Mol. Bio. 277 (2007); Pazdur et al., 30 J. Infusion Nursing 30(3): 173 (2007); Parmiani et al., 178 J. Immunol. 1975 (2007); Lollini et al., 24 Trends Immunol. 62 (2003); Schlom et al., 13 Clin. Cancer Res. 3776 (2007); Banchereau et al., 392 Nature 245 (1998); Finn, 358 New Engl. J. Med. 2704 (2008); Curigliano et al., 7 Exp. Rev. Anticancer Ther. 1225 (2007). Marek's Disease virus, a herpes virus that causes tumors in poultry, has long been managed by vaccine. Thus, the present cases encompass both preventive or prophylactic anti-cancer immunogenic compositions and treatment/therapeutic cancer vaccines.

In some cases, a vaccine may be developed, using the compositions and methods of the disclosure, to antigens associated with proliferative diseases and cancers which include AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, astrocytoma, ataxia-telangiectasia, basal cell carcinoma (skin), bladder cancer, bone cancers, bowel cancer, brain and CNS tumors, breast cancer, carcinoid tumors, cervical cancer, childhood brain tumours, childhood cancer, childhood leukemia, childhood soft tissue sarcoma, chondrosarcoma, choriocarcinoma, chronic lymphocytic leukemia, chronic myeloid leukemia, colorectal cancers, cutaneous t-cell lymphoma, dermatofibrosarcoma-protuberans, desmoplastic-small-round-cell-tumour, ductal carcinoma, endocrine cancers, endometrial cancer, ependymoma, esophageal cancer, Ewing's sarcoma, extra-hepatic bile duct cancer, eye cancer, including, e.g., eye melanoma and retinoblastoma, fallopian tube cancer, fanconi anemia, fibrosarcoma, gall bladder cancer, gastric cancer, gastrointestinal cancers, gastrointestinal-carcinoid-tumour, genitourinary cancers, germ cell tumors, gestational-trophoblastic disease, glioma, gynecological cancers, hematological malignancies, hairy cell leukemia, head and neck cancer, hepatocellular cancer, hereditary breast cancer, Hodgkin's disease, human papillomavirus-related cervical cancer, hydatidiform mole, hypopharynx cancer, islet cell cancer, Kaposi's sarcoma, kidney cancer, laryngeal cancer, leiomyosarcoma, leukemia, Li-Fraumeni syndrome, lip cancer, liposarcoma, lung cancer, lymphedema, lymphoma, non-Hodgkin's lymphoma, male breast cancer, malignant-rhabdoid-tumour-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer-(NSCLC), oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumours, pituitary cancer, polycythemia vera, prostate cancer, renal cell carcinoma, retinoblastoma, rhabdomyosarcoma, Rothmund-Thomson syndrome, salivary gland cancer, sarcoma, Schwannoma, Sezary syndrome, skin cancer, small cell lung cancer (SCLC), small intestine cancer, soft tissue sarcoma, spinal cord tumours, squamous-cell-carcinoma-(skin), stomach cancer, synovial sarcoma, testicular cancer, thymus cancer, thyroid cancer, transitional-cell-cancer-(bladder), transitional-cell-cancer (renal-pelvis/ureter), trophoblastic cancer, urethral cancer, urinary system cancer, uterine sarcoma, uterus cancer, vaginal cancer, vulva cancer, Waldenstrom's-macroglobulinemia, and Wilms' tumor.

In some cases, a vaccine may be developed, using the compositions and methods of the disclosure, to antigens associated with autoimmune diseases, e.g., they can be "self-antigens." Autoimmune diseases contemplated for diagnosis according to the assays described herein include, but are not limited to alopecia areata, ankylosing spondylitis, antiphospholipid syndrome, Addison's disease, aplastic anemia, multiple sclerosis, autoimmune disease of the adrenal gland, autoimmune hemolytic anemia, autoimmune hepatitis, autoimmune oophoritis and orchitis, Behcet's Disease, bullous pemphigoid, cardiomyopathy, celiac sprue-dermatitis, chronic fatigue syndrome, chronic inflammatory demyelinating syndrome (CFIDS), chronic inflammatory polyneuropathy, Churg-Strauss syndrome, cicatricial pemphigoid, CREST Syndrome, cold agglutinin disease, Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), Lichen Planus, lupus, Meniere's Disease, mixed connective tissue disease, myasthenia gravis, myocarditis, pemphigus vulgaris, pernicious anemia, polyarteritis *nodosa*, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, stiff-man syndrome, Takayasu arteritis, temporal arteritis/giant cell arteritis, ulcerative colitis, uveitis, Wegener's syndrome, vasculitis and vitiligo. It is generally important to assess the potential or actual CMI responsiveness in subjects having, or suspected of having or being susceptible to an autoimmune disease.

In some cases, an antigen for use in the immunogenic compositions as disclosed herein can be an antigen which is associated with an inflammatory disease or condition. Examples of inflammatory disease conditions where antigens may be useful include but are not limited to acne, angina, arthritis, aspiration pneumonia, empyema, gastroenteritis, necrotizing enterocolitis, pelvic inflammatory disease, pharyngitis, pleurisy, chronic inflammatory demyelinating polyneuropathy, chronic inflammatory demyelinating polyradiculoneuropathy, and chronic inflammatory demyelinating polyneuropathy.

In some cases, an antigen for use in the immunogenic compositions as disclosed herein can be an antigen which is associated with an inflammatory disease or condition.

The compositions and methods of the present disclosure provide for vaccinations that may be either passive or active in nature. In general, active vaccinations may involve the exposure of a subject's immune system to one or more agents that are recognized as unwanted, undesired, and/or foreign and elicit an endogenous immune response resulting in the activation of antigen-specific naive lymphocytes that then give rise to antibody-secreting B cells or antigen-specific effector and memory T cells or both. This approach can result in long-lived protective immunity that may be boosted from time to time by renewed exposure to the same antigenic material, such as an immunogenic composition of the disclosure. In some cases, the compositions and methods of this disclosure may provide for a recipient or subject to be injected with preformed antibodies or with antigen-specific effector lymphocytes, which may confer rapid ad hoc protection, but generally do not establish persistent immunity.

Some current vaccines against, e.g., microbial pathogens, consist of live attenuated or non-virulent variant strains of microorganisms, or killed or otherwise inactivated organisms. Other vaccines utilize more or less purified components of pathogen lysates, such as surface carbohydrates or recombinant pathogen-derived proteins that are sometimes fused to other molecules, particularly proteins that can confer adjuvant activity. In some cases, one or more of the vaccine preparations may be used with the compositions and methods of the disclosure.

iii. Vaccination Process

Vaccines that utilize live attenuated or inactivated pathogens can, in some cases, yield a vigorous immune response, but their use may have limitations. For example, live vaccine strains can sometimes cause infectious pathologies, especially when administered to immune-compromised recipients. Moreover, many pathogens, particularly viruses, undergo continuous rapid mutations in their genome, which allow them to escape immune responses to antigenically distinct vaccine strains. However, most or all pathogens are thought to possess some antigenic determinants that are not easily mutated because they are associated with essential functions. Antibodies directed against these conserved epitopes, rather than more variable, non-essential epitopes can protect against highly mutable viruses (Baba et al, 2000, Nat. Med., 6:200; incorporated herein by reference) may be suitable target epitopes/target antigens as provided by the compositions and methods of the disclosure. Vaccines based on live or killed intact pathogens do not necessarily promote the recognition of these critical epitopes, but may essentially "distract" the immune system to focus its assault on highly variable determinants. In some cases the present disclosure provides for engineered vaccines that help an immune response focus on a particular immunogenic part of some antigens, and may present selectively essential, immutable or substantially immutable epitopes. In some cases, this may provide more potent and "escape-proof neutralizing antibody and effector T cell responses than intact microorganisms.

The precise mechanisms by which vaccines stimulate antibody responses in draining lymph nodes (or fail to do so) are complex. B and T cells may be initially sequestered in distinct anatomic regions, the superficially located B follicles and the surrounding paracortex and deep cortex, respectively in some mammalian systems. Upon antigen challenge, antigen-specific B cells in follicles as well as CD4 T cells in the T cell area may become activated and then migrate toward the border zone between the two compartments. B cells that have phagocytosed lymph-borne antigens process the acquired material and begin to present antigenic peptides in MHC class-II surface molecules that are then recognized by the activated CD4 T cells (the $TF_H$ cells). Antigen-recognition allows the $TF_H$ cells to provide help to B cells, which constitutes a potent survival signal and triggers the formation of germinal centers (GCs) within B follicles. The GC reaction promotes class-switch recombination, affinity maturation of antigen-specific antibodies, and the formation of memory B cells and long-lived plasma cells that can produce large amounts of high-affinity antibodies for extended periods of time. Thus, the present disclosure provides for an immunogenic composition or vaccine that may comprise components that allow antigenic material to be efficiently recognized by both B and T cells and in some cases to induce vigorous GC reactions.

Immunogenic compositions may be exposed to distinct cells of the immune system and stimulate them. In some aspects, immunogenic compositions of the present disclosure stimulate B cells, and immunogenic compositions may be processes by antigen-presenting cells (APCs), such as dendritic cells (DCs), in lymphoid tissues (and by B cells after activation) and presented to T cells.

In some aspects, immunogenic compositions may be modified such that the surface of one or more antigen variants may be attached or associated with a targeting moiety (e.g., antibody or fragment thereof, peptide or polypeptide, Affibody, Nanobody™, AdNectin™, Avimer™, aptamer, Spiegelmer, small molecule, lipid, carbohydrate, etc.). In some cases immunogenic compositions of the disclosure may be targeted to specific antigen presenting cells, such as DCs, SCS-Mph, FDCs, T Cells, B cells, and/or combinations thereof.

iv. Targeting Moieties for T Cells

In some aspects, vaccines of the present disclosure comprise at least one immunogenic composition which can be delivered to APCs, which then process and deliver the immunogenic composition(s) to T cells. Professional APCs are very efficient at internalizing antigen, either by phagocytosis or by endocytosis, and then display a fragment of the antigen, bound to either a class II major histocompatibility complex (class II MHC) molecule or a class I MHC molecule on the APC membrane. CD4 T cells recognize and interact with the antigen-class II MHC molecule complex on the APC membrane, whereas CD8 T cells recognize and interact with the antigen-class I MHC molecule complex. An additional co-stimulatory signal as well as modulating cytokines are then produced by the APC, leading to T cell activation.

In some aspects, immunogenic compositions comprise one or more targeting moieties. A targeting moiety is any moiety that binds to a component associated with an organ, tissue, cell, extracellular matrix, and/or subcellular locale. In some aspects, such a component is referred to as a "target" or a "marker," and these are discussed in further detail below.

A targeting moiety may be a nucleic acid, polypeptide, glycoprotein, carbohydrate, lipid, small molecule, etc. For example, a targeting moiety can be a nucleic acid targeting moiety (e.g. an aptamer, Spiegelmer®, etc.) that binds to a cell type specific marker. In general, an aptamer is an oligonucleotide (e.g., DNA, RNA, or an analog or derivative thereof) that binds to a particular target, such as a polypeptide. In some aspects, a targeting moiety may be a naturally occurring or synthetic ligand for a cell surface receptor, e.g., a growth factor, hormone, LDL, transferrin, etc. A targeting moiety can be an antibody, which term is intended to include antibody fragments, characteristic portions of antibodies, single chain antibodies, etc. Synthetic binding proteins such as Affibodies®, Nanobodies™, AdNectins™, Avimers™, etc., can be used. Peptide targeting moieties can be identified, e.g., using procedures such as phage display. This widely used technique has been used to identify cell specific ligands for a variety of different cell types.

In accordance with the present disclosure, a targeting moiety recognizes one or more "targets" or "markers" associated with a particular organ, tissue, cell, and/or subcellular locale. In some aspects, a target may be a marker that is exclusively or primarily associated with one or a few cell types, with one or a few diseases, and/or with one or a few developmental stages.

In some aspects, a target is a tumor marker. In some aspects, a tumor marker is an antigen that is expressed in tumor cells but not in healthy and/or normal cells. In some aspects, a tumor marker is an antigen that is more prevalent in tumor cells than in healthy and/or normal cells. Exemplary tumor markers include, but are not limited to, gp1OO; Melan-A; tyrosinase; PSMA; HER-2/neu; MUC-I; topoisomerase IIα; sialyl-Tn; carcinoembryonic antigen; ErbB-3-binding protein-1; alpha-fetoprotein; and the cancer-testis antigens MAGE-Al, MAGE A4, and NY-ESO-I.

In some aspects, a target is an APC marker. In some aspects, a target is a DC marker. In some aspects, a target is a T cell marker. In some aspects, a T cell target is an antigen that is expressed in T cells but not in non-T cells. In some aspects, a T cell target is an antigen that is more prevalent in T cells than in non-T cells.

In some aspects, targeting moieties are covalently associated with one or more antigen variants of an immunogenic composition of the disclosure. In some aspects, covalent association is mediated by a linker. In some aspects, targeting moieties are not covalently associated with an antigen variant. For example, targeting moieties may be associated with the surface of, encapsulated within, surrounded by, and/or distributed throughout the polymeric matrix of an inventive particle.

Dendritic Cells (DCs) are a type of myeloid leukocytes; they are among the most potent antigen presenting cells for T lymphocytes. Resting DCs reside in many tissues, including lymph nodes, in an immature, tolerogenic state, i.e., they present intermediate to high levels of peptide-MHC complexes, but with little or no costimulatory molecules and without secreting cytokines that T cells need to differentiate into effector cells. T cells that are presented with a specific antigen by immature DCs begin to proliferate for a few days, but then they die by apoptosis or become unresponsive to further activation. The ensuing depletion of antigen-specific T cell responses renders the host selectively tolerant to this antigen. By contrast, when DCs acquire antigens while they are exposed to maturation stimuli, the cells rapidly up-regulate MHC and costimulatory molecules and secrete several cytokines. The now mature DCs are potent inducers of effector T cells and immunological memory.

DC targeting can be accomplished by moieties including but not limited to molecules that bind DC-205, CD1 Ic, class II MHC, CD80, CD86, DC-SIGN, CD1 Ib, BDCA-I, BDCA-2, BDCA-4, Siglec-H, CX3CR1, and/or Langerin.

In some aspects, DC targeting can be accomplished by any targeting moiety that specifically binds to any entity (e.g., protein, lipid, carbohydrate, small molecule, etc.) that is prominently expressed and/or present on DCs (i.e., a DC marker). Exemplary DC markers include, but are not limited to, CDIa (R4, T6, HTA-I); CDIb (R1); CDIc (M241, R7); CDId (R3); CDIe (R2); CD1 Ib (αM Integrin chain, CR3, MoI, C3niR, Mac-1); CD1 Ic (αX Integrin, p150, 95, AXb2); CDwI 17 (Lactosylceramide, LacCer); CD19 (B4); CD33 (gp67); CD 35 (CR1, C3b/C4b receptor); CD 36 (GpIIIb, GPIV, PASIV); CD39 (ATPdehydrogenase, NTPdehydrogenase-1); CD40 (Bp50); CD45 (LCA, T200, B220, Ly5); CD45RA; CD45RB; CD45RC; CD45RO (UCHL-I); CD49d (VLA-4α, α4 Integrin); CD169 (Sialoadhesin, Siglec-1); CD208 (DC-LAMP); CD209 (DC-SIGN); CDw218a (IL 18Rα); CDw218b (IL8Rβ); CD227 (MUCl, PUM, PEM, EMA); CD230 (Prion Protein (PrP)); CD252 (OX40L, TNF (ligand) superfamily, member 4); CD258 (LIGHT, TNF (ligand) superfamily, member 14); CD265 (TRANCE-R, TNF-R superfamily, member 1 Ia); CD271 (NGFR, p75, TNFR superfamily, CD283 (TLR3, TOLL-like receptor 3); CD300c (CMRF-35A); CD301 (MGL1, CLECSF14); CD302 (DCLl); CD303 (BDCA2); CD304 (BDCA4); CD312 (EMR2); CD317 (BST2); CD319 (CRACC, SLAMF7); CD320 (8D6); and CD68 (gp1 10, Macrosialin); class II MHC.

In some aspects, T cell targeting can be accomplished by any targeting moiety that specifically binds to any entity (e.g., protein, lipid, carbohydrate, small molecule, etc.) that is prominently expressed and/or present on T cells (i.e., a T cell marker). Exemplary T cell markers include, but are not limited to, CD2 (E-rosette R, TI 1, LFA-2); CD3 (T3); CD3 α; CD3 β; CD3 ε; CD4 (L3T4, W3/25, T4); CD5 (TI, Tp67, Leu-1, LY-I); CD6 (T 12); CD7 (gp40, Leu 9); CD8a (Leu2, T8, Lyt2,3); CD8b (CD8, Leu2, Lyt3); CD1 Ia (LFA-1α, α Integrin chain); CD1 Ib (αM Integrin chain, CR3, MoI, C3niR, Mac-1); CD1 Ic (αX Integrin, p150, 95, AXb2); CD15s (Sialyl Lewis X); CD15u (3' sulpho Lewis X); CD15su (6 sulpho-sialyl Lewis X); CD 16b (FcgRIIIb); CDw 17 (Lactosylceramide, LacCer); CD 18 (Integrin 32 CD1 Ia, b, c β-subunit); CD26 (DPP IV ectoeneyme, ADA binding protein); CD27 (T14, S 152); CD28 (Tp44, T44); CD29 (Platelet GPIIa, β-1 integrin, GP); CD31 (PECAM-I, Endocam); CD35 (CRl, C3b/C4b receptor); CD37 (gp52-40); CD38 (ADP-ribosyl/cyclase, TlO); CD43 (Sialophorin, Leukosialin).

v. Immunostimulatory Agents

In some aspects, immunogenic composition or vaccine of the disclosures are formulated with one or more adjuvants such as gel-type adjuvants (e.g., aluminum hydroxide, aluminum phosphate, calcium phosphate, etc.), microbial adjuvants (e.g., immunomodulatory DNA sequences that include CpG motifs; endotoxins such as monophosphoryl lipid A; exotoxins such as cholera toxin, E. coli heat labile toxin, and pertussis toxin; muramyl dipeptide, etc.); oil-emulsion and emulsifier-based adjuvants (e.g., Freund's Adjuvant, MF59

[Novartis], SAF, etc.); particulate adjuvants (e.g., liposomes, biodegradable microspheres, saponins, etc.); synthetic adjuvants (e.g., nonionic block copolymers, muramyl peptide analogues, polyphosphazene, synthetic polynucleotides, etc.), and/or combinations thereof. Other exemplary adjuvants include some polymers (e.g., polyphosphazenes, described in U.S. Pat. No. 5,500,161, which is incorporated herein by reference), QS21, squalene, tetrachlorodecaoxide, etc.

vi. Assays for T Cell Activation

In some aspects, various assays can be utilized in order to determine whether an immune response has been elicited in a T cell or group of T cells (i.e., whether a T cell or group of T cells has become "activated"). In some aspects, stimulation of an immune response in T cells can be determined by measuring antigen-induced production of cytokines by T cells. In some aspects, stimulation of an immune response in T cells can be determined by measuring antigen-induced production of IFNγ, IL-4, IL-2, IL-IO, IL-17 and/or TNFα by T cells. In some aspects, antigen-produced production of cytokines by T cells can be measured by intracellular cytokine staining followed by flow cytometry. In some aspects, antigen-induced production of cytokines by T cells can be measured by surface capture staining followed by flow cytometry. In some aspects, antigen-induced production of cytokines by T cells can be measured by determining cytokine concentration in supernatants of activated T cell cultures. In some aspects, this can be measured by ELISA.

In some aspects, antigen-produced production of cytokines by T cells can be measured by ELISPOT assay. In general, ELISPOT assays employ a technique very similar to the sandwich enzyme-linked immunosorbent assay (ELISA) technique. An antibody (e.g. monoclonal antibody, polyclonal antibody, etc.) is coated aseptically onto a PVDF (polyvinylidene fluoride)-backed microplate. Antibodies are chosen for their specificity for the cytokine in question. The plate is blocked (e.g. with a serum protein that is non-reactive with any of the antibodies in the assay). Cells of interest are plated out at varying densities, along with antigen or mitogen, and then placed in a humidified 37° C. $CO_2$ incubator for a specified period of time. Cytokine secreted by activated cells is captured locally by the coated antibody on the high surface area PVDF membrane. After washing the wells to remove cells, debris, and media components, a secondary antibody (e.g., a biotinylated polyclonal antibody) specific for the cytokine is added to the wells. This antibody is reactive with a distinct epitope of the target cytokine and thus is employed to detect the captured cytokine. Following a wash to remove any unbound biotinylated antibody, the detected cytokine is then visualized using an avidin-HRP, and a precipitating substrate (e.g., AEC, BCIP/NBT). The colored end product (a spot, usually a blackish blue) generally represents an individual cytokine-producing cell. Spots can be counted manually (e.g., with a dissecting microscope) or using an automated reader to capture the microwell images and to analyze spot number and size. In some aspects, each spot correlates to a single cytokine-producing cell.

In some aspects, an immune response in T cells is said to be stimulated if between at least 1% and at least 100% of antigen-specific T cells produce cytokines. In some aspects, an immune response in T cells is said to be stimulated if at least 1%, at least 5%, at least 10%, at least 25%, at least 50%, at least 75%, at least 90%, at least 95%, at least 99%, or at least 100% of antigen-specific T cells produce cytokines.

In some aspects, an immune response in T cells is said to be stimulated if immunized subjects comprise at least 10-fold, at least 50-fold, at least 100-fold, at least 500-fold, at least 1000-fold, at least 5000-fold, at least 10,000-fold, at least 50,000-fold, at least 100,000-fold, or greater than at least 100,000-fold more cytokine-producing cells than do naive controls.

In some aspects, stimulation of an immune response in T cells can be determined by measuring antigen-induced proliferation of T cells. In some aspects, antigen-induced proliferation may be measured as uptake of $H^3$-thymidine in dividing T cells (sometimes referred to as "lymphocyte transformation test, or "LTT"). In some aspects, antigen-induced proliferation is said to have occurred if $H^3$-thymidine uptake (given as number of counts from a γ counter) is at least 5-fold, at least 10-fold, at least 20-fold, at least 50-fold, at least 100-fold, at least 500-fold, at least 1000-fold, at least 5000-fold, at least 10,000-fold, or greater than at least 10,000-fold higher than a naïve control.

In some aspects, antigen-induced proliferation may be measured by flow cytometry. In some aspects, antigen-induced proliferation may be measured by a carboxyfluorescein succinimidyl ester (CFSE) dilution assay. CFSE is a non-toxic, fluorescent, membrane-permeating dye that binds the amino groups of cytoplasmic proteins with its succinimidyl-reactive group (e.g. T cell proteins). When cells divide, CFSE-labeled proteins are equally distributed between the daughter cells, thus halving cell fluorescence with each division. Consequently, antigen-specific T cells lose their fluorescence after culture in the presence of the respective antigen ($CFSEP^{low}$) and are distinguishable from other cells in culture ($CFSE^{high}$). In some aspects, antigen-induced proliferation is said to have occurred if CFSE dilution (given as the percentage of $CFSE^{low}$ cells out of all $CFSE^+$ cells) is at least 5%, at least 10%, at least 25%, at least 50%, at least 75%, at least 90%, at least 95%, or at least 100%.

In some aspects, an immune response in T cells is said to be stimulated if cellular markers of T cell activation are expressed at different levels (e.g. higher or lower levels) relative to unstimulated cells. In some aspects, CDl Ia CD27, CD25, CD40L, CD44, CD45RO, and/or CD69 are more highly expressed in activated T cells than in unstimulated T cells. In some aspects, L-selectin (CD62L), CD45RA, and/or CCR7 are less highly expressed in activated T cells than in unstimulated T cells.

In some aspects, an immune response in T cells is measured by assaying cytotoxicity by effector CD8+ T cells against antigen-pulsed target cells. For example, a $^{51}$chromium ($^{51}$Cr) release assay can be performed. In this assay, effector CD8+ T cells bind infected cells presenting virus peptide on class I MHC and signal the infected cells to undergo apoptosis. If the cells are labeled with $^{51}$Cr before the effector CD8+ T cells are added, the amount Of $^{51}$Cr released into the supernatant is proportional to the number of targets killed.

One of ordinary skill in the art will recognize that the assays described above are only exemplary methods which could be utilized in order to determine whether T cell activation has occurred. Any assay known to one of skill in the art which can be used to determine whether T cell activation has occurred falls within the scope of this disclosure. The assays described herein as well as additional assays that could be used to determine whether T cell activation has occurred are described in Current Protocols in Immunology (John Wiley & Sons, Hoboken, N Y, 2007; incorporated herein by reference).

vii. Targeting B Cells

The present disclosure provides immunogenic composition or vaccine of the disclosures for delivery of, for example, immunogenic compositions to the cells of the immune system. In some aspects, immunogenic composition or vaccine of the disclosures comprise at least one immunogenic composition which can be presented to B cells (i.e., B cell antigens).

As described herein, one or more antigen variants of an immunogenic composition of the disclosure may comprise one or more targeting moieties. In some aspects, targeting moieties target particular cell types. In some aspects, a target is a B cell marker. In some aspects, a B cell target is an antigen that is expressed in B cells but not in non-B cells. In some aspects, a B cell target is an antigen that is more prevalent in B cells than in non-B cells.

In some aspects, a target is a SCS-Mph marker. In some aspects, an SCS-Mph target is an antigen that is expressed in SCS-Mph but not in non-SCS-Mph. In some aspects, an SCS-Mph target is an antigen that is more prevalent in SCS-Mph than in non-SCS-Mph. Exemplary SCS-Mph markers are listed below in the section entitled "Subcapsular Sinus Macrophage Cells" and include those provided elsewhere herein. In some aspects, a target is a FDC marker. In some aspects, an FDC target is an antigen that is expressed in FDCs but not in non-FDCs. In some aspects, an FDC target is an antigen that is more prevalent in FDCs than in non-FDCs. Exemplary FDC markers are listed below in the section entitled "Follicular Dendritic Cells" and include those provided elsewhere herein.

In some aspects, a target is preferentially expressed in particular cell types. For example, expression of an SCS-Mph, FDC, and/or B cell target in SCS-Mph, FDCs, and/or B cells is at least 2-fold, at least 3-fold, at least 4-fold, at least 5-fold, at least 10-fold, at least 20-fold, at least 50-fold, at least 100-fold, at least 500-fold, or at least 1000-fold overexpressed in SCS-Mph, FDCs, and/or B cells relative to a reference population. In some aspects, a reference population may comprise non-SCS-Mph, FDCs, and/or B cells.

The present disclosure encompasses the recognition that targeting of antigens to subcapsular sinus macrophages (SCS-Mph) is involved in efficient early presentation of lymph-borne pathogens, such as viruses, to follicular B cells (FIG. 2). As described in Example 1, following subcutaneous injection of vesicular stomatitis virus (VSV) or adenovirus (AdV) into the footpad of mice, viral particles were efficiently and selectively retained by CD169$^+$ SCS-Mph in the draining popliteal lymph nodes. VSV-specific B cell receptor (BCR) transgenic B cells in these lymph nodes were rapidly activated and generated extremely high antibody titers upon this viral challenge. Depletion of SCS-Mph by injection of liposomes laden with clodronate (which is toxic for Mph) abolished early B cell activation, indicating that SCS-Mph are essential for the presentation of lymph-borne particulate antigens to B cells.

In some aspects, SCS-Mph targeting can be accomplished by any targeting moiety that specifically binds to any entity (e.g., protein, lipid, carbohydrate, small molecule, etc.) that is prominently expressed and/or present on macrophages (i.e., SCS-Mph markers). Exemplary SCS-Mph markers include, but are not limited to, CD4 (L3T4, W3/25, T4); CD9 (p24, DRAP-I, MRP-I); CDl Ia (LFA-1α, α L Integrin chain); CDl Ib (αM Integrin chain, CR3, MoI, C3niR, Mac-1); CDl Ic (αX Integrin, p150, 95, AXb2); CDwl 2 (p90-120); CD13 (APN, gp150, EC 3.4.11.2); CD14 (LPS-R); CD15 (X-Hapten, Lewis, X, SSEA-I, 3-FAL); CD15s (Sialyl Lewis X); CD15u (3' sulpho Lewis X); CD15su (6 sulpho-sialyl Lewis X); CD16a (FCRIIIA); CD16b (FcgRIIIb); CDwl7 (Lactosylceramide, LacCer); CD18 (Integrin β2, CDl 1a,b,c β-subunit); CD26 (DPP IV ectoeneyme, ADA binding protein); CD29 (Platelet GPIIa, β-1 integrin, GP); CD31 (PECAM-I, Endocam); CD32 (FCγRII); CD33 (gp67); CD35 (CRl, C3b/C4b receptor); CD36 (GpIIIb, GPIV, PASIV); CD37 (gp52-40); CD38 (ADP-ribosyl cyclase, TlO); CD39 (ATPdehydrogenase, NTPdehydrogenase-1); CD40 (Bp50); CD43 (Sialophorin, Leukosialin); CD44 (EMCRII, H-CAM, Pgp-1); CD45 (LCA, T200, B220, Ly5); CD45RA; CD45RB; CD45RC; CD45RO (UCHL-I); CD46 (MCP); CD47 (gp42, IAP, OA3, Neurophillin); CD47R (MEM-133); CD48 (Blast-1, Hulym3, BCM-1, OX-45); CD49a (VLA-1α, α1 Integrin); CD49b (VLA-2α, gpla, α2 Integrin); or CD49c (VLA-3α, α3 Integrin).

In some aspects, SCS-Mph targeting can be accomplished by any targeting moiety that specifically binds to any entity (e.g., protein, lipid, carbohydrate, small molecule, etc.) that is prominently expressed and/or present on macrophages upon activation (i.e., activated SCS-Mph marker). Exemplary activated SCS-Mph markers include, but are not limited to, CDIa (R4, T6, HTA-I); CDIb (R1); CDIc (M241, R7); CD44R (CD44v, CD44v9); CD49d (VLA-4α, α4 Integrin); CD69 (AIM, EA 1, MLR3, gp34/28, VEA); CD 105 (Endoglin); CD 142 (Tissue factor, Thromboplastin, F3); CD 143 (ACE, Peptidyl dipeptidase A, Kininase II); CD153 (CD3OL, TNSF8); CD163 (M130, GHI/61, RM3/1); CD 166 (ALCAM, KG-CAM, SC-I, BEN, DM-GRASP); CD227 (MUC1, PUM, PEM, EMA); CD253 (TRAIL, TNF (ligand) superfamily, member 10); CD273 (B7DC, PDL2); CD274 (B7H1, PDL1); CD275 (B7H2, ICOSL); CD276 (B7H3); CD297 (ART4, ADP-ribosyltransferase 4; and Dombrock blood group glycoprotein; wherein the names listed in parentheses represent alternative names. Examples of such markers include those provided elsewhere herein.

In some aspects, B cell targeting can be accomplished by moieties that bind the complement receptors, CRl (i.e., CD35) or CR2 (i.e., CD21), proteins which are expressed on B cells as well as FDCs. In some aspects, B cell targeting can be accomplished by B cell markers such as CD 19, CD20, and/or CD22. In some aspects, B cell targeting can be accomplished by B cell markers such as CD40, CD52, CD80, CXCR5, VLA-4, class II MHC, surface IgM or IgD, APRL, and/or BAFF-R. The present disclosure encompasses the recognition that simultaneous targeting of B cells by moieties specific for complement receptors or other APC-associated molecules boosts humoral responses.

B cells that initially detect a previously unknown antigen generally express a B cell receptor (BCR, i.e., an antibody with a transmembrane domain) with suboptimal binding affinity for that antigen. However, B cells can increase by several orders of magnitude the affinity of the antibodies they make when they enter into a germinal center (GC) reaction. This event, which generally lasts several weeks, depends on FDC that accumulate, retain and present antigenic material to the activated B cells. B cells, while proliferating vigorously, repeatedly mutate the genomic sequences that encode the antigen binding site of their antibody and undergo class-switch recombination to form secreted high-affinity antibodies, mostly of the IgG isotype. GC reactions also stimulate the generation of long-lived memory B cells and plasma cells that maintain high protective antibody titers, often for many years. Vaccine that target FDC upon subcutaneous injection and that are retained on the FDC surface for long periods of time are predicted to boost GC reactions in response to vaccination and improve the affinity and longevity of desired humoral immune responses.

In some aspects, FDC targeting can be accomplished by moieties that bind the complement receptors, CR1 (i.e., CD35) or CR2 (i.e., CD21), proteins which are expressed on FDCs as well as B cells. Examples of moieties include those provided elsewhere herein.

GC reactions and B cell survival not only require FDC, but also are dependent on help provided by activated CD4 T cells. Help is most efficiently provided when a CD4 T cell is first stimulated by a DC that presents a cognate peptide in MHC class II (pMHC) to achieve a follicular helper ($T_{FH}$) phenotype. The newly generated TFH cell then migrates toward the B follicle and provides help to those B cells that present them with the same pMHC complex. For this, B cells first acquire antigenic material (e.g., virus or virus-like vaccine), internalize and process it (i.e., extract peptide that is loaded into MHC class II), and then present the pMHC to a $TF_H$ cell.

Thus, the present disclosure encompasses the recognition that a vaccine that elicits optimal humoral immunity can combine several features and components: (a) antigenic material for CD4 T cells that is targeted to and presented by DCs; (b) high density surface antigens that can be presented in their native form by SCS-Mph to antigen-specific follicular B cells; (c) the capacity to be acquired and processed by follicular B cells for presentation to TFH cells (the present disclosure encompasses the recognition that B cells readily acquire and internalize particulate matter from SCS-Mph); (d) the ability to reach FDC and be retained on FDC in intact form and for long periods of time; and (e) adjuvant activity to render APC fully immunogenic and to avoid or overcome tolerance.

In some aspects, an immunogenic composition or vaccine of the disclosure comprises at least one targeting moiety. In some aspects, all of the targeting moieties of an immunogenic composition or vaccine of the disclosure are identical to one another. In some aspects, an immunogenic composition or vaccine of the disclosure a number of different types of targeting moieties. In some aspects, an immunogenic composition or vaccine of the disclosure comprises multiple individual targeting moieties, all of which are identical to one another. In some aspects, a immunogenic composition or vaccine of the disclosure comprises exactly one type of targeting moiety. In some aspects, a immunogenic composition or vaccine of the disclosure comprises exactly two distinct types of targeting moieties. In some aspects, a immunogenic composition or vaccine of the disclosure comprises greater than two distinct types of targeting moieties.

In some aspects, a immunogenic composition or vaccine of the disclosure comprises at least one targeting moiety that is associated with the exterior surface of the immunogenic composition or vaccine of the disclosure. In some aspects, the association is covalent. In some aspects, the covalent association is mediated by one or more linkers. In some aspects, the association is non-covalent. In some aspects, the non-covalent association is mediated by charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof.

viii. Assays for B Cell Activation

In some aspects, various assays can be utilized in order to determine whether an immune response has been elicited in a B cell or group of B cells (i.e., whether a B cell or group of B cells has become "activated"). In some aspects, stimulation of an immune response in B cells can be determined by measuring antibody titers. In general, "antibody titer" refers to the ability of antibodies to bind and neutralize antigens at particular dilutions. For example, a high antibody titer refers to the ability of antibodies to bind and neutralize antigens even at high dilutions. In some aspects, an immune response in B cells is said to be stimulated if antibody titers are measured to be positive at dilutions at least 5-fold greater, at least 10-fold greater, at least 20-fold greater, at least 50-fold greater, at least 100-fold greater, at least 500-fold greater, at least 1000 fold greater, or more than at least 1000-fold greater than in non-immunized individuals or pre-immune serum.

In some aspects, stimulation of an immune response in B cells can be determined by measuring antibody affinity. In particular, an immune response in B cells is said to be stimulated or elictied if an antibody has an equilibrium dissociation constant (Kd) less than $10^{-7}$ M, less than $10^{-8}$ M, less than $10^{-9}$ M, less than $10^{-10}$ M, less than $10^{-11}$ M, less than $10^{-12}$ M, or less.

In some aspects, a T cell-dependent immune response in B cells is said to be stimulated if class-switch recombination has occurred. In particular, a switch from IgM to an IgG isotype or to IgA or to a mixture of these isotypes is indicative of a T cell dependent immune response in B cells.

In some aspects, an immune response in B cells is determined by measuring affinity maturation of antigen-specific antibodies. Affinity maturation occurs during the germinal center reaction whereby activated B cells repeatedly mutate a region of the immunoglobulin gene that encodes the antigen-binding region. B cells producing mutated antibodies which have a higher affinity for antigen are preferentially allowed to survive and proliferate. Thus, over time, the antibodies made by B cells in GCs acquire incrementally higher affinities. In some aspects, the readout of this process is the presence of high antibody titer (e.g. high affinity IgG antibodies that bind and neutralize antigens even at high dilutions).

In some aspects, an immune response in B cells is said to be stimulated if memory B cells and/or long-lived plasma cells that can produce large amounts of high-affinity antibodies for extended periods of time have formed. In some aspects, antibody titers are measured after different time intervals (e.g. 2 weeks, 1 month, 2 months, 6 months, 1 year, 2 years, 5 years, 10 years, 15 years, 20 years, 25 years, or longer) after vaccination in order to test for the presence of memory B cells and/or long-lived plasma cells that can produce large amounts of high-affinity antibodies for extended periods of time. In some aspects, memory B cells and/or long-lived plasma cells that can produce large amounts of high-affinity antibodies for extended periods of time are said to be present by measuring humoral responses (e.g., if humoral responses are markedly more rapid and result in higher titers after a later booster vaccination than during the initial sensitization). In some aspects, an immune response in B cells is said to be stimulated if a vigorous germinal center reaction occurs.

In some aspects, a vigorous germinal center reaction can be assessed visually by performing histology experiments. In some aspects, vigorous germinal center reaction can be assayed by performing immunohistochemistry of antigen-containing lymphoid tissues (e.g., vaccine-draining lymph nodes, spleen, etc.). In some aspects, immunohistochemistry is followed by flow cytometry.

In some aspects, an immune response in B cells is determined by analyzing antibody function in neutralization assays. In particular, the ability of a microorganism (e.g., virus, bacterium, fungus, protozoan, parasite, etc.) to infect a susceptible cell line in vitro in the absence of serum is compared to conditions when different dilutions of immune and nonimmune serum are added to the culture medium in which the cells are grown. In some aspects, an immune response in a B cell is said to be stimulated if infection of a microorganism is neutralized at a dilution of at least 1:5, at least 1:10, at least 1:50, at least 1:100, at least 1:500, at least 1:1000, at least 1:5000, at least 1:10,000, or less.

In some aspects, the efficacy of vaccines in animal models may be determined by infecting groups of immunized and non-immunized mice (e.g., 3 or more weeks after vaccination) with a dose of a microorganism that is generally lethal. The magnitude and duration of survival of both group is monitored and generally graphed a Kaplan-Meier curves. To assess whether enhanced survival is due to B cell responses, serum from immune mice can be transferred as a "passive vaccine" to assess protection of nonimmune mice from lethal infection.

One of ordinary skill in the art will recognize that the assays described above are only exemplary methods which could be utilized in order to determine whether B cell activation has occurred. Any assay known to one of skill in the art which can be used to determine whether B cell activation has occurred falls within the scope of this disclosure. The assays described herein as well as additional assays that could be used to determine whether B cell activation has occurred are described in Current Protocols in Immunology (John Wiley & Sons, Hoboken, N Y, 2007; incorporated herein by reference).

ix. Determination of Immune Response by Sequencing

In some cases, an elicited immune response to an immunogenic composition of the disclosure may be performed by direct sequencing of immune cells, including T cella dn B cells. For example, to determine if B cells or T cells have been stimulated by an immunogenic composition, cells from a subject, or host, to which the immunogenic composition has been previously administered, may be isolated. Genomic DNA or RNA may be extracted and sequenced using methods known in the art. Specific regions, such as the CDR may be analyzed to determine if certain sequences are present reflecting a response to an antigen. Further clonotype switching or affinity maturation may also be observed by sequencing and thereby also be indicative of an immune response.

Numerous methods of sequence determination are compatible with the systems and methods of the disclosures. Exemplary methods for sequence determination include, but are not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459,311 and 6,210,891; Balasubramanian, U.S. Pat. Nos. 7,232,656 and 6,833,246; Quake, U.S. Pat. No. 6,911,345; Li et al, Proc. Natl. Acad. Sci., 100: 414-419 (2003); pyrophosphate sequencing as described in Ronaghi et al., U.S. Pat. Nos. 7,648,824, 7,459,311, 6,828,100, and 6,210,891; and ligation-based sequencing determination methods, e.g., Drmanac et al., U.S. Pat. Appl. No. 20100105052, and Church et al, U.S. Pat. Appln Nos. 20070207482 and 20090018024.

Sequence information may be determined using methods that determine many (typically thousands to billions) nucleic acid sequences in an intrinsically parallel manner, where many sequences are read out preferably in parallel using a high throughput serial process. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

B. Therapeutic Applications

In other applications, the composition and methods of the disclosure may be used for the generation of an immune response or desired antibody to a target epitope. Antibodies may be widely useful tools for a variety of applications in addition to vaccines.

In some instances, for example, antibodies may be generated as a therapeutic drug. Numerous antibody based therapies comprise specific monoclonal antibodies directed towards a target molecule such as a cell receptor. In this case, a target molecule, or target protein associated with a disease, may be selected as an antigen. In some cases, an antibody, using methods described herein, may be raised against the specific target molecule. Target epitopes may be selected such that the binding of an antibody may inhibit the function or enhance the function of the target molecule. For example, antibody based therapies have been successfully employed against cell receptors such as VEFG for a numerous indications. Binding of monoclonal antibodies to the VEGF receptor, inhibits the binding of VEGF ligand for VEGF receptor and for some indications producing a therapeutic effect. Using composition and methods of this disclosure, a similar antibody, directed towards any selected antigen or target molecule, may be developed for a therapeutic purpose.

In other examples, an antibody therapeutic may be generated using the compositions and methods of the disclosure. For example, an antibody generated towards an antigen associated with a specific pathology may be chosen. In one example, the membrane receptor HER2 may contain certain mutations that are associated with breast cancer. HER2 mutants (gene variants containing oncogenic mutations) may be selected as an target antigen. In particular, a target epitope that is specific to the mutant HER2 variant may be chosen. Using compositions and methods of this disclosure, an antibody may be generated to a specific target epitope on the mutant HER2 protein. In some examples, the antibody may be made recombinantly, or generated in a mouse and further humanized for administration in a human subject who may have or suspected of having cancer. In some cases, an antibody therapeutic may be formulated whereby the antibody gerenated by the compositions and methods of this disclosure may be associated with (e.g. covalently linked, or conjugated) an chemotherapeutic agent, such as taxol. In some cases, the antibody may be used to target the chemotherapeutic agent to cells expressing the mutant HER2 protein, thereby selectively killing the cancer cells. In other examples, the antibody generated against mutant HER2 may be used to block or inhibit stimulatory signals from binding to the HER2 receptor and involved in maintaining the cancer cell. Inhibition of signaling through the HER2 receptor may decrease survivability or proliferation of the cancer cell.

In another example, the compositions and methods of this disclosure may be used to formulate a therapeutic that may selectively bind, and in some example attenuate or kill, certain clonotypes of T cell or B cells. In one example, an immunogenic composition of the disclosure may be formulated to contact a specific clonotype of cells, which may useful in the treatment of numerous diseases, such as autoimmune diseases, neurological diseases and inflammatory diseases. For example, in the case of an autoimmune disease such as lupus, certain T cells or B cells may be secreting antibodies or inflammatory agents that cause the disease. In some instances, certain T cell and B cell clonotypes may contain receptors specific for certain antigens. In the case of lupus, these antigens may be "self antigens" or proteins found on the surfaces of healthy cells in a patient suffering from lupus. In some cases it may be useful as a treatment to eliminate certain harmful clonotypes that produce antibodies and inflammatory agents in response to self antigens.

Using compositions and methods of the disclosure, an immunogenic composition may be formulated comprising self antigens recognized by specific harmful B and/or T cell clonotypes. In some cases, the immunogenic composition may comprise antigens associated with a toxin or chemotherapeutic for killing or attenuating B and T cells. When administered to a subject, the immunogenic composition may bind to B and/or T cells. In some cases the associated chemotherapeutic or toxin may selectively kill harmful immune cell clonotypes.

In another example, a therapeutic may also comprise an immune cell which has been trained to recognize a specific harmful antigen, such as that found in an infection, or from cancer. For example, immune cells may be trained to recognize and elicit a response to a cancer antigen such as Prostate-specific antigen, a cancer antigen found in subsets of subjects with prostate cancer. In some cases, immune cells may be harvested from a patient. An immunogenic composition of the disclosure, comprising Prostate-specific antigen variants may be administered to the immune cells. In some cases, APC cells, such as dendritic cells, may uptake members of the immunogenic composition and present peptides of the antigens on the surface. This may be achieved with techniques known in the art, such as lipid mediated delivery, electroporation, recombinant viral delivery and the like. In some cases, B cells may be selected that bind and secrete antibodies to the immunogenic composition. B cells may be allowed to undergo SMD to generate antibodies with increasing binding affinity and/or specificity. In some cases, these immune cells, such as the APCs, T cells or B cells may be administered back to a patient. In some cases, such as in the example of APCs, T cell in the patient's body will elicit an immune response to cells expressing the Prostate-specific antigen, thus killing cancer cells.

In another example, a therapeutic may also comprise a recombinant virus encoding one or more antigen variants of an immunogenic composition. In some cases, expression of antigen variant proteins may not be desirable before administration to a subject. Rather, nucleic acids encoding the antigen variants may be administered to a subject, whereby the antigen variants proteins are generated by the subject or host.

C. Diagnostic and Research Tools

Further, generation of specific antibodies specific for a target epitope may be useful as tools in diagnostics. Numerous cellular and biochemical assays rely upon antibodies for sensitive detection of trace amount of proteins. Various diagnostic tests ranging from HIV tests to tests for Hashimoto's disease require diagnostic tests that comprise antibodies. The composition and methods of the disclosure provide for the generation of a desired antibody to a target epitope on any selected antigen. The antibody may be used as a tool for any diagnostic test, biosensor, cellular or biochemical assay used in the detection of the antigen used to raise the antibody.

For example, the immunogenic composition of the disclosure may be used as as binding partner for certain antibodies. In one example, an immunogenic composition may be used to test the presence or absence of certain antibodies in the blood of a person having or suspected of having HIV. The immunogenic composition may be used as bait to determine the specificity and affinity of certain anti-HIV antibodies that may be present. In some examples, HIV antibodies present in blood may be isolated and complexed, in vitro, with one or more immunogenic compositions comprising HIV antigens. Immunoassays such as ELISA or surface Plasmon Resonance may be used to characterize the nature of the blood derived HIV antibodies. Information regarding the binding of the antigen variants of the immunogenic composition and the HIV antibodies may provide information about the amount of HIV antibodies present, the nature the antibodies (mature, vs. intermediate antibodies), the epitopes to which the antibodies have been generated the like. This information may be useful in the diagnosis and/or prognosis of HIV infection or any other pathologies associated with the infection.

Similarly, antibodies are essential tools for basic research and may be used for applications related to experimentation. Antibodies generated by the compositions and methods of the disclosure may be used for protein purification, or characterization or quantification of proteins of interest in basic research. The composition and methods of this disclosure provide for methods to generate a desired antibody for use as tools in a variety of basic research tool applications, including immunoassays.

V. System for Data Transmittal and Storage

Methods and composition of this disclosure has the capability of generating millions of bits of information pertaining to the design and formulation of various immunogenic compositions. The massive amount of raw and processed data generated from the compositions and methods of the disclosure may be stored in any manner that allows for archiving and retrieval, most often through memory storage devices accessed by computer. Given that the compositions and methods of the disclosure may be applied the development of vaccines, therapeutics diagnostics and other tools, there may be wide range of rules and regulations that may govern the use and storage of these data. For clinical testing of human subjects for example, appropriate consents must be obtained from parties involved and standard HIPAA regulations will govern how this information is stored and disseminated. In general, this information must be protected from access by any unauthorized individual and may be communicated from the clinical laboratory that performed the test only to the ordering physician or his/her designee in accordance with state and federal laws. In most cases, the ordering physician then shares this information with patients and medical staff who are directly involved in the case. For analyses of nonhuman species and research applications, a variety of federal and state laws and regulations, policies of funding agencies and institutional rules and regulations may impact how this information is stored and disseminated.

Figure 4:
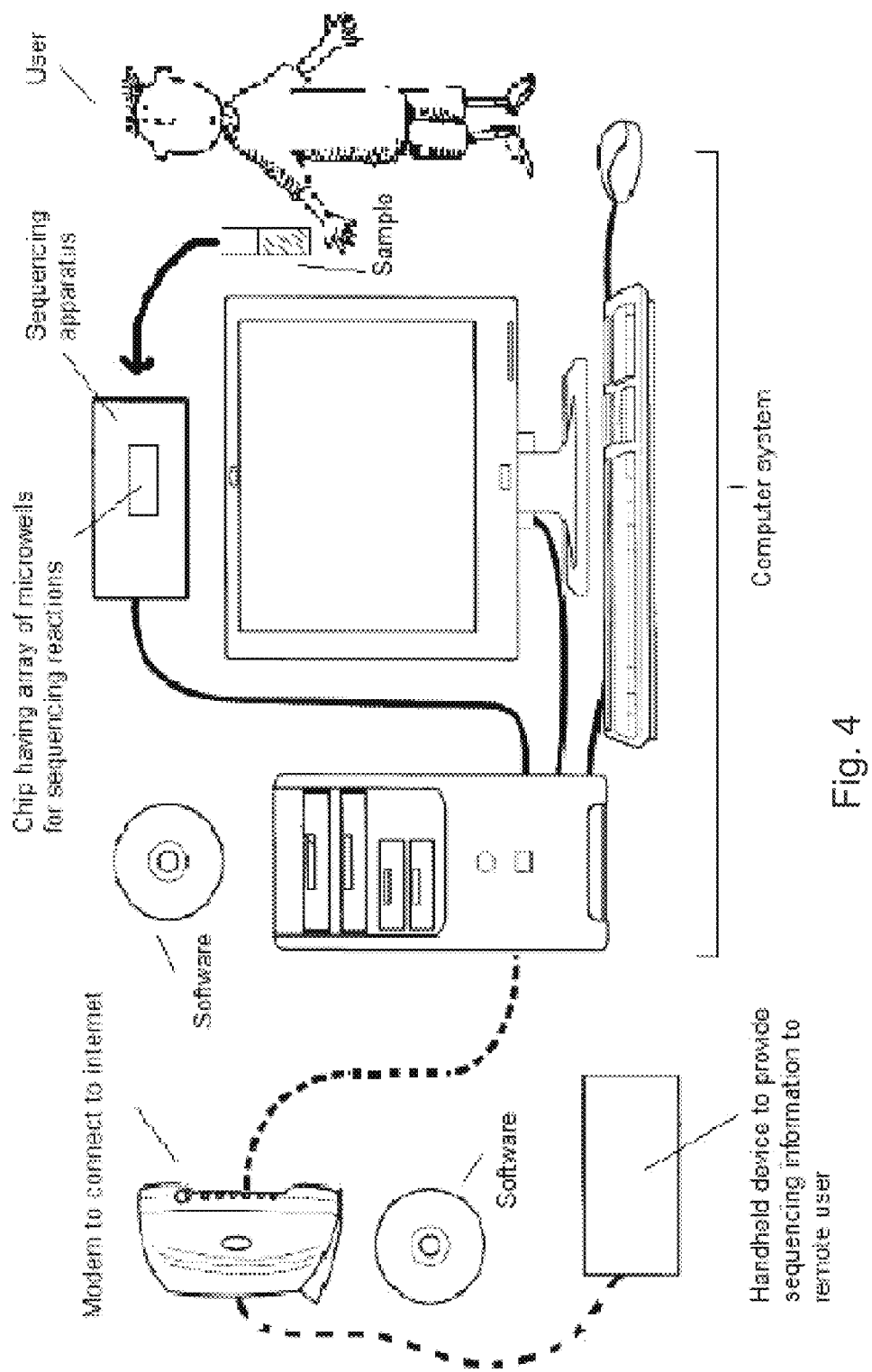
FIG. 4 is a schematic representation of storage and transmission of data of the compositions and methods of this disclosure.

Any appropriate method can be used to communicate information pertaining to data generated by the compositions and methods of the disclosure to another person. For example, information can be given directly or indirectly to a professional, and a laboratory staff member can input the report of vaccine design into a computer-based record. In some cases, information is communicated by making a physical alteration to medical or research records. For example, a medical professional may make a permanent notation or flag a medical record for communicating the risk assessment to other medical professionals reviewing the record. In addition, any type of appropriate communication can be used to communicate the risk assessment information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional. An exemplary diagram of computer based communication is shown in FIG. 4.

Another aspect of the invention provides a system that is configured to implement the methods of the disclosure. The system can include a computer server ("server") that is programmed to implement the methods described herein. FIG. 4 depicts a system adapted to enable a user to store, analyze, and process sequence information. The system includes a central computer server that is programmed to implement exemplary methods described herein. The server includes a central processing unit (CPU, also "processor") which can be a single core processor, a multi core processor, or plurality of processors for parallel processing. The server also includes memory (e.g. random access memory, read-only memory, flash memory); electronic storage unit (e.g. hard disk); communications interface (e.g. network adaptor) for communicating with one or more other systems; and peripheral devices which may include cache, other memory, data storage, and/or electronic display adaptors. The memory, storage unit, interface, and peripheral devices can be in communication with the processor through a communications bus (solid lines), such as a motherboard. The storage unit can be a data storage unit for storing data. The server is operatively coupled to a computer network ("network") with the aid of the communications interface. The network can be the Internet, an intranet and/or an extranet, an intranet and/or extranet that is in communication with the Internet, a telecommunication or data network. The network in some cases, with the aid of the server, can implement a peer-to-peer network, which may enable devices coupled to the server to behave as a client or a server. In some embodiments, the computing resources can be configured into a cloud-service model.

The storage unit can store files, such as sequence data, sample data, molecular barcodes, software, or any aspect of data associated with the invention. The data storage unit may be coupled with data that can bin sample sequence with the sample source or other information contained in a molecular barcode.

The server can communicate with one or more remote computer systems through the network. The one or more remote computer systems may be, for example, personal computers, laptops, tablets, telephones, smart phones, or personal digital assistants. The remote computer systems may, for example, be used to transmit patient data to a caregiver. The data or hardware or system, for example, may be encrypted or modified (e.g. to comply with HIPPA rules and standards).

In some situations the system includes a single server. In other situations, the system includes multiple servers in communication with one another through an intranet, extranet and/or the Internet.

The server can be adapted to store sample information, such as, for example, sample source, date, orientation, sequence, statistical data, or any other information of potential relevance. Such information can be stored on the storage unit or the server and such data can be transmitted through a network.

Methods as described herein can be implemented by way of machine (or computer processor) executable code (or software) stored on an electronic storage location of the server, such as, for example, on the memory, or electronic storage unit. During use, the code can be executed by the processor. In some cases, the code can be retrieved from the storage unit and stored on the memory for ready access by the processor. In some situations, the electronic storage unit can be precluded, and machine-executable instructions are stored on memory. Alternatively, the code can be executed on a second computer system.

Aspects of the systems and methods provided herein, such as the server, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

The results of sequencing can be presented to a user with the aid of a user interface, such as a graphical user interface.

VI. EXAMPLES

It will be understood by those of skill in the art that numerous and various modifications can be made to yield essentially similar results without departing from the spirit of the present disclosure. All of the references referred to herein are incorporated by reference in their entirety for the subject matter discussed. The following examples are included for illustrative purposes only and are not intended to limit the scope of the disclosure.

Example 1: Method of Obtain Structural Models of Variable Surface Glycoprotein To get a structural model of a Variable Surface Glycoprotein, 37 structural representatives from NCBI NR database are aligned. From the alignment a profile Hidden Markov Model is generated using the program HMMer3. The HMM is used to detect homologous structures in PDB with a minimum e-value of $1 \times 10^{-3}$. The HMM is used to align the structures' sequence to the reference sequence. An expected minimum threshold of 30% identity between at least one member of the antigen variants is set to assert sufficient homology. No more than 10% insertions/deletions in the local alignment region are permitted.

Example 2: Method for Diversifying TCR Epitopes

In this example, a library of antigenic variants is prepared, optimized for diversifying TCR epitopes. For diversifying a set of homologs in the non target epitope regions, antigen homologs are identified from a reference database for the antigen HIV gp120 protein. The antigens are aligned using the program MUSCLE. An HMM is generated using alignment data and the program HMMer. Structural models are obtained by searching PDB with the HMM generated from the alignment data. Structural model are aligned to homologs using HMM and a PWM is extracted from the alignment. Each position in the structures are mapped to a position in the alignment, a column in the HMM, and a column in the PWM. Map surface accessibility is determined for each column in the PWM from the structure by Modeller. MHC-II TCR epitopes are identified from literature and mapped to the PWM. Surface exposed residues are diversified. MHC-II TCR epitopes are optimized. Non-exposed TCR epitopes are masked so they are not further diversified. Optimizing dispersion is performed on the surface exposed residues by manipulating diversity frequencies in the remainder of the positions that are surface exposed and not part of TCR epitopes. At any time, the PWM is now a design that could be synthesized to produce an antigen library. A collection of 10000 sequences is sampled from the design in-silico by bioinformatics simulation and analyzed. If the sequences are either so similar to one another that they contain many off-target epitopes in common, or so distant from the reference structure that they have a low probability of folding, the PWM is altered and retested. Optimization is performed by linear scaling of non-dominant amino acid frequencies compared to dominant amino acid frequencies at each position. During testing, 90% of a set of 100 simulated molecules are observed to be greater than 40% identical to a known reference sequence, and no off-target epitope, defined as any collection of surface exposed residues within a 25 square angstrom radius centered on the carbon alpha backbone of a residue also on the surface, has a percent identity greater than 90% to any other member by pairwise comparison. If these criteria aren't met, the PWM is altered to be either more or less diverse and process repeated. As an alternative to linear scaling, a random Monte Carlo stochastic sampling, a genetic algorithm, or manual intervention could also be used to optimize the final PWM.

Example 3: Method for Optimizing BCR and TCR Epitopes in HIV gp120 Protein

In this example, a library of antigenic variants is prepared, optimized for diversifying TCR epitopes. For diversifying a set of homologs in the non target epitope regions: first identify antigen homologs from a reference database for the antigen HIV gp120 protein. The antigens are aligned using the program MUSCLE. An HMM is generated using alignment data and the program HMMer. Structural models are obtained by searching PDB with the HMM generated from the alignment data. Structural model are aligned to homologs using HMM and a PWM is extracted from the alignment. Each position in the structures are mapped to a position in the alignment, a column in the HMM, and a column in the PWM. Map surface accessibility is determined for each column in the PWM from the structure by Modeller. MHC-II TCR epitopes from literature are mapped to the PWM. Non-exposed residues are assigned as reference sequence. To optimize MHC-II TCR epitopes, a computational mask is placed on non-exposed and TCR epitopes so they are not further diversified. Optimized dispersion is performed by manipulating diversity frequencies in the remainder of the positions that are surface exposed and not part of TCR epitopes. At any time, the PWM is now a design that could be synthesized to produce an antigen library. A collection of 1000000 sequences can be sampled from the design in-silico by bioinformatics simulation and analyzed. If the sequences are either so similar to one another that they contain many off-target epitopes in common, or so distant from the reference structure that they have a low probability of folding, the PWM is altered and retested. Optimization is performed by linear scaling of non-dominant amino acid frequencies compared to dominant amino acid frequencies at each position. During testing, 80% of a set of 1000 simulated molecules are greater than 25% identical to a known reference sequence, and no off-target epitope, defined as any collection of surface exposed residues within a 100 square angstrom radius centered on the carbon alpha backbone of a residue also on the surface, and have a percent identity greater than 90% to any other member by pairwise comparison. If these criteria aren't met, the PWM is altered to be either more or less diverse. As an alternative to linear scaling, a random Monte Carlo stochastic sampling, a genetic algorithm, or manual intervention could also be used to optimize the final PWM.

Example 4: Method for Vaccine Development

In the case of generating one or more ensembles for the generation of a vaccine, specific algorithms and methods may be used. For example, a sequence database of all known variants for a target antigen, such as HA protein is aligned and rendered non-redundant at 90% identity. A positional weight matrix (PWM) is extracted from the alignment, to obtain a polymorphism compendium of all tolerated amino acids at all positions and their frequencies. A library design is optimized, using as input the PWM, applying amino acid variation to a reference H1N1 or H3N2 virus or B scaffold and eliminating length variation inconsistent with the reference scaffold. The scaffold is then diversified, preferentially weighting diversity to residues determined to be at least partially solvent accessible. To optimize the library, diversity in solvent accessible positions is then linearly scaled, with proportions of the most dominant "WT" residue compared to alternative diversity modified in order to optimize a library dispersion target according to the following scoring function: return true if <65% identity of any 25 Angstrom diameter surface "candidate epitope" when comparing any two variants from a randomly sampled set of 1000 selected members; else false. A parallel optimization cycle ensures maximum display of immunodominant MHC-I and MHC-II epitopes in the resulting molecules, preferably in conserved core regions shared among members. Scoring function is $\Sigma$((probability of peptide display by MHC display prediction)*(frequency of MHC carriers in population)*(probability of peptide in ensemble)).

The resulting library is then be expressed on Mammalian display (or Phage, Hyperphage, Yeast) and selected against broadly neutralizing antibodies (bnAbs) against known broadly neutralizing epitopes to select for variants still able to adopt native fold and present the broadly neutralizing epitopes. Residual diversity is evaluated by high-throughput sequence analysis of post-selection positive populations compared to library.

Provided sufficient residual diversity exists, additional rounds are further selected in the presence of heat, intercalating agents and other protein folding selective pressures. From the final selected pool of bnAb+/stability+ members, a set of 100 antigen variants exhibiting maximal epitope dispersion (i.e. most different from one another) will be selected, based on 10,000 Monte Carlo random starts of greedy addition of greatest distance members from the source pool into the final selection set, using the aforementioned function for optimization (i.e. pick a random member, then keep adding new members that are as far away from all of the previously selected members in the set as possible, and as far away from seasonal wt strains as possible, until 100 members is reached. This is performed 10,000 times, and then checked to see which set is the most dispersed).

The resulting 100 members are then expressed and tested to confirm folding and bnAb binding in the terminal expression system anticipated for production. A population of antigens is purified without His or other tags using bnAb affinity columns/beads/etc. The resulting pure pools are then combined into single ventivalent (20x), quinquavalent (50x), and centivalent (100x) pools composed of equal composition of each antigen. The performance of the vaccine is validated using FACS and an animal model.

FACS: A population of cells containing known bnAbs (a library of antibodies with spike in of broadly neutralizing B-cells, or a population of B-cells from an individual known to carry broadly neutralizing B-cells) is sorted, using the ensemble as a staining reagent. A single seasonal strain can act as a second color control to distinguish strain-specific B-cells from broadly elicited B-cells. Xivalent+++ cells are characterized individually for epitope by SPR in binning studies.

Animal model validation: Animal models (mice, ferrets, primates, or humans) are provided either a standard trivalent, an Xivalent, or a saline/adjuvant control. Xivalent doses are made such that the individual components are below the minimum concentration required for an effective immune response. Animals are subjected to cross-viral challenge against a novel strain not found in any of the vaccines, as well as direct viral challenge to the "seasonal" found in the trivalent standard of care. Responses are assayed by ELISA, FACS, viral titers, animal disease/fatality score, and high throughput sequencing of the BCR and TCR responding populations. In some cases, an antiviral agent may also be administered in addition to the tri-valent or Xivalent vaccine.

Example 5: Generation of HA Protein Ensembles 6500 hemagglutinin variants are obtained from the public record. Variants are all aligned to a profile using a Hidden Markov Model, rendered non-redundant at 95% identity, and analyzed for positional conservation using the Simpson's index. The resulting conservation profile is then displayed on a reference structure of hemagglutinin as shown in FIG. 3. The black/dark grey regions are regions that vary easily across different strains (300). Most regions of the protein appear non conserved as reflected in black/dark grey. Certain areas, marked in lighter grey (301), are conserved regions or regions that may be referred to as "broadly neutralizing stem" regions. This analysis naturally identified these regions based on sequence data. Formally, it identified a single patch (3x, given a trimer) of 50 $Å^2$, with high conservation profiles statistically discriminated above background perfectly overlaps a known broadly neutralizing epitope. This analysis is also a direct reflection of an epitope suitable for drug targeting or a an epitope as detected by a host immune system: the grey hotspots at high concentrations, and the dark regions at low concentrations.

Specifically, to generate this map of HA protein conservation, a large dataset of diverse sequences of the target antigen, or 6500 sequences of hemagglutinin are obtained. Next, a representative with a solved crystal structure is identified. The sequences are then aligned with the sequence of the crystal structure.

A profile hidden Markov Model to represent diverse HA protein is used to align the sequences accurately via the Viterbi algorithm. The resulting dataset has redundant sequences removed to reduce bias. For example, the HA dataset is reduced to 95% identity. A positional weight matrix (PWM) is obtained from the alignment that summarizes the frequency of all amino acids at all positions in the alignment. The PWM is filtered to remove positions that are mostly gap states (unusual inserts), and filtered to remove minority gap states by renormalizing the amino acid vectors in match-state dominant position. For example, mostly gappy positions in the HA alignment are removed, and the PWM are adjusted so that no positions show a chance of having "no amino acid" as an option. Every sequence that the PWM represented is made the same length. This length, and the consensus, is proximal to a variant known to fold. The PWM is then considered a library design. It contains instructions for what amino acids to appear at what positions at what frequencies.

Different antigen variants are then optimized with diversity in the design. A target dispersion of molecules in a given library size are taken as input, and the individual diversity vectors are uniformly scaled during iterations to produce a resulting library that emits a sequence distribution at the desired dispersion state. For example a library of 100 million HA variants on yeast display are panned. All of the molecules are selected to differ by at least 10% from the next closest member, and have an average distance of 50% identity across the library. The algorithm is then "stretched" the amino acid diversity at all positions until that criteria was met.

Additional selection steps included rational modification of critical sites to improve library performance. For example, some mutation combinations are not predicted to work in nature, so they are removed them from the library. The target epitope is also optimized to maintain more conservation on purpose. Similarly the core of the protein is also optimized to maintain more conservation, and leave diversity predominantly in surface exposed residues. Additionally, rationally encoded CD4+ and CD8+ specific T-cell epitopes known to aid in elicitation into the core of the protein are also added to the design.

The library is then commercially synthesized and produced. The PWM is sent to a synthesis company to produce a library bearing the diversity of the design. The library may be sent to TRIM synthesis (Mohan, Glanville etc 2013) or Isogenica 6tuple synthesis (Zhai & Glanville 2011).

The library is then displayed on phage. We attach fluorophores to many antibody variants known to recognize the broadly neutralizing epitope, and then sort the library using this color marker. Only HA variants that can still be recognized by broadly neutralizing antibodies of many sources are selected out of the library Temperature selection of the library. The experiment from the previous step is repeated at higher temperatures and in the presence of destabilizing agents in order to select for very stable versions of HA that will be easier to work with during manufacturing.

An immunogenic composition for a vaccine is formulated for flu based on the designed ensemble.

Example 6: Generation of a KRAS-Mutant Vaccine Therapeutic

The KRAS receptor is a signaling receptor often mutated in various cancers, including lung cancer and colorectal cancers. 100 KRAS variants including the commonly oncogenic KRAS P.G12D variant, are obtained from the public record. Variants are all aligned to a profile using a Hidden Markov Model, rendered non-redundant at 95% identity, and analyzed for positional conservation using the Simpson's index. The resulting conservation profile is then displayed on a reference structure of KRAS. Most regions of the protein appear conserved in certain areas. In some areas, non conserved substitutions are found, including the P.G12D mutation. This analysis naturally identifies these regions based on sequence data.

Specifically, to generate the map of KRAS protein conservation, a large dataset of diverse sequences of the target antigen, or 100 sequences of KRAS are obtained. Next, a representative with a solved crystal structure was identified. The sequences were then aligned with the sequence of the crystal structure.

A profile hidden Markov Model to represent diverse KRAS protein is used to align the sequences accurately via a neural network algorithm. The resulting dataset had redundant sequences are removed to reduce bias. For example, the KRAS dataset is reduced to 95% identity. A positional weight matrix (PWM) is obtained from the alignment that summarizes the frequency of all amino acids at all positions in the alignment. The PWM is filtered to remove positions that are mostly gap states (unusual inserts), and filtered to remove minority gap states by renormalizing the amino acid vectors in match-state dominant position. For example: mostly gappy positions in the KRAS alignment were removed, and the PWM is adjusted so that no positions show a chance of having "no amino acid" as an option. Every sequence that the PWM represents is made the same length. This length, and the consensus, is proximal to a variant known to fold. The PWM was then considered a library design. It contained instructions for what amino acids to appear at what positions at what frequencies. An epitope containing the KRAS P.G12D mutation is selected as the target epitope.

Different antigen variants are then optimized with diversity in the design. A target dispersion of molecules in a given library size are taken as input, and the individual diversity vectors are uniformly scaled during iterations to produce a resulting library that emits a sequence distribution at the desired dispersion state. For example a library of 1 million KRAS variants on yeast display was panned. All of the molecules were selected to differ by at least 10% from the next closest member, and have an average distance of 50% identity across the library. The algorithm then "stretches" the amino acid diversity at all positions until that criteria is met.

Additional selection steps include rational modification of critical sites to improve library performance. For example, some mutation combinations are not predicted to work in nature, so they are removed them from the library. The target epitope is also optimized to maintain more conservation on purpose. Similarly the core of the protein was also optimized to maintain more conservation, and leave diversity predominantly in surface exposed residues. Additionally, rationally encoded CD4+ and CD8+ specific T-cell epitopes known to aid in elicitation into the core of the protein are also added to the design.

The library is then commercially synthesized and produced. The PWM is sent to a synthesis company to produce a library bearing the diversity of the design. The library may be sent to TRIM synthesis (Mohan, Glanville etc 2013) or Isogenica 6tuple synthesis (Zhai & Glanville 2011).

The library is then displayed on phage are various temperatures and repeated at in the presence of destabilizing agents in order to select for very stable versions of KRAS that will be easier to work with during manufacturing.

Each KRAS variant is scored based on biochemical stability and the ability to be expressed. After scoring, an immunogenic composition is formulated based on the designed ensemble. Various KRAS variants are selected from the library based on biochemical stability. The most stable molecules are generated and combined in various ratios, such that each antigen in the immunogenic composition is not, in isolation, at a concentration capable of eliciting an immune response when administered in a subject An immunogenic composition is formulated using various KRAS antigen variants. Various targeting molecules are also included, such as a peptide that binds CD138 (Syndecan-1, Heparan sulfate proteoglycan) for specific targeting of the immunogenic to B cells, as well as an apatmer that binds CD25 (Tac antigen, IL-2Rα, p55), for for specific targeting of the immunogenic composition to T cells.

The immunogenic composition is then administered subcutaneously, with acceptable pharmaceutical carriers, into a human patient having or suspected of having a cancer resulting from KRAS P.G12D mutation.

The patient's immune cells produce both an antibody and cytotoxic T cell response to cancer cells containing the KRAS P.G12D mutation. B-cell and T-cells of the patient do not elicit an immune response to non-target epitopes, such as wildtype KRAS receptors (e.g. receptors not containing the KRAS P.G12D mutation.

Example 7: Generation of a KRAS P.G12D Antibody Therapeutic

In an alternative example, the immunogenic composition formulated using various KRAS P.G12D antigen variants of Example 6 may be used to generate a therapeutic antibody. In this case, the immunogenic composition may be administered to a mouse or rabbit hybridoma cells. Hybridoma cells that produce an antibody that is specific for the KRAS P.G12D epitope are selected. Further rounds of antibody optimization may also be included, whereby hypersomatic mutation allows for improved binding affinity of the antibody to the target epitope.

Nucleic acids from hybridomas producing selective antibodies to the KRAS P.G12D may be sequenced to determine the coding sequence for the antibodies. Nucleic acids may be cloned into expression vectors and the sequence further optimized. The sequence may be mutated to incorporate mutations to "humanize" the antibody as known in the art.

Humanized recombinant antibodies may be recombinantly expressed and purified from in vitro cell culture lines, such as HEK293 cells. A therapeutic antibody formulation is generated by conjugating the KRAS P.G12D antibody to a chemotherapeutic agent, such as cisplatin. The therapeutic agent may be then administered subcutaneously, with acceptable pharmaceutical carriers, into a human patient having or suspected of having a cancer resulting from KRAS P.G12D mutation. The antibody formulation specifically binds to cancer cells expressing the KRAS P.G12D receptor. The attached chemotherapeutic selectively kills those cells.

Example 8: Generation of a KRAS P.G12D Immune Cell Therapeutic

In an alternative example, the immunogenic composition formulated using various KRAS P.G12D antigen variants of Example 6 may be used to generate an immune cell therapeutic. In this case, the immunogenic composition may be administered to one or more immune cells harvested from a patient in need of treatment or prevention of cancer containing the KRAS P.G12D mutation. Dendritic cells (DCs) may be harvested from a patient and cultured in vitro. The immunogenic composition of Example 6 is administered to the DCs. In some examples, DCs are electroporated to allow for antigens of the immunogenic composition to be taken up and present on MHC molecules. In other examples, nucleic acids encoding antigen variants are administered to the DCs, such as through lipid based transfer or through recombinant viral delivery vectors. Additional agents may be used to help elicit MHC presentation of the KRAS P.G12D antigen variants.

DCs cells are tested using a range of immune assays including ELISA or FACs to observe presentation of the KRAS P.G12D antigens. DCs demonstrating this presentation may then be administered to the subject from whom the cells were originally derived, or administered to a different subject in need of treatment.

Once inside the subject, DCs may allow for the subject to elicit an immune response to KRAS P.G12D antigens, either through T cell or B cell response pathways.

Example 8: Generation of a KRAS P.G12D DNA Vaccine

In an alternative example, the immunogenic composition formulated using nucleic acids encoding various KRAS P.G12D antigen variants of Example 6 may be used to generate a therapeutic. In this case, the immunogenic composition comprises a plurality of nucleic acids may encoding one or more proteins sequence of KRAS antigenic variants. In one example nucleic acids are conjugated to a suitable vector, such as lipid base delivery vehicle to be administered into patient in need of treatment or prevention of cancer containing the KRAS P.G12D mutation. In another example, the nucleic acids encoding the immunogenic composition may be delivered via recombinant viral vectors.

Once inside the subject, nucleic acids encoding the immunogenic composition may enter the subject's or host cells. In some cases, the cells are immune cells. In some cases, the nucleic acids are targeted to diseased cells. In the case of diseased cell, the cells uptake the nucleic acids. Inside the host cells, the nucleic acids are transcribed and/or translated to produce antigen variant proteins. In one example, the antigen proteins may be secreted by the cells, or displayed on the outside of the cell. The host's or subject's immune system generates an immune response to cells expressing the antigen variants of the immunogenic composition, thus killing the diseased or cancer cells. The immune response may be generated through innate, humoral or adaptive responses.

Example 9: Select for Epitope-Specific Repertoires in a Phage Display, Yeast Display, CIS Display A target epitope is known for an antigen of interest, and it is desirable to engineer antibodies against that epitope, while minimizing time spent characterizing antibodies against other epitopes. A set of 6 or more antigen variants are designed that share the conserved epitope but differ in other epitopes. The antigen pool is produced and presented in parallel during selection, either against an unselected library, or a library already exposed to one or more enrichment rounds against the native antigen. The total antigen concentration is limited during enrichment to simultaneously select for epitope specificity and off-rate. Non-labeled competitor wildtype can be introduced during incubation steps to further select for epitope specificity and off-rate. Some of the antigens can be presented in parallel during selection for optimization purposes, such as through phage display, yeast display, CIS display, or mammalian display. High throughput sequencing of enrichment round pools can aid in discovery or detection of specific selectivity of clonotypes.

Example 10: Select Epitope-Specific Repertoires by Flow Cytometry of Human Cells or Mass Cytometry of Human Cells A target epitope is known for an antigen of interest, and it is desirable to recover antibodies against the epitope. A set of 6 or more antigen variants are designed that share the conserved epitope but differ in other epitopes. Each antigen could optionally be provided a different marker, up to the limiting number of available markers. Antigens can also be pooled on the same markers. The cells are incubated with the labeled antigens and then sorted by cytometry. The number of markers on a cell, as well as the intensity of decoration of that cell, can both be used to select for broadly reactive epitope binders. In some examples, the markers represent fluorophores or combinations of fluorescent signals that be detectable using flow cytometry or mass cytometry of cells.

Example 11: Development of Bi-Specific T-Cell Engagers

The methods and compositions of the disclosure are used to develop a Bi-specific T-cell engagers (BiTEs) a a class of artificial bispecific monoclonal antibodies that are investigated for the use as anti-cancer drugs. They direct a host's immune system, more specifically the T cells' cytotoxic activity, against cancer cells.

BiTEs are fusion proteins consisting of two single-chain variable fragments (scFvs) of different antibodies, or amino acid sequences from four different genes, on a single peptide chain of about 55 kilodaltons.

The compositions and methods of the disclosure may be used to develop antibody or antibody fragments for a BiTE molecule. For example, the compositions and methods of the disclosure are used to generate an antibody toward CD3, a specific T cell marker as described herein. The other antibody of the BiTE molecule may be an antibody generated towards a tumor antigen (such as HER2). Thus one of the scFvs is designed to binds to T cells via the CD3 receptor, and the other to a tumor cell via a tumor specific molecule, such as HER2, bringing the T cell into proximity with the cancer cell. The T cell is then activated to kill the cancer cell.

What is claimed is:

1. A computing device comprising a processor; and data storage, storing instructions that, upon execution by the processor, cause the computing device to perform functions comprising:

a. obtaining a target antigen protein sequence and one or more antigen homolog sequences;

b. obtaining structural models of the target antigen protein sequence and the one or more antigen homolog sequences and identifying a plurality of surface-exposed amino acid residues;

c. generating, in silico, a library of a plurality of antigen variants using the structural models, wherein such generation comprises:

i. diversifying non-target epitope surface exposed amino acid residues for each antigen variant based on the structural models;

ii. performing comparisons between each of a plurality of non-target epitope surface exposed regions comprising a commonly defined area between antigen variants of the library, wherein antigen variants of the library share at least 30% sequence identity in non surface exposed amino acid residues, and wherein antigen variants of the library share at most 90% sequence identity in non target epitope surface exposed amino acid residues; and d. selecting six or more antigen variants generated in (c).

2. The device of claim 1, wherein the functions further comprise, following step (b), aligning the structural models of the target antigen and the one or more antigen homolog sequences to create an alignment.

3. The device of claim 2, following the step of claim 2, wherein the functions further comprise extracting a weighted score for each amino acid residue frequency of the target antigen protein sequences using the alignment.

4. The device of claim 3, wherein the weighted score is a positional weight matrix.

5. The device of claim 4, wherein the positional weight matrix comprises an identity and a frequency of each amino acid permitted at each structurally conserved position in all known variants of the antigen.

6. The device of claim 3, wherein the functions further comprise, following the step of claim 3, identifying surface exposed amino acid residues using the weighted score.

7. The device of claim 5, wherein the functions further comprise, following the step of claim 5, identifying amino acid residues of one or more target epitopes using the weighted score.

8. The device of claim 5, wherein the functions further comprise, following the step of claim 5, identifying one or more target epitopes using the weighted score.

9. The device of claim 7, wherein the functions further comprise, following the step of claim 7, identifying one or more target epitopes using the weighted score.

10. The device of claim 1, wherein the target antigen protein sequence comprises the sequence of a: pneumococcal antigen, tuberculosis antigen, anthrax antigen, HIV antigen, seasonal or epidemic flu antigen, Meningococcal antigen, *Haemophilus* antigen, or a HPV antigen.

11. The device of claim 1, wherein the library of a plurality of antigen variants comprises at least $1\times10^5$ antigen variants.

12. The device of claim 1, wherein the library of a plurality of antigen variants comprises at least $1\times10^6$ antigen variants.

13. The device of claim 1, wherein the library of a plurality of antigen variants comprises at least $1\times10^7$ antigen variants.

14. The device of claim 1, wherein the data storage is further configured to store at least some of the sequences of the antigens.

15. The device of claim 1, wherein one or more peripheral devices are in communication with the processor.

16. The device of claim 1, wherein the device is operatively coupled to a network.

17. The device of claim 16, wherein the network is an internet, an intranet, an extranet, a telecommunication network, or a data network.

* * * * *